United States Patent [19]

Kamiya et al.

[11] Patent Number: 4,560,765

[45] Date of Patent: Dec. 24, 1985

[54] 3,7-DISUBSTITUTED-3-CEPHEM-4-CARBOXYLIC ACID COMPOUNDS AND PROCESSES FOR PREPARATION THEREOF

[75] Inventors: Takashi Kamiya, Suita; Kunihiko Tanaka, Toyonaka; Yoshiharu Nakai, Otsu; Kazuo Sakane, Amagasaki, all of Japan

[73] Assignee: Fujisawa Pharmaceutical Co., Ltd., Osaka, Japan

[21] Appl. No.: 571,700

[22] Filed: Jan. 18, 1984

Related U.S. Application Data

[62] Division of Ser. No. 291,777, Aug. 10, 1981, Pat. No. 4,440,766, which is a division of Ser. No. 772,734, Feb. 28, 1977, Pat. No. 4,303,655.

[30] Foreign Application Priority Data

Mar. 9, 1976 [GB] United Kingdom ............... 9425/76
Oct. 4, 1976 [GB] United Kingdom ............. 41145/76

[51] Int. Cl.[4] ............... C07D 277/44; C07D 277/46; C07D 277/48
[52] U.S. Cl. ................................................ 548/194
[58] Field of Search ......................................... 548/194

[56] References Cited

U.S. PATENT DOCUMENTS

| | | | |
|---|---|---|---|
| 3,954,732 | 5/1976 | Kamiya et al. | 544/271 |
| 4,008,246 | 2/1977 | Ochiai et al. | 544/271 |
| 4,093,803 | 6/1978 | Cook et al. | 544/271 |
| 4,098,888 | 7/1978 | Ochiai et al. | 544/271 |
| 4,113,940 | 9/1978 | Kamiya et al. | 544/271 |
| 4,278,671 | 7/1981 | Ochiai | 424/246 |
| 4,298,606 | 11/1981 | Ochiai et al. | 544/271 |

Primary Examiner—Robert Gerstl

Attorney, Agent, or Firm—Oblon, Fisher Spivak, McClelland & Maier

[57] ABSTRACT

Antibiotic cephalosporin compounds, method of making and pharmaceutical composition thereof represented by the general formula

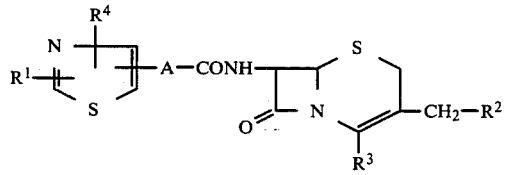

wherein
$R^1$ is amino, lower alkylamino, a protected amino, a protected lower alkylamino, hydroxy or lower alkoxy,
$R^2$ is hydrogen, acyloxy, pyridium or a heterocyclicthio group which may have suitable substituent(s),
$R^3$ is carboxy or its derivative,
A is carbonyl, hydroxy(lower)alkylene or a protected hydroxy(lower)alkylene and
$R^4$ is hydrogen or halogen, or
$R^2$ and $R^3$ are linked together to represent a group of the formula —COO—, this divisional application being directed to intermediate compounds of the formula:

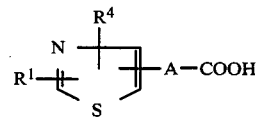

8 Claims, No Drawings

3,7-DISUBSTITUTED-3-CEPHEM-4-CARBOXYLIC ACID COMPOUNDS AND PROCESSES FOR PREPARATION THEREOF

This is a division, of application Ser. No. 291,777, filed Aug. 10, 1981, now U.S. Pat. No. 440766, which in turn is a division of Ser. No. 772,734, filed Feb. 28, 1977, now U.S. Pat. No. 4,303,655.

The present invention relates to new 3,7-disubstituted-3-cephem-4-carboxylic acid compounds and pharmaceutically acceptable salts thereof. More particularly, it relates to new 3,7-disubstituted-3-cephem-4-carboxylic acid compounds and pharmaceutically acceptable salts thereof which have antimicrobial activities and to processes for the preparation thereof, to pharmaceutical composition comprising the same, and to a method of using the same therapeutically in the treatment of infectious diseases in animals and human being.

Accordingly, it is one object of the present invention to provide 3,7-disubstituted-3-cephem-4-carboxylic acid compounds and pharmaceutically acceptable salts thereof, which are active against a number of pathogenic microorganisms.

Another object of the present invention is to provide processes for the preparation of 3,7-disubstituted-3-cephem-4-carboxylic acid compounds and pharmaceutically acceptable salts thereof.

A further object of the present invention is to provide pharmaceutical composition comprising, as active ingredients, said 3,7-disubstituted-3-cephem-4-carboxylic acid compounds and pharmaceutically acceptable salts thereof.

Still further object of the present invention is to provide a method for the treatment of infectious diseases caused by pathogenic bacteria in human being and animals.

The object 3,7-disubstituted-3-cephem-4-carboxylic acid compounds are novel and can be represented by the following general formula (I)

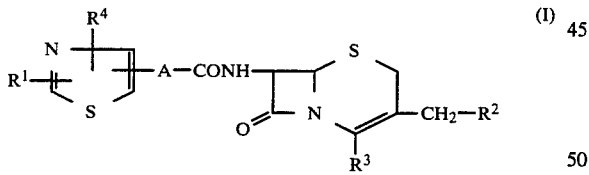

wherein
$R^1$ is amino, lower alkylamino, a protected amino, a protected lower alkylamino, hydroxy or lower alkoxy,
$R^2$ is hydrogen, acyloxy, pyridinium or a heterocyclic-thio group which may have suitable substituent(s),
$R^3$ is carboxy or its derivative,
A is carbonyl, hydroxy(lower)alkylene or a protected hydroxy(lower)alkylene and
$R^4$ is hydrogen or halogen, or
$R^2$ and $R^3$ are linked together to represent a group of the formula: —COO—,
wherein $R^3$ is —COO⁻ when $R^2$ is pyridinium, provided that $R^2$ is not acetoxy or 1-methyl-1H-tetrazol-5-ylthio when the group of the formula:

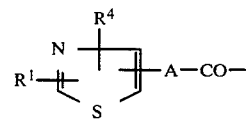

is 2-hydroxy-2-(2-amino-1,3-thiazol-4-yl)acetyl or 2-hydroxy-2-[2-(2,2,2-trichloroethoxy)carbonylamino-1,3-thiazol-4-yl]acetyl.

According to the present invention, the 3,7-disubstituted-3-cephem-4-carboxylic acid compounds (I) can be prepared by conventional various processes which are illustrated by the following scheme, in which the process comprising step, (II)→(I) is a fundamental process and the others are alternative processes.

Process 1.

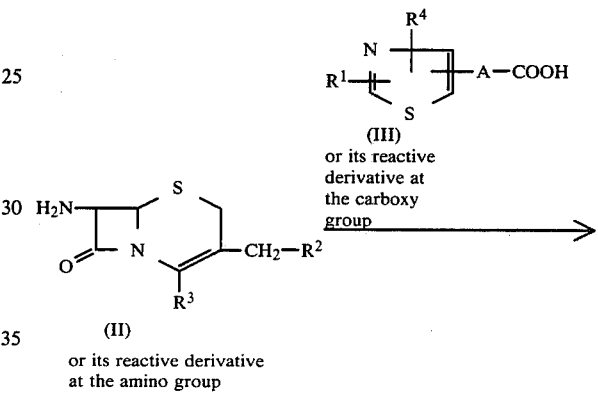

Process 2

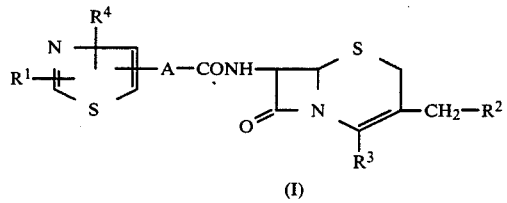

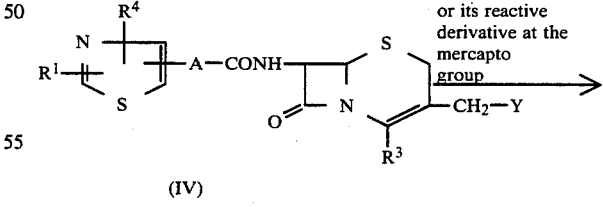

Process 3

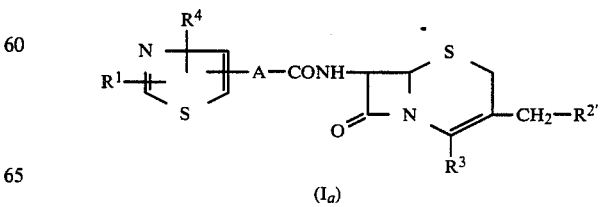

3

-continued

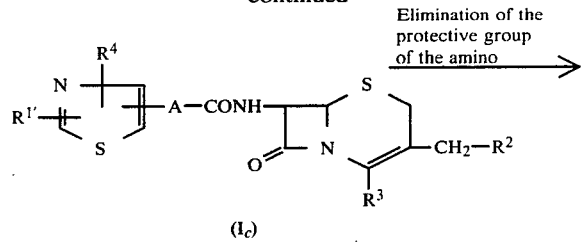

(I_c)

Elimination of the protective group of the amino →

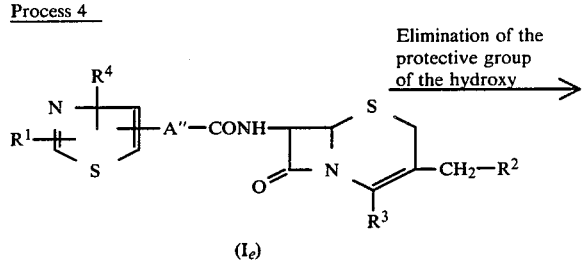

(I_b)

Process 4

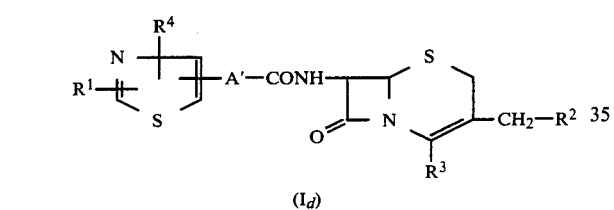

(I_e)

Elimination of the protective group of the hydroxy →

(I_d)

4

-continued

Process 5

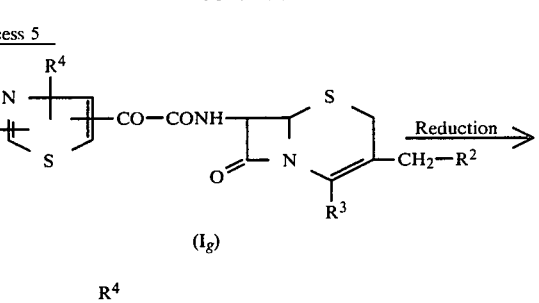

(I_g)     Reduction →

(I_f)

wherein
R$^1$, R$^2$, R$^3$, R$^4$ and A are each as defined above,
R$^{1\prime}$ is a protected amino or a protected lower alkyl-amino,
R$^{1\prime\prime}$ is amino or lower alkylamino,
R$^{2\prime}$ is a heterocyclic-thio group which may have suitable substituent(s),
A' is hydroxy(lower)alkylene,
A'' is a protected hydroxy(lower)alkylene and
Y is a conventional group which is capable to be replaced by the residue (—R$^{2\prime}$) of a compound of the formula: HR$^{2\prime}$ in which R$^{2\prime}$ is as defined above.

The starting compounds(III) and (IV) can be prepared by the processes which are illustrated by the following scheme.

(1)

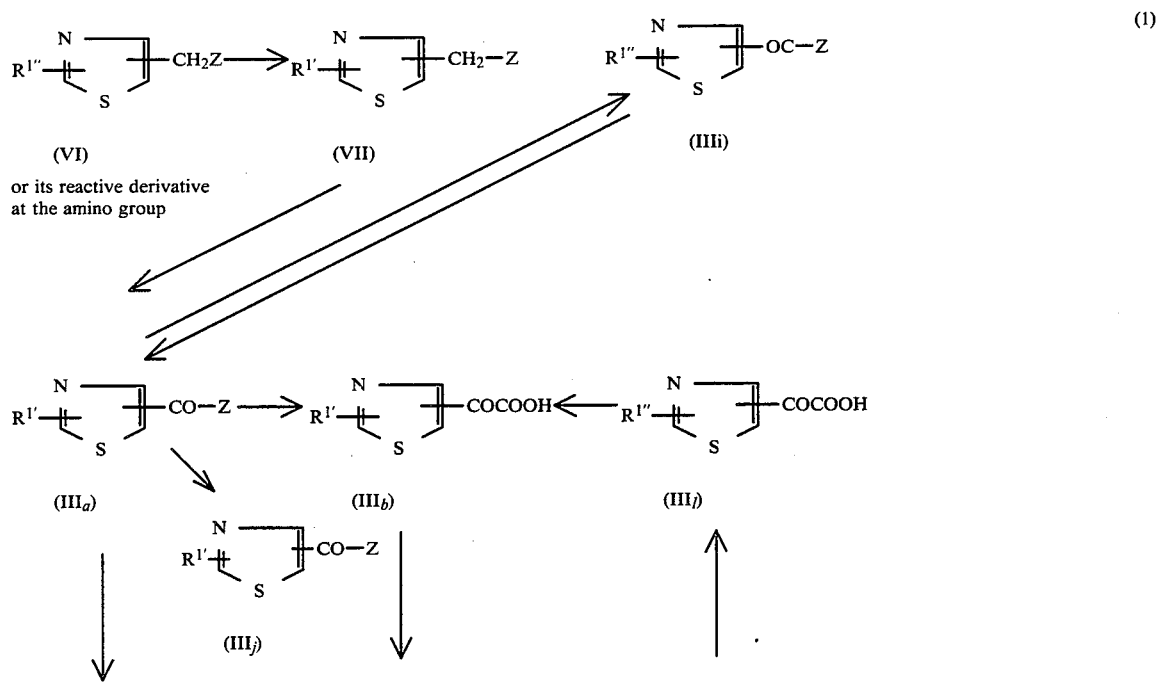

-continued

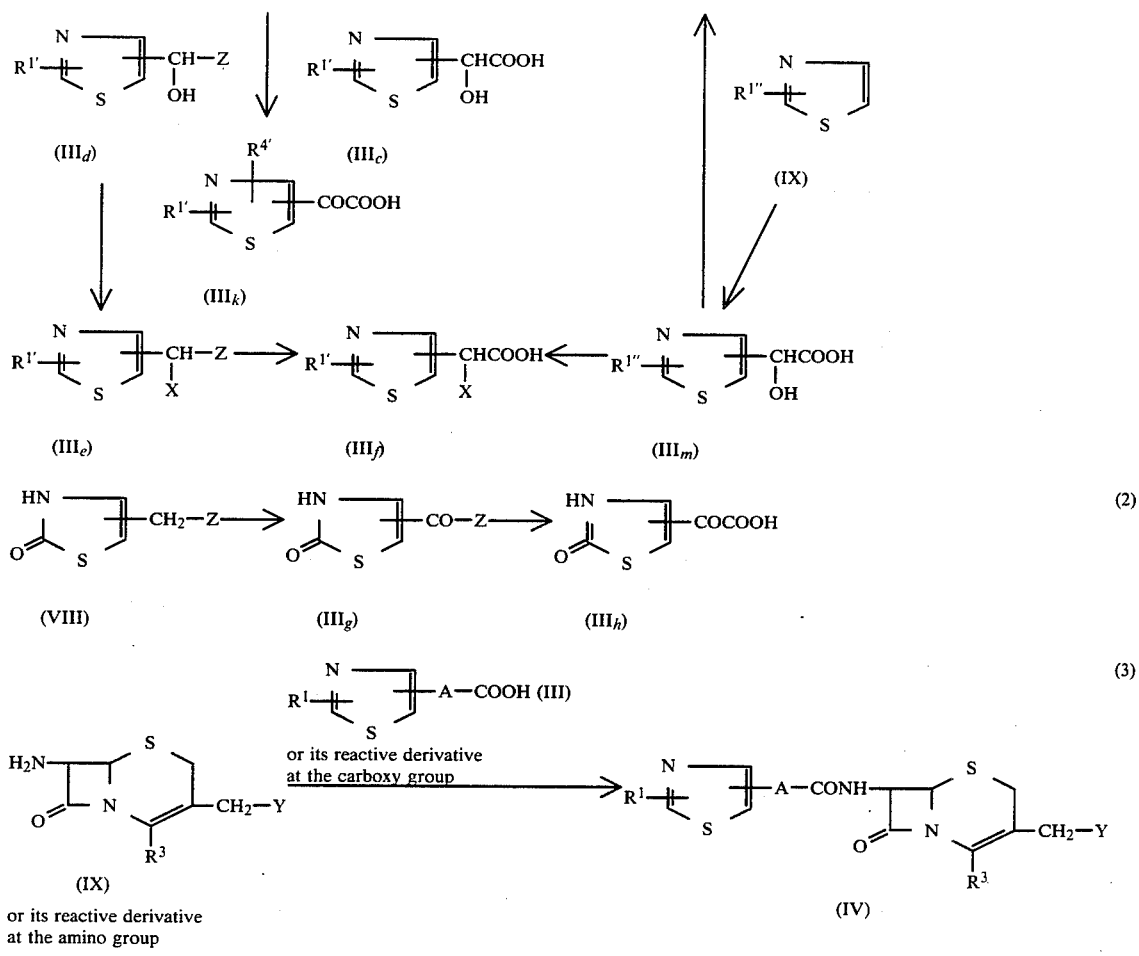

wherein
R$^1$, R$^{1'}$, R$^{1''}$, R$^3$, R$^4$, A and Y are each as defined above,
R$^{4'}$ is halogen,
X is a protected hydroxy and
Z is a protected carboxy.

Regarding the object compounds (I) and (Ia)–(Ig) and the starting compounds (III), (IIIa)–(IIIm), (IV) and (VI)–(VIII), it is to be understood that they include tautomeric isomers, That is, in case that the group of the formula:

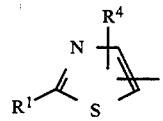

(provided that R$^1$ is amino, lower alkylamino, protected amino or hydroxy, and R$^4$ is as defined above) in the formula of said object and starting compounds take the formula:

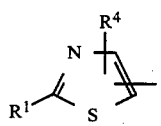

(R$^1$ and R$^4$ are each as defined above), said group of the formula:

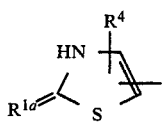

can also alternatively represented by its tautomeric formula:

(R$^{1a}$ is imino, lower alkylimino, a protected imino or oxo, and R$^4$ is as defined above). That is, both of the said groups are in the state of equilibrium and such tautomerism can be represented by the following equilibrium.

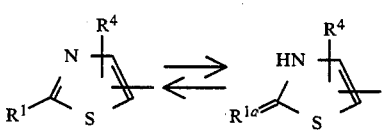

These types of tautomerism of the amino- and hydroxy-thiazole compounds as stated above have been well known in the literature, and it is obvious to be any person skilled in the arts that both of the tautomeric isomers are easily convertible reciprocally and are included within the same category of the compound per se. Accordingly, the both of the tautomeric forms of the object compounds (I) and (I$_a$)–(I$_g$) and the starting compounds (III), (III$_a$)–(III$_m$), (IV) and (VI)–(VIII) are clearly included within the scope of the present invention. In the present specification, the object and starting compounds including the group of such tautomeric isomers are represented by using one of the expressions therefor, that is the formula:

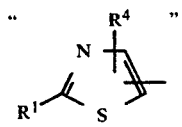

only for the convenient sake.

Suitable pharmaceutically acceptable salt of the object 3,7-disubstituted-3-cephem-4-carboxylic acid compounds (I) are conventional non-toxic salts and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g, arginine, aspartic acid, glutamic acid, etc.), and the like.

In the above and subsequent descriptions of the present specification, suitable examples and illustrations of the various definitions which the present invention intend to include within the scope thereof are explained in details as follows.

The term "lower" is intended to mean 1 to 6 carbon atoms.

Suitable lower alkyl moiety in the terms "lower alkylamino" and "a protected lower alkylamino" may include methyl, ethyl, propyl, isopropyl, butyl, isobutyl, pentyl, hexyl and the like.

Suitable protective group in the terms "a protected amino" and "a protected lower alkylamino" may include an acyl and a conventional protective group other than the acyl group such as benzyl and the like.

Suitable protected hydroxy moiety in the term "a protected hydroxy(lower)alkylene" may include an acyloxy and hydroxy group substituted by a conventional protective group other than the acyl group such as tetrahydropyranyloxy and the like.

Suitable acyl and acyl moiety in the term "acyloxy" as mentioned above may include carbamoyl, thiocarbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.); lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.), and the like. The acyl moiety as stated above may have one to ten suitable substituent(s) such as halogen (e.g., chlorine, bromine, iodine or fluorine), cyano, lower alkyl (e.g., methyl, ethyl, propyl, isopropyl, butyl, etc.), lower alkenyl (e.g., vinyl, allyl, etc.), or the like, suitable examples of which may be mono(or di or tri)halo(lower)alkanoyl (e.g., trifluoroacetyl, etc.).

Suitable lower alkoxy may include methoxy, ethoxy, propoxy, isopropoxy, butoxy, pentyloxy and the like.

Suitable heterocyclic group in the term "a heterocyclic-thio group which may have suitable substituent(s)" means saturated or unsaturated, monocyclic or polycyclic heterocyclic group containing at least one heteroatom such as an oxygen, sulfur, nitrogen atom and the like.

And, especially preferable heterocyclic group may be N-containing heterocyclic group such as unsaturated 3 to 3-membered heteromonocyclic group containing 1 to 4 nitrogen atom(s), for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; saturated 3 to 8-membered heteromonocyclic group containing 1 to 4 nitrogen atom(s) (e.g., pyrrolidinyl, imidazolidinyl, piperidino, piperazinyl, etc.);

unsaturated condensed heterocyclic group containing 1 to 4 nitrogen atom(s) (e.g., indolyl, isoindolyl, indolizynyl, benzimidazolyl, quinolyl, isoquinolyl, indazolyl, benzotriazolyl, etc.); unsaturated 3- to 8-membered heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered heteromonocyclic group containing 1 to 2 oxygen atom(s) and 1 to 3 nitrogen atom(s) (e.g., morpholinyl, etc.); unsaturated condensed heterocyclic group containing 1 to 2 oxygen atom(s) and 1 to 3 nitrogen atom(s) (e.g., benzoxazolyl, benzoxadiazolyl, etc.);

unsaturated 3 to 8-membered heteromonocyclic group containing 1 to 2 sulfur atom(s) and 1 to 3 nitrogen atom(s), for example, thiazolyl, thiadiazolyl (e.g., 1,2,4-thiadiazolyl, 1,3,4-thiadiazolyl, 1,2,5-thiadiazolyl, etc.), etc.;

unsaturated 3 to 8-membered heteromonocylic group containing 1 to 2 sulfur atom(s) and 1 to 3 nitrogen atom(s) (e.g., thiazolidinyl, etc.);

unsaturated condensed heterocyclic group containing 1 to 2 sulfur atom(s) and 1 to 3 nitrogen atom(s) (e.g., benzothiazolyl, benzothiadiazolyl, etc.) and the like, wherein said heterocyclic group may have one to four suitable substituent(s) such as lower alkyl (e.g., methyl, ethyl, propyl, isopropyl, butyl, isobutyl, pentyl, cyclopentyl, hexyl, cyclohexyl, etc.); lower alkenyl (e.g., vinyl, allyl, butenyl, etc.); aryl (e.g., phenyl, tolyl, etc.); halogen (e.g., chlorine, bromine, iodine or fluorine); amino and the like.

Suitable carboxy derivative may include —COO$^-$ and a protected carboxy such as carboxylic ester or the like.

Suitable examples of said ester may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.); lower alkenyl ester (e.g., vinyl ester, allyl ester etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, etc.);

lower alkanesulfonyl(lower)alkyl ester (e.g., 2-mesylethyl ester etc.); phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g., phenyl ester, tolyl ester, tertiarybutylphenyl ester, xylyl ester, mesityl ester, cumenyl ester, etc.), and the like.

Suitable lower alkylene moiety in the terms "hydroxy(lower)alkylene" and "a protected hydroxy(lower)alkylene" may include, methylene, ethylene, trimethylene, propylene, tetramethylene and the like, among which the preferable hydroxy(lower)alkylene and protected hydroxy(lower)alkylene may be hydroxy ($C_{1-2}$) alkylene and a protected hydroxy ($C_{1-2}$) alkylene, and the most preferable ones are hydroxymethylene and a protected hydroxy methylene.

Suitable "a conventional group which is capable to be replaced by the residue of a compound of the formula: H—$R^{2'''}$" in the symbol Y may include a halogen atom (e.g., chlorine, bromine, etc.), azido group, an acyloxy group such as lower alkanoyloxy (e.g., formyloxy, acetoxy, propionyloxy, butyryloxy, etc.) and aroyloxy (e.g., benzoyloxy, toluoyloxy, etc.), and the like.

Suitable halogen may include the same ones as aforementioned.

Suitable "a protected carboxy" may include an ester as aforementioned.

The various processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethyl-formamide, pyridine or any other organic solvent which does not adversely influence to the reaction. Among these solvents, hydrophilic solvents may be used in a mixture with water.

When the compound (III) is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N-diethylcarbodiimide, N,N-diisopropylcarbodiimide, N-ethyl-N'(3-dimethylaminopropyl)carbodiimide, N,N-carbonylbis-(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)-isoxazolium hydroxide intramolecular salt, (chloromethylene)-dimethylammonium chloride, 1-(p-chlorobenzenesulfonyloxy)-6-chloro-1H-benzotriazole, or the like.

The reaction may be also carried out in the presence of an inorganic or an organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at room temperature.

The present invention includes, within its scope, the case that the free hydroxy group is transformed into the formyloxy group during the reaction.

Process 2

The object compound ($I_a$) or a salt thereof can be prepared by reacting the compound (IV) or a salt thereof with the compound (V) or its reactive derivative at the mercapto group.

The starting compound (IV) to be used in the present process can be prepared by reacting the compound (IX) or its reactive derivative at the amino group or a salt thereof with the compound (III) or its reactive derivative at the carboxy group. The reaction conditions for preparing the starting compound (IV) are substantially same as those for preparing the compound (I) as stated in the explanation of Process 1, and therefore the details of the reaction condition is to be referred to the explanation of Process 1 by reading "the compound (II)" as "the compound (IX)" for the convenient sake. That is, suitable reactive derivative at the amino group of the compound (IX) is the same as that of the compound (II), suitable salt of the compound (IX) is the same as that of the compound (II). And the reaction conditions, solvents, reaction temperature, etc. also are the same as those used in Process 1.

Suitable reactive derivative at the mercapto group of the compound (V) may include a metal salt such as an alkali metal salt (e.g., sodium salt, potassium salt, etc.), an alkaline earth metal salt (e.g., magnesium salt, etc.) or the like. The reaction of the compound (IV) or a salt thereof with the compound (V) or its reactive derivative at the mercapto group may be preferably carried out in a solvent such as water, acetone, chloroform, nitrobenzene, dimethylformamide, methanol, ethanol, dimethylsulfoxide, or any other organic solvents which do not adversely influence to the reaction, preferably in a rather high polar solvent. Among these solvents, hydrophilic solvents may be used in a mixture with water. The reaction is preferably carried out in around neutral medium. When the compound (IV) or the compound (V) is used in a free from, the reaction is preferably conducted in the presence of a base such as alkali metal hydroxide, alkali metal carbonate, alkali metal bicarbonate, trialkylamine, or the like. The reaction temperature is not critical, and the reaction is usually carried out at room temperature or slightly elevated temperature.

The present invention may include, within its scope, the cases that the protected amino group and/or the protected hydroxy group and/or the carboxy derivative are transformed into the corresponding free amino group and/or hydroxy group and/or carboxy group during the reaction or post-treating in the present reaction.

Process 3

The object compound ($I_b$) or a salt thereof can be prepared by subjecting the compound (Ic) or a salt thereof to elimination reaction of the protective group of the amino.

The present elimination reaction is carried out in accordance with a conventional method such as hydrolysis, reduction, or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as alkoxycarbonyl (e.g., tert-pentyloxycarbonyl, etc.), substituted alkoxycarbonyl, aralkoxycarbonyl (e.g., benzyloxycarbonyl, etc.), substituted aralkoxycarbonyl, trityl, substituted phenylthio, substituted aralkylidene, substituted alkylidene, substituted cycloalkylidene or the like. Suitable acid may include, for example, formic acid, trifluoroacetic acid, benzenesulfonic acid, p-toluenesulfonic acid and the like, and the most suitable acid is an acid which can be easily removed from the reaction mixture by a conventional manner such as distillation under reduced pressure, for example, formic acid, trifluoroacetic acid, etc. The acid suitable for the reaction can be selected according to the kind of protective group to be eliminated. When the elimination reaction is conducted with the acid, it can be carried out in the presence or absence of a solvent. Suitable solvent may include a hydrophilic organic solvent, water or a mixed solvent thereof. The hydrolysis using hydrazine is commonly applied for eliminating the protective group, for example, phthaloyl.

The reductive elimination is generally applied for eliminating the protective group, for example, trichloroethoxycarbonyl, benzyloxycarbonyl, substituted benzyloxycarbonyl, 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metallic compound (e.g., chromous chloride, chromous acetate, etc.) and an organic or inorganic acid (e.g. acetic acid, propionic acid, hydrochloric acid, etc.); and catalytic reduction. Suitable catalyst used for catalytic reduction may include, for example, Raney nickel, platinum oxide, palladium carbon and other conventional catalysts.

Among the protective groups, the acyl group can be generally eliminated by hydrolysis as mentioned above or by the other conventional hydrolysis. Especially, trifluoroacetyl group can be easily eliminated by treating with water in the presence or absence of the base, and halogen substituted-alkoxycarbonyl and 8-quinolyloxycarbonyl groups are usually eliminated by treating with a heavy metal such as copper, zinc, or the like.

The reaction temperature is not critical and may be suitably selected in accordance with the kind of the protective group for the amino group and the elimination method as mentioned above, and the present reaction is preferably carried out under a mild condition such as under cooling or slightly elevated temperature.

The present invention includes, within its scope, the cases that the carboxy derivative is transformed into the free carboxy group and/or the protected hydroxy group is transformed into the free hydroxy group during the reaction or post-treating in the present invention.

Process 4

The object compound ($I_d$) or a salt thereof can be prepared by subjecting the compound (Ie) or a salt thereof to elimination reaction of the protective group of the hydroxy.

The present elimination reaction is carried out in accordance with a conventional method such as hydrolysis, reduction or the like. The hydrolysis may include a method using an acid or base and the like. These methods may be selected depending on kind of the protective groups to be eliminated.

The hydrolysis using an acid is one of the most common and preferable methods for eliminating the protective groups such as tetrahydropyranyl, benzyloxycarbonyl, substituted benzyloxycarbonyl, alkoxycarbonyl, substituted alkoxycarbonyl, adamantyloxycarbonyl, trityl, substituted phenylthio, substituted aralkylidene, substituted alkylidene, substituted cycloalkylidene or the like. Suitable acid may include, for example, formic acid, trifluoroacetic acid, benzenesulfonic acid, p-toluenesulfonic acid, hydrochloric acid, and the like. The acid suitable for the reaction can be selected according to the potective group to be eliminated and other factors. The hydrolysis using an acid may be carried out in the presence of a solvent, such as a hydrophilic organic solvent, water or a mixed solvent thereof.

The hydrolysis with a base is preferably applied for eliminating acyl group. Suitable base may include, for example, an inorganic base such as alkali metal (e.g., sodium, potassium, etc.), alkaline earth metal (e.g., magnesium, calcium, etc.), the hydroxide or carbonate or bicarbonate thereof or the like, and an organic base such as trialkylamine (e.g., trimethylamine, triethylamine, etc.), picoline, N-methylpyrrolidine, N-methyl-morpholine, 1,5-diazabicyclo[4,3,0]non-5-ene, 1,4-diazabicyclo[2,2,2]octane, 1,8-diazabicyclo[5,4,0]undecene-7 or the like. The hydrolysis using a base is often carried out in water or a hydrophilic organic solvent or a mixed solvent thereof.

The reduction is generally applied for eliminating, for example, trichloroethoxycarbonyl, benzyloxycarbonyl, substituted benzyloxycarbonyl, 2-pyridylmethoxycarbonyl, etc.

The reduction applicable for the elimination reaction of the present invention may include, for example, reduction using a metal (e.g., tin, zinc, iron, etc.) or a combination of metallic compound (e.g., chromous chloride, chromous acetate, etc.) and an organic or inorganic acid (e.g., acetic acid, propionic acid, hydrochloric acid, etc.); and reduction in the presence of a metallic catalyst for catalytic reduction. Suitable metallic catalyst for catalytic reduction may include, for example, Raney-nickel, platinum oxide, palladium carbon and other conventional catalysts.

When the protective group is acyl, the acyl can be generally eliminated by hydrolysis as mentioned above or by other conventional hydrolysis.

Especially, trifluoroacetyl can be usually eliminated by treating with water in the presence or absence of the base, and halogen substituted-alkoxycarbonyl and 8-quinolyloxycarbonyl are usually eliminated by treating with a heavy metal such as copper, lead, zinc, etc.

The reaction temperature is not critical and may be suitably selected in accordance with the kind of the protective group and the elimination method, and the present reaction is preferably carried out under a mild condition such as under cooling or slightly warming.

The present invention includes, within its scope, the cases that the carboxy derivative is transformed into the free carboxy group and/or the protected amino group is transformed into the free amino group during the reaction or post-treating in the present reaction.

Process 5

The object compound (If) or a salt thereof can be prepared by reducing the compound (Ig) or a salt thereof.

The present reduction is conducted by a conventional method such as a method of using an alkali metal borohydride (e.g., sodium borohydride, potassium borohydride, etc.) or the like.

The present reduction is usually carried out in a solvent which does not adversely influence to the reaction, for example, water, methanol, ethanol, tetrahydrofuran, dioxane and the like. The present reduction can be also carried out in the presence of an inorganic or an organic base such as an alkali metal (e.g., sodium, potassium, etc.), an alkaline earth metal (e.g., magnesium, calcium, etc.), the hydroxide or carbonate or bicarbonate thereof, tri(lower)alkylamine (e.g., trimethylamine, triethylamine, etc.), picoline, N-methylpyrrolidine, N-methylmorpholine, 1,5-diazabicyclo[4,3,0]none-5-ene, 1,4-diazabicyclo[2,2,2]octane, 1,8-diazabicyclo[5,4,0]undecene-7, or the like.

The reaction temperature is not critical and the present reaction is preferably carried out under a mild condition such as under cooling or slightly warming.

Processes for preparing the starting compounds (III) are explained in details as follows.

The starting compounds (III$_c$) can be prepared by reducing the compound (III$_b$) and the starting compound (IIId) can be prepared by reducing the compound (III$_a$), respectively. The reaction method, i.e. reduction and the reaction conditions, i.e. solvent, reaction temperature, etc. are the same as those used in the reaction of Process 5, and therefore the details therefor is to be referred to the explanation for the Process 5.

The compound (VII) can be prepared by reacting the compound (VI) or its reactive derivative at the amino group or a salt thereof with an amino-protecting agent, and the starting compound (IIIa) can be prepared by reacting the compound (IIIi) or its reactive derivative at the amino group or a salt thereof with an amino-protecting agent, and the starting compound (IIIb) can be prepared by reacting the compound (III$_1$) or its reactive derivative at the amino group or a salt thereof with an amino-protecting agent, and the starting compound (IIIf) can be prepared by reacting the compound (IIIm) or its reactive derivative at the amino group or a salt thereof with an amino-protecting agent, respectively.

Suitable reactive derivative at the amino group of the compounds (VI), (IIIi), (III$_1$) and (IIIm) and suitable salt of the compounds (VI), (IIIi), (III$_1$) and (IIIm) may include the same ones as illustrated in the explanations of reactive derivative at the amino group of the compound (II) or (IX) and salt of the compound (II) or (IX), respectively.

Suitable amino-protecting agent may include acylating agent which may include an aliphatic, aromatic and heterocyclic isocyanate, and the corresponding isothiocyanate, and an aliphatic, aromatic and heterocyclic carboxylic acid, and the corresponding sulfonic acid, carbonic acid ester and carbamic acid, and the corresponding thio acid, and the reactive derivative of the above acids.

Suitable reactive derivative of the above acids may include the same ones as illustrated in the explanation of "reactive derivative at the carboxy group of the compound (III)". The example of the protective group (e.g. acyl group) to be introduced into the amino group in the compounds (VI), (IIIi), (III₁) and (IIIm) by the above amino-protecting agent (e.g. acylating agent) may be the same protective group (e.g. acyl group) as illustrated in the explanation of the protective group in the terms "a protected amino" and "a protected lower alkylamino".

The present reaction (e.g. acylating reaction) is carried out in the similar manner as illustrated in the reaction of the compound (II) or its reactive derivative at the amino group or a salt thereof with the compound (III) or its reactive derivative at the carboxy group.

The starting compound ($III_a$) can be prepared by oxidizing the compound (VII), and the starting compound ($III_g$) can be prepared by oxidizing the compound (VIII).

The present oxidation reaction is conducted by a conventional method which is applied for the transformation of so-called activated methylene group into carbonyl group. That is, the present oxidation is conducted by a conventional method such as oxidation by using a conventional oxidizing agent such as selenium dioxide, trivalent manganese compound (e.g. manganous acetate and potassium permanganate, etc.) or the like. The present oxidation is usually carried out in a solvent which does not adversely influence to the reaction, for example, water, dioxane, tetrahydrofuran, and the like.

The reaction temperature is not critical and the reaction is preferably carried out under warming to heating.

The starting compound ($III_b$) can be prepared by subjecting the compound ($III_a$) to elimination reaction of the protective group of the carboxy, the starting compound ($III_f$) can be prepared by subjecting the compound ($III_e$) to elimination reaction of the protective group of the carboxy, and the starting compound ($III_h$) can be prepared by subjecting the compound ($III_g$) to elimination reaction of the protective group of the carboxy, and the starting compound (IIIk) can be prepared by subjecting the compound (IIIj) to elimination reaction of the protective group of the carboxy, respectively.

In the present elimination reaction, all conventional methods used in the elimination reaction of the protected carboxy, for example, hydrolysis, reduction, etc. can be applicable. When the protective group is an ester, it can be eliminated by hydrolysis. The hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo-[2,2,2]octane, 1,8-diazabicyclo[5,4,0]undecene-7, or the like. Suitable acid may include an organic acid (e.g., formic acid, acetic acid, propionic acid, etc.) and an inorganic acid (e.g., hydrochloric acid, hydrobromic acid, sulfuric acid, etc.). The reduction can be applicable for elimination of the protective group such as 2-iodoethyl ester, 2,2,2-trichloroethyl ester, or the like. The reduction applicable for the elimination reaction of the present invention may include, for example, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and reduction in the presence of a metallic catalytic reduction. The metallic catalysts for catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), and the like.

The reaction temperature is not critical, and it may be suitably selected in accordance with the kind of the protective group of the carboxy and the elimination method.

The starting compound ($III_e$) can be prepared by reacting the compound ($III_d$) with a hydroxy-protecting agent. As the hydroxy-protecting agent, there may be used a conventional hydroxy-protecting agent which is capable of introducing a protective group as illustrated hereinabove into hydroxy to give a protected hydroxy. Suitable hydroxy-protecting agent may include, for example, an acylating agent including the same as illustrated in the explanation of the acylating agent in the amino-protecting agent, an olefinic heterocyclic compound (e.g. 3,4-dihydro-2H-pyrane, etc.), and the like. The example of the acyl group to be introduced into the hydroxy group in the compound ($III_d$) by the above acylating agent may be the same as illustrated in the explanation of the acyl moiety in the term "acyloxy".

The present reaction using an olefinic heterocyclic compound is preferably carried out in the presence of an acidic catalyst such as p-toluenesulfonic acid, hydrochloric acid, phosphorus oxychloride, or the like. The present reaction is usually carried out in a solvent which does not adversely influence to the reaction, for example, ethyl acetate, tetrahydrofuran, dioxane, and the like under anhydrous condition.

The reaction temperature is not critical, and the present reaction proceeds sufficiently under cooling or at room temperature.

The starting compound (IIIi) and its salt can be prepared by subjecting the compound (IIIa) to elimination reaction of the protective group of the amino.

The present elimination reaction is carried out in the similar manner to that illustrated in the elimination reaction of Process 3.

The starting compound (IIIj) can be prepared by reacting the compound (IIIa) with a halogenating agent.

Suitable halogenating agent may include halogen (e.g., chlorine, bromine, etc.), trihaloisocyanuric acid (e.g., trichloroisocyanuric acid, etc.), N-halosuccinimide (e.g., N-chlorosuccinimide, N-bromosuccinimide, etc.) and the like.

The present reaction is usually carried out in a solvent which does not adversely influence to the reaction, for example, dimethylformamide, dioxane, acetic acid and the like.

The reaction temperature is not critical and the reaction is preferably carried out at ambient temperature or under warming to heating.

The starting compound (IIIm) can be prepared by reacting the compound (IX) with glyoxylic acid.

The present reaction is usually carried out in a solvent which does not adversely influence to the reaction, for example, water, acetone, dioxane, acetonitrile, methylene chloride, dimethylformamide and the like.

The present reaction is preferably conducted in the presence of a base such as alkali metal hydroxide, alkali metal carbonate, alkali metal bicarbonate and the like.

The reaction temperature is not critical and the reaction is preferably carried out under warming to heating.

The starting compound (IIII) can be prepared by oxidizing the compound (IIIm).

The present oxidation reaction is conducted by a conventional method which is applied for the transformation of hydroxymethylene group into carbonyl group. That is, the present oxidation is conducted by a conventional method such as oxidation by using a conventional oxidizing agent such as manganese dioxide or the like. The present oxidation is usually carried out in a solvent which does not adversely influence to the reaction, for example, water, dioxane, tetrahydrofuran and the like.

The reaction temperature is not critical and the reaction is preferably carried out under warming to heating.

In the aforementioned reactions and/or the post-treating of the reactions of the present invention, the aforementioned tautomeric isomers may be occasionally transformed into the other tautomeric isomers, and such cases are also included in the scope of the present invention.

In case that the object compound (I) is obtained in a form of the free acid at 4 position and/or in case that the object compound (I) has free amino group, it may be transformed into its pharmaceutically acceptable salt as aforementioned by a conventional method.

The object compounds (I) of the present invention exhibit high antibacterial activity and inhibit the growth of a number of microorganisms including Gram-positive and Gram-negative bacteria. For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsules, tablet, dragees, ointments or suppositories, or in liquid form such as solutions, suspensions, or emulsions. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 50 mg., 100 mg., 250 mg., and 500 mg. of the compounds according to the present invention has proved to be effective in treating diseases caused by bacterial infection. In general amounts between 1 mg. and about 1000 mg. or even more may be administered.

Now, in order to show the utility of the object compounds, test data on anti-microbial activity of some representative compounds of the present invention are shown below.

Test compounds (1) 3-(1-Methyl-1H-tetrazol-5-yl)thiomethyl-7-[2-(2-amino-1,3-thiazol-4-yl)glyoxylamido]-3-cephem-4-carboxylic acid, which can be represented as 3-(1-methyl-1H-tetrazol-5-yl)thiomethyl-7-[2-(2-imino-2,3-dihydro-1,3-thiazol-4-yl)glyoxylamido]-3-cephem-4-carboxylic acid.

(2) 3-(1,3,4-Thiadiazol-2-yl)thiomethyl-7-[2-(2-amino-1,3-thiazol-4-yl)glyoxylamido]-3-cephem-4-carboxylic acid, which can be represented as 3-(1,3,4-thiadiazol-2-yl)thiomethyl-7-[2-(2-imino-2,3-dihydro-1,3-thiazol-4-yl)glyoxylamido]-3-cephem-4-carboxylic acid.

(3) 3-(5-Methyl-1,3,4-thiadiazol-2-yl)thiomethyl-7-[2-(2-amino-1,3-thiazol-4-yl)glyoxylamido]-3-cephem-4-carboxylic acid, which can be represented as 3-(5-methyl-1,3,4-thiadiazol-2-yl)thiomethyl-7-[2-(2-imino-2,3-dihydro-1,3-thiazol-4-yl)glyoxylamido]-3-cephem-4-carboxylic acid.

(4) 3-(5-Methyl-1,3,4-oxadiazol-2-yl)thiomethyl-7-[2-(2-amino-1,3-thiazol-4-yl)glyoxylamido]-3-cephem-4-carboxylic acid, which can be represented as 3-(5-methyl-1,3,4-oxadiazol-2-yl)thiomethyl-7-[2-(2-imino-2,3-dihydro-1,3-thiazol-4-yl)-glyoxylamido]-3-cephem-4-carboxylic acid.

(5) 3-(4-Methyl-4H-1,2,4-triazol-3-yl)thiomethyl-7-[2-(2-amino-1,3-thiazol-4-yl)glyoxylamido]-3-cephem-4-carboxylic acid, which can be represented as 3-(4-methyl-4H-1,2,4-triazol-3-yl)thiomethyl-7-[2-(2-imino-2,3-dihydro-1,3-thiazol-4-yl)-glyoxylamido]-3-cephem-4-carboxylic acid.

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu g/ml$. after incubation at 37° C. for 20 hours.

Test results

| | MIC ($\mu g/ml.$) Test compounds | | | | |
|---|---|---|---|---|---|
| Test Bacteria | (1) | (2) | (3) | (4) | (5) |
| E. Coli 324 | 0.05 | 0.05 | 0.05 | 0.05 | 0.05 |

The following examples are given for the purpose of illustrating the present invention:

PREPARATION OF THE STARTING COMPOUNDS (1) Preparation of 2-(2-tert-pentyloxycarbonylamino-1,3-thiazol-4-yl)glyoxylic acid which can be represented as 2-(2-tert-pentyloxycarbonylimino-2,3-dihydro-1,3-thiazol-4-yl)-glyoxylic acid To a solution of ethyl 2-(2-amino-1,3-thiazol-4-yl)-acetate, which can be represented as ethyl 2-(2-imino-2,3-dihydro-1,3-thiazol-4-yl)acetate, (14 g.) in a mixture of pyridine (40 g.) and methylene chloride (300 ml.) was gradually added diethyl ether solution of tert-pentyl chloroformate (70 ml.) containing 0.35 mole of tert-pentyl chloroformate over 10 minutes at −20° C. with stirring, and the mixture was stirred for 2 hours at the same temperature and further stirred for 0.5 hour at 0° C. After the reaction, the reaction mixture was poured into water (200 ml.), and then the organic layer was separated. The organic layer was washed with 2N hydrochloric acid, water, 5% sodium bicarbonate aqueous solution and water in turn and then dried over magnesium sulfate. The solvent was distilled off from the organic layer to give dark brown oil of ethyl 2-(2-tertpentyloxycarbnylamino-1,3-thiazol-4-yl)acetate, which can be represented as ethyl 2-(2-tert-pentyloxycarbonylimino-2,3-dihydro-1,3-thiazol-4-yl)acetate, (12 g.).

I.R. Spectrum (liquid): 1667, 1660 (CO) cm$^{-1}$,

N.M.R. Spectrum (CDCl$_3$, δ): 3.75 (2H, s), 6.75 (1H, s).

To a solution of selenium dioxide (0.11 g.) in a mixture of dioxane (2.5 ml.) and water (0.1 ml.) was added a mixture of ethyl 2-(2-tert-pentyloxycarbonylamino-1,3-thiazol-4-yl)acetate, which can be represented as ethyl 2-(tert-pentyloxycarbonylimino-2,3-dihydro-1,3-thiazol-4-yl)acetate, (0.3 g.) and dioxane (2.5 ml.) at 110° C. with stirring. The mixture was stirred for 30 minutes at the same temperature, and selenium dioxide (0.055 g.) was further added thereto and then the mixture was stirred for 1.5 hours at the same temperature. After the reaction, the reaction liquid is separated by decantation, and the residue was washed with a small amount of dioxane. The reaction liquid and washing are combined together, and then the solvents were distilled off. The residue was dissolved in ethyl acetate. The solution was washed with water and dried and then the solvent was distilled off to give brown oil of ethyl 2-(2-tert-pentyloxycarbonylamino-1,3-thiazol-4-yl)glyoxylate, which can be represented as ethyl 2-(tert-pentyloxycarbonylimino-2,3-dihydro-1,3-thiazol-4-yl)-glyoxylate, (0.22 g.).

I.R. Spectrum (liquid): 1720, 1690 (CO) cm$^{-1}$,

N.M.R. Spectrum (COCl$_3$, δ): 8.3 (1H, s).

A mixture of ethyl 2-(2-tert-pentyloxycarbonylamino-1,3-thiazol-4-yl)glyoxylate, which can be represented as ethyl 2-(2-tert-pentyloxycarbonylimino-2,3-dihydro-1,3-thiazol-4-yl)-glyoxylate, (2.8 g.) and ethanol (10 ml.) was mixed with a solution of sodium hydroxide (0.54 g.) in water (20 ml.), and the mixture was stirred for 1 hour at room temperature. After the reaction, a small amount of ethanol was distilled off. The remaining reaction mixture was washed with diethyl ether and then the aqueous layer was separated therefrom. To the aqueous layer was added ethyl acetate, and the mixture was adjusted to pH 1 to 2 with 10% hydrochloric acid and then the ethyl acetate layer was separated therefrom. The ethyl acetate layer was washed with a saturated aqueous solution of sodium chloride, dried over magnesium sulfate and then treated with activated charcoal. The solvent was distilled off from the ethyl acetate layer to give yellow brown powder of 2-(2-tert-pentyloxycarbonylamino-1,3-thiazol-4-yl)glyoxylic acid, which can be represented as 2-(2-tert-pentyloxycarbonylimino-2,3-dihydro-1,3-thiazol-4-yl)glyoxylic acid, (1.75 g.).

I.R. Spectrum (Nujol): 1730, 1680 (CO) cm$^{-1}$,

N.M.R. Spectrum (d$_6$-dimethylsulfoxide, δ): 8.4 (1H, s).

(2) Preparation of
2-hydroxy-2-(2-tert-pentyloxycarbonylamino-1,3-thiazol-4-yl)acetic acid which can be represented as
2-hydroxy-2-(2-tert-pentyloxycarbonylimino-2,3-dihydro-1,3-thiazol-4-yl)acetic acid To a mixture of 2-(2-tert-pentyloxycarbonylamino-1,3-thiazol-4-yl)glyoxylic acid, which can be represented as 2-(2-tert-pentyloxycarbonylimino-2,3-dihydro-1,3-thiazol-4-yl)glyoxylic acid, (1.7 g.), sodium bicarbonate (0.5 g.), ethanol (10 ml.) and water (10 ml.) was added sodium borohydride (0.23 g.) under stirring and ice-cooling, and then the mixture was stirred for 1 hour at the same temperature. After the reaction, the reaction mixture was concentrated slightly. To the remaining reaction mixture were added 1N sodium hydroxide aqueous solution (6 ml.) and diethyl ether (20 ml.), and then the aqueous layer was separated. To the aqueous layer was added ethyl acetate, and the mixture was adjusted to pH 1 to 2 with 10% hydrochloric acid and then the ethyl acetate layer was separated therefrom. The ethyl acetate layer was washed with a saturated aqueous solution of sodium chloride, dried over magnesium sulfate and then treated with activated charcoal. The solvent was distilled off from the ethyl acetate layer to give brown powder of 2-hydroxy-2-(2-tert-pentyloxycarbonylamino-1,3-thiazol-4-yl)acetic acid, which can be represented as 2-hydroxy-2-(2-tert-pentyloxycarbonylimino-2,3-dihydro-1,3-thiazol-4-yl)acetic acid, (1.5 g.).

I.R. Spectrum (Nujol): 1690–1740 (CO) cm$^{-1}$,

N.M.R. Spectrum (d$_6$-dimethylsulfoxide, δ): 5.0 (1H, s), 7.05 (1H, s).

(3) Preparation of
2-(2-oxo-2,3-dihydro-1,3-thiazol-4-yl)glyoxylic acid
which can be represented as
2-(2-hydroxy-1,3-thiazol-4-yl)glyoxylic acid To a solution prepared by heating a mixture of selenium dioxide (0.33 g.), dioxane (15 ml.) and water (0.3 ml.) at 110° C. with stirring was added ethyl 2-(2-oxo-2,3-dihydro-1,3-thiazol-4-yl)acetate, which can be represented as ethyl 2-(2-hydroxy-1,3-thiazol-4-yl)acetate, (0.56 g.) without heating, and then the mixture was stirred for 30 minutes at 110° C. After the reaction, the reaction liquid was separated and the residue was washed with a small amount of dioxane. The reaction liquid and the washings were combined together, and the solvents were distilled off. To the residue was added ethyl acetate, and the mixture was washed with water and dried over magnesium sulfate. The solvent was distilled off from the mixture to give a solid of ethyl 2-(2-oxo-2,3-dihydro-1,3-thiazol-4-yl)-glyoxylate, which can be represented as ethyl 2-(2-hydroxy-1,3-thiazol-4-yl)glyoxylate, (0.55 g.)

I.R. Spectrum (Nujol): 1720, 1630–1680 (CO) cm$^{-1}$,

N.M. R. Spectrum (CDCl$_3$, δ):
7.96 (1H, s).

A mixture of ethyl 2-(2-oxo-2,3-dihydro-1,3-thiazol-4-yl)glyoxylate, which can be represented as ethyl 2-(2-hydroxy-1,3-thiazol-4-yl)glyoxylate, (1.45 g.) and 1N sodium hydroxide aqueous solution (21 ml.) was allowed to stand for 30 minutes at room temperature. After the reaction, the reaction mixture was washed with diethyl ether and then adjusted to pH 1 with 10% hydrochloric acid. The precipitates were collected by filtration, washed with water and diethyl ether and dried to give powder of 2-(2-oxo-2,3-dihydro-1,3-thiazol-4-yl)glyoxylic acid, which can be represented as 2-(2-hydroxy-1,3-thiazol-4-yl)glyoxylic acid, (0.30 g.). On the other hand, the filtration was extracted with ethyl acetate, and the ethyl acetate was distilled off from the extract to give the same object compound (0.40 g.).

I.R. Spectrum (Nujol): 1740, 1660, 1620 (CO) cm$^{-1}$, (4) Preparation of
2-(2-propanesulfonylamino-1,3-thiazol-4-yl)glyoxylic
acid which can be represented as
2-(2-propanesulfonylimino-2,3-dihydro-1,3-thiazol-4-yl)glyoxylic acid A mixture of ethyl 2-(2-amino-1,3-thiazol-4-yl)acetate, which can be represented as ethyl 2-(2-imino-2,3-dihydro-1,3-thiazol-4-yl)acetate, (40 g.) and pyridine (200 ml.) was stirred in a stream of nitrogen gas at 40° C., and to the mixture was dropwise added a mixture of propanesulfonyl chloride (61.3 g.) and methylene chloride (100 ml.) over 2 hours, and then the mixture was stirred for 2 hours at the same temperature. After the reaction, pyridine and methylene chloride were distilled off from the reaction mixture. The residue was dissolved in ethyl acetate, and the solution was washed with water, ½N hydrochloric acid and water in turn and then dried. The ethyl acetate was distilled off from the solution, and the residue was washed with a mixture of ethyl acetate and diethyl ether and then dried to give ethyl 2-(2-propanesulfonylamino-1,3-thiazol-4-yl)acetate, which can be represented as ethyl 2-(2-propanesulfonylimino-2,3-dihydro-1,3-thiazol-4-yl)acetate, (16.4 g.), mp 140° to 142° C.

I.R. Spectrum (Nujol): 1740 (CO) cm$^{-1}$,

N.M.R. Spectrum (d$_6$-dimethylsulfoxide, δ): 3.62 (2H, s), 6.56 (1H, s).

To a solution prepared by stirring a mixture of selenium dioxide (6.2 g.), dioxane (320 ml.) and water (6.4 ml.) at 50° to 60° C. was added ethyl 2-(2-propanesulfonylamino-1,3-thiazol-4-yl)acetate, which can be represented as ethyl 2-(2-propanesulfonylimino-2,3-dihydro-1,3-thiazol-4-yl)acetate, (16.3 g.), and the mixture was refluxed for 1 hour. To the mixture was added selenium dioxide (0.6 g.), and the mixture was further refluxed for 30 minutes and selenium dioxide (0.3 g.) was added thereto, and then the mixture was further refluxed for 30 minutes. After the reaction, the reaction mixture was filtered, and then dioxane was distilled off. The residue was dissolved in ethyl acetate under heating and then treated with activated charcoal. The solvent was distilled off, and the residue was washed with a small amount of ethyl acetate and diethyl ether in turn and dried to give ethyl 2-(2-propanesulfonylamino-1,3-thiazol-4-yl)glyoxylate, which can be represented as ethyl 2-(2-propanesulfonylimino-2,3-dihydro-1,3-thiazol-4-yl)glyoxylate, (12.5 g.), mp 132° to 134° C.

I.R. Spectrum (Nujol): 1690, 1725 (CO) cm$^{-1}$,

N.M.R Spectrum (d$_6$-acetone, δ): 8.3 (1H, s).

A mixture of ethyl 2-(2-propanesulfonylamino-1,3-thiazol-4-yl)glyoxylate, which can be represented as ethyl 2-(2-propanesulfonylimino-2,3-dihydro-1,3-thiazol-4-yl)glyoxylate, (12.0 g.) and 1N sodium hydroxide aqueous solution (93 ml.) was stirred for 1 hour under ice-cooling. After the reaction, to the reaction mixture was added 1N hydrochloric acid (93 ml.) and the mixture was extracted with ethyl acetate under saturation with sodium chloride. The extract was washed with a saturated aqueous solution of sodium chloride and dried. The solvent was distilled off from the extract, and the residue was washed in diethyl ether, collected by filtration and dried to give 2-(2-propanesulfonylamino-1,3-thiazol-4-yl)glyoxylic acid, which can be represented as 2-(2-propanesulfonylimino-2,3-dihydro-1,3-thiazol-4-yl)glyoxylic acid, (7.3 g.), mp. 148° to 150° C.

I.R. Spectrum (Nujol): 1685, 1720 (CO) cm$^{-1}$,

N.M.R. Spectrum (d$_6$-acetone, δ): 8.3 (1H, s).

(5) Preparation of
2-(2-tetrahydropyranyl)oxy-2-(2-mesylamino-1,3-thiazol-4-yl)acetic acid, which can be represented as
2-(2-tetrahydropyranyl)oxy-2-(2-mesylimino-2,3-dihydro-1,3-thiazol-4-yl)acetic acid A mixture of ethyl 2-(2-amino-1,3-thiazol-4-yl)acetate, which can be represented as ethyl 2-(2-imino-2,3-dihydro-1,3-thiazol-4-yl)acetate, (5.6 g.), mesyl chloride (6.9 g.), pyridine (15 ml.) and methylene chloride (45 ml.) was refluxed for 5 hours. After the reaction, the reaction mixture was concentrated. The residue was poured into ice-water (150 ml.) and stirred. The precipitates were collected by filtration, washed with water and diethyl ether and dried to give pale brown powder of ethyl 2-(2-mesylamino-1,3-thiazol-4-yl)acetate, which can be represented as ethyl 2-(2-mesylimino-2,3-dihydro-1,3-thiazol-4-yl)acetate, (6.3 g.).

I.R. Spectrum (Nujol): 1730 (CO) cm$^{-1}$,

N.M.R. Spectrum (d$_6$-dimethylsulfoxide, δ): 2.95 (3H, s), 3.73 (2H, s), 6.7 (1H, s).

To a solution prepared by stirring a mixture of selenium dioxide (0.22 g.), dioxane (10 ml.) and water (0.2 ml.) for 10 minutes at 110° C. was added ethyl 2-(2-mesylamino-1,3-thiazol-4-yl)acetate, which can be represented as ethyl 2-(2-mesylimino-2,3-dihydro-1,3-thiazol-4-yl)acetate, (0.53 g.), and the mixture was refluxed for 1 hour. After the reaction, the reaction mixture was treated with activated charcoal. The precipitated crystals in the filtrate were collected by filtration and dried to give white crystals of ethyl 2-(2-mesylamino-1,3-thiazol-4-yl)glyoxylate, which can be represented as ethyl 2-(2-mesylimino-2,3-dihydro-1,3-thiazol-4-yl)glyoxylate, (0.22 g.), mp. 222° to 225° C. On the other hand, the remaining filtrate was concentrated and the residue was washed with water and diethyl ether in turn and then dried to give the same object compound (0.12 g.)

I.R. Spectrum (Nujol): 1685, 1720 (CO) cm$^{-1}$,

N.M.R. Spectrum (d$_6$-dimethylsulfoxide, δ): 3.05 (3H, s), 8.36 (1H, s).

To a mixture of ethyl 2-(2-mesylamino-1,3-thiazol-4-yl)glyoxylate, which can be represented as ethyl 2-(2-mesylimino-2,3-dihydro-1,3-thiazol-4-yl)glyoxylate, (3.60 g.) and ethanol (50 ml.) was added sodium borohydride (0.32 g.) under stirring and ice-cooling, and then the mixture was stirred for 40 minutes at room temperature. After the reaction, the reaction mixture was concentrated. The residue was poured into a mixture of ethyl acetate (100 ml.) and dilute hydrochloric acid, and the aqueous solution was separated. Thus obtained aqueous solution (pH 1 to 2) was subjected to salting-out and then extracted with ethyl acetate. The extract was washed with a saturated aqueous solution of sodium chloride and dried over magnesium sulfate. The extract was treated with activated charcoal and then the solvent was distilled off to give a solid of ethyl 2-hydroxy-2-(2-mesylamino-1,3-thiazol-4-yl)acetate, which can be represented as ethyl 2-hydroxy-2-(2-mesylimino-2,3-dihydro-1,3-thiazol-4-yl)acetate, (2.6 g.)

I.R. Spectrum (liquid): 1710 (CO) cm$^{-1}$,

N.M.R. Spectrum (d$_6$-dimethylsulfoxide, δ): 2.9 (3H, s), 5.1 (1H, s), 6.7 (1H, s).

To a suspension of ethyl 2-hydroxy-2-(2-mesylamino-1,3-thiazol-4-yl)acetate, which can be represented as ethyl 2-hydroxy-2-(2-mesylimino-2,3-dihydro-1,3-thiazol-4-yl)acetate, (1.0 g.) and 3,4-dihydro-2H-pyran (0.36 g.) in ethyl acetate (5 ml.) was added p-toluene sulfonic acid (10 mg) at room temperature with stirring, and then the suspension was stirred for 8 hours at the same temperature. After the reaction, the reaction mixture was poured into 5% sodium bicarbonate aqueous solution (10 ml.) and then the aqueous layer was separated. To the remaining organic layer was added diethyl ether (10 ml.) and then extracted with 5% sodium bicarbonate aqueous solution (20 ml.). Thus obtained aqueous extract was combined with the separated aqueous layer and adjusted to pH 4 with acetic acid and then extracted with ethyl acetate. The extract was washed with a saturated aqueous solution of sodium chloride, treated with activated charcoal and then dried over magnesium sulfate. The solvent was distilled off from the extract to give dark yellow oil of ethyl 2-(2-tetrahydropyranyl)oxy-2-(2-mesylamino-1,3-thiazol-4-yl)acetate, which can be represented as ethyl 2-(2-tetrahydropyranyl)oxy-2-(2-mesylimino-2,3-dihydro-1,3-thiazol-4-yl)acetate, (1.0 g.).

N.M.R. Spectrum (CDCl$_3$, $\delta$): 3.03 (3H, s), 5.2 ($\frac{1}{2}$H, s), 5.3 ($\frac{1}{2}$H, s), 6.6 (1H, s).

To ethyl 2-(2-tetrahydropyranyl)oxy-2-(2-mesylamino-1,3-thiazol-4-yl)acetate, which can be represented as ethyl 2-(2-tetrahydropyranyl)oxy-2-(2-mesylimino-2,3-dihydro-1,3-thiazol-4-yl)acetate, (0.85 g.) was added 1H sodium hydroxide aqueous solution prepared by sodium hydroxide (0.28 g.) and water (7 ml.), and then the mixture was stirred for 1 hour at room temperature. After the reaction, to the reaction mixture was added ethyl acetate. The mixture was adjusted to pH 1 to 2 with 2N hydrochloric acid, and the aqueous layer was separated. The aqueous layer was subjected to saltingout and then extracted with ethyl acetate. The extract was washed with a saturated aqueous solution of sodium chloride, dried over magnesium sulfate and then the solvent was distilled off to give a foamy substance of 2-(2-tetrahydropyranyl)oxy-2-(2-mesylamino-1,3-thiazol-4-yl)acetic acid, which can be represented as 2-(2-tetrahydropyranyl)oxy-2-(2-mesylimino-2,3-dihydro-1,3-thiazol-4-yl)acetic acid, (0.52 g.).

I.R. Spectrum (liquid): 1730 (CO) cm$^{-1}$,
N.M.R. Spectrum (CDCl$_3$, $\delta$): 3.0 (3H, s), 5.30 ($\frac{1}{2}$H, s), 5.33 ($\frac{1}{2}$H, s), 6.7 (1H, s).

(6) Preparation of 2-[2-(N-methyl-N-tert-pentyloxycarbonylamino)-1,3-thiazol-4-yl]glyoxylic acid (a) To a solution of ethyl 2-(2-methylamino-1,3-thiazol-4-yl)acetate, which can be represented as ethyl 2-(2-methylimino-2,3-dihydro-1,3-thiazol-4-yl)acetate, (8 g.) in a mixture of pyridine (80 ml.) and methylene chloride (40 ml.) was dropwise added tert-pentyl chloroformate over 2 hours at $-25°$ to $-20°$ C. with stirring, and the mixture was stirred for 30 minutes at the same temperature. After the reaction, the reaction mixture was poured into water (200 ml.), the mixture was extracted with ethyl acetate (300 ml.), and then the organic layer was separated. The organic layer was washed with 2N hydrochloric acid, water, 5% sodium bicarbonate aqueous solution and water in turn. The organic layer was dried over magnesium sulfate and then concentrated to give oil of ethyl 2-[2-(N-methyl-N-tert-pentyloxycarbonylamino)1,3-thiazol-4-yl]acetate (14.5 g.).

N.M.R. Spectrum (CDCl$_3$, $\delta$): 0.92 (3H, t, J=8 Hz), 1.25 (3H, t, J=8 Hz), 1.52 (6H, s), 1.9 (2H, q, J=8 Hz), 3.55 (3H, s), 3.7 (2H, s), 4.17 (2H, q, J=8 Hz), 6.75 (1H, s).

(b) A mixture of selenium dioxide (0.452 g.), dioxane (9 ml.) and water (0.36 ml.) was refluxed in bath at 110° C., and to the solution was added a solution of ethyl 2-[2-(N-methyl-N-tert-pentyloxycarbonylamino)-1,3-thiazol-4-yl]acetate (1.07 g.) and dioxane (9 ml.), and the mixture was stirred for 4.5 hours at the same temperature. After the reaction, the reaction mixture was filtered, and dioxane was distilled off from the filtrate under reduced pressure. To the residue were added water and ethyl acetate with stirring, and then ethyl acetate layer was separated. The ethyl acetate layer, was dried over magnesium sulfate and then concentrated to give oil of ethyl 2-[2-(N-methyl-N-tert-pentyloxycarbonylamino)-1,3-thiazol-4-yl]glyoxylate (0.45 g.).

I.R. Spectrum (Nujol): 1730, 1690 cm$^{-1}$
N.M.R. Spectrum (CDCl$_3$, $\delta$): 0.95 (3H, t, J=8 Hz), 1.4 (3H, t, J=8 Hz), 1.53 (6H, s), 1.9 (2H, q, J=8 Hz), 3.6 (3H, s), 4.42 (2H, q, J=8 Hz), 8.17 (1H, s).

(c) To a solution of ethyl 2-[2-(N-methyl-N-tert-pentyloxycarbonylamino)-1,3-thiazol-4-yl]glyoxylate (3.1 g.) in ethanol (40 ml.) was added 1N sodium hydroxide aqueous solution (14.2 ml.) under ice-cooling and stirring, and the mixture was further stirred for 30 minutes at the same temperature. After the reaction, ethanol was distilled off from the reaction mixture below 20° C. under reduced pressure. To the residue was added water (50 ml.), and after layering with ethyl acetate, the mixture was adjusted to pH 3 with 2N hydrochloric acid. The ethyl acetate layer was separated from the mixture, washed with water, dried over magnesium sulfate and then treated with an activated charcoal. The solvent is distilled off from the resulting ethyl acetate layer to give solid of 2-[2-(N-methyl-N-tert-pentyloxycarbonylamino)-1,3-thiazol-4-yl]glyoxylic acid (2.4 g.).

I.R. Spectrum (Nujol): 1743, 1700, 1650 cm$^{-1}$
N.M.R. Spectrum (CDCl$_3$, $\delta$): 0.92 (3H, t, J=8 Hz), 1.54 (6H, s), 1.84 (2H, q, J=8 Hz), 3.6 (3H, s), 8.54 (1H, s).

(7) Preparation of 2-(2-formylamino-5-chloro-1,3-thiazol-4-yl)glyoxylic acid which can be represented as 2-(2-formylimino-5-chloro-2,3-dihydro-1,3-thiazol-4-yl)glyoxylic acid (a) A suspension of ethyl 2-(2-formylamino-1,3-thiazol-4-yl)glyoxylate, which can be represented as ethyl 2-(2-formylimino-2,3-dihydro-1,3-thiazol-4-yl)glyoxylate, (6.9 g.) in dimethylformamide (40 ml.) was heated at 60° C. to produce a solution, and to the solution was dropwise added a solution of trichloroisocyanuric acid (2.8 g.) in dimethylformamide (10 ml.) over 15 minutes at the same temperature with stirring and then the mixture was further stirred for 1 hours at the same temperature. After the reaction, the reaction mixture was poured into ice-water (400 g.). The precipitates were collected by filtration, washed with water and then dried to give ethyl 2-(2-formylamino-5-chloro-1,3-thiazol-4-yl)glyoxylate, which can be represented as ethyl 2-(2-formylimino-5-chloro-2,3-dihydro-1,3-thiazol-4-yl)-glyoxylate, (7.1 g.), mp. 151° to 153° C. The remaining filtrate was extracted with ethyl acetate, and the extract was washed with water and then dried over magnesium sulfate. The solvent was distilled off from the extract to give further the same object compound (0.75 g.).

I.R. Spectrum (Nujol): 3150, 1740, 1675 (broad) cm$^{-1}$,

N.M.R. Spectrum (d$_6$-dimethylsulfoxide, δ): 1.33 (3H, t, J=13 Hz), 4.40 and 4.57 (2H, AB$_q$, J=13 Hz), 8.67 (1H, s), 12.9–13.2 (1H, m).

(b) Ethyl 2-(2-formylamino-5-chloro-1,3-thiazol-4-yl)-glyoxylate, which can be represented as ethyl 2-(2-formylimino-5-chloro-2,3-dihydro-1,3-thiazol-4-yl)glyoxylate, (1.3 g.) was dissolved in 1N potassium hydroxide aqueous solution (10 ml.) at room temperature with stirring and the solution was stirred for 5 minutes at the same temperature. After the reaction, the reaction mixture was cooled with ice and then adjusted to pH 1 with 10% hydrochloric acid. The precipitates were collected by filtration, washed with water and then dried to give 2-(2-formylamino-5-chloro-1,3-thiazol-4-yl)glyoxylic acid (0.91 g.), which can be represented as 2-(2-formylimino-5-chloro-2,3-dihydro-1,3-thiazol-4-yl)glyoxylic acid, mp. 148° to 152° C. (dec.). The remaining filtrate and washing were combined together and then extracted with ethyl acetate. The extract was washed with water, dried over magnesium sulfate and then the solvent was distilled off to give further the same object compound (0.23 g.).

I.R. Spectrum (Nujol): 3130, 2400-3000, 1735, 1670, 1640 cm$^{-1}$, (8) Preparation of 2-(2-formylamino-1,3-thiazol-4-yl)glyoxylic acid which can be represented as 2-(2-formylimino-2,3-dihydro-1,3-thiazol-4-yl)glyoxylic acid (a) To acetic anhydride (384 ml.) was dropwise added formic acid (169.2 ml.) over 15 to 20 minutes under cooling below 35° C., and the mixture was stirred for 1 hour at 55° to 60° C. To the mixture was added ethyl 2-(2-amino-1,3-thiazol-4-yl)-acetate, which can be represented as ethyl 2-(2-imino-2,3-dihydro-1,3-thiazol-4-yl)acetate, (506 g.) over 15 to 20 minutes under ice-cooling and stirring, and then the mixture was stirred for 1 hour at room temperature. After the reaction, the solvents were distilled off. To the residue was added diisopropyl ether (2500 ml.), and the mixture was stirred for 1 hour at room temperature. The precipitates were collected by filtration, washed with diisopropyl ether and then dried to give ethyl 2-(2-formylamino-1,3-thiazol-4-yl)acetate, which can be represented as ethyl 2-(2-formylimino-2,3-dihydro-1,3-thiazol-4yl)acetate, (451.6 g.), mp. 125° to 126° C. The remaining filtrate was concentrated, and the residue was washed with diisopropyl ether (500 ml.) and then dried to give further the same object compound (78.5 g.).

I.R. Spectrum (Nujol): 1737, 1700 cm$^{-1}$,

N.M.R. Spectrum (CDCl$_3$, δ): 1.25 (3H, t, J=8 Hz), 3.7 (2H, s), 4.18 (2H, q, J=8 Hz), 6.9 (1H, s), 8.7 (1H, s).

(b)-(i) Ethyl 2-(2-formylamino-1,3-thiazol-4-yl)acetate, which can be represented as ethyl 2-(2-formylimino-2,3-dihydro-1,3-thiazol-4-yl)acetate, (250 g.) was treated in a similar manner to that of the above preparation (6) (b) to give ethyl 2-(2-formylamino-1,3-thiazol-4-yl)glyoxylate, which can be represented as ethyl 2-(2-formylimino-2,3-dihydro-1,3-thiazol-4-yl)glyoxylate, (140.5 g.).

I.R. Spectrum (Nujol): 1738, 1653 cm$^{-1}$,

N.M.R. Spectrum (d$_6$-dimethylsulfoxide, δ): 1.34 (3H, t, J=8 Hz), 4.38 (2H, q, J=8 Hz), 8.52 (1H, s), 8.57 (1H, s).

(b)-(ii) A mixture of manganous acetate tetrahydrate (120 g.), acetic acid (1000 ml.) and acetic anhydride (100 ml.) was stirred for 20 minutes in an oil bath heated at 130° to 135° C., and to the mixture was added potassium permanganate (20 g.) over 5 minutes at 105° to 110° C. with stirring and then the mixture was further stirred for 30 minutes at 130° to 135° C. The mixture was cooled to room temperature, and to the mixture was added ethyl 2-(2-formylamino-1,3-thiazol-4-yl)acetate, which can be represented as ethyl 2-(2-formylimino-2,3-dihydro-1,3-thiazol-4-yl)acetate, (53.5 g.), and then the mixture was stirred for 15 hours at 38° to 40° C. under introduction of air at the rate of 6000 ml. per minute. After the reaction, the precipitates were collected by filtration. The precipitates were washed with acetic acid and water in turn and then dried to give ethyl 2-(2-formylamino-1,3-thiazol-4-yl)glyoxylate, which can be represented as ethyl 2-(2-formylimino-2,3-dihydro-1,3-thiazol-4-yl)glyoxylate, (41.5 g.), mp. 232° to 233° C. (dec.).

(c) Ethyl 2-(2-formylamino-1,3-thiazol-4-yl)glyoxylate, which can be represented as ethyl 2-(2-formylimino-2,3-dihydro-1,3-thiazol-4-yl)glyoxylate, (281 g.) was treated in a similar manner to that of the above preparation (6)(c) to give 2-(2-formylamino-1,3-thiazol-4-yl)glyoxylic acid, which can be represented as 2-(2-formylimino-2,3-dihydro-1,3-thiazol-4-yl)-glyoxylic acid, (234 g.), mp. 133° to 136° C. (dec.).

N.M.R. Spectrum (NaDCO$_3$, δ): 8.27 (1H, s) 8.6 (1H, s)

(9) Preparation of 2-[2-[3-methyl)thioureido]-1,3-thiazol-4-yl]glyoxylic acid which can be represented as 2-[2-[3-(methyl)thioureido]-2,3-dihydro-1,3-thiazol-4-yl]-glyoxylic acid (a) To a suspension of ethyl 2-(2-formylamino-1,3-thiazol-4-yl)glyoxylate, which can be represented as ethyl 2-(2-formylimino-2,3-dihydro-1,3-thiazol-4-yl)glyoxylate, (31.3 g.) in ethanol (600 ml.) was dropwise added phosphorus oxychloride (41.9 g.) under ice-cooling and stirring, and the mixture was stirred for 30 minutes at 50° C. After the reaction, the solvent was distilled off. The residue was washed with diethyl ether and then dried to give ethyl 2-(2-amino-1,3-thiazol-4-yl)glyoxylate hydrochloride, which can be represented as ethyl 2-(2-imino-2,3-dihydro-1,3-thiazol-4-yl)glyoxylate hydrochloride, in quantitative yield, mp. 263° to 264° C. (dec.).

I.R. Spectrum (Nujol): 1748, 1697 cm$^{-1}$.

(b) A solution of ethyl 2-(2-amino-1,3-thiazol-4-yl)-glyoxylate hydrochloride, which can be represented as ethyl 2-(2-imino-2,3-dihydro-1,3-thiazol-4-yl)glyoxylate, (30 g.) in water (150 ml.) was treated with an activated charcoal, and the solution was neutralized with sodium bicarbonate (10.7 g.) at room temperature with stirring. The precipitates were collected by filtration, washed with water and then dried to give ethyl 2-(2-amino-1,3-thiazol-4-yl)glyoxylate, which can be represented as ethyl 2-(2-imino-2,3-dihydro-1,3-thiazol-4-yl)glyoxylate, (21.8 g.), mp. 186° to 187° C. (dec.).

(c) A mixture of ethyl 2-(2-amino-1,3-thiazol-4-yl)-glyoxylate, which can be represented as ethyl 2-(2-imino-2,3-dihydro-1,3-thiazol-4-yl)glyoxylate, (20 g.) and methyl isothiocyanate (73 g.) was stirred for 5 hours at 90° to 95° C. After the reaction, to the reaction mixture was added diethyl ether. The precipitates were collected by filtration, washed with diethyl ether and then dried to give ethyl 2-[2-[3-(methyl)thioureido]-1,3-thiazol-4-yl]glyoxylate, which can be represented as ethyl 2-[2-[3-(methyl)thioureido]-2,3-dihydro-1,3-thiazol-4-yl]glyoxylate, (21.3 g.), mp. 121° to 123° C.

I.R. Spectrum (Nujol): 1730, 1683 cm$^{-1}$,

N.M.R. Spectrum (d$_6$-dimethylsulfoxide, δ): 1.38 (3H, t, J=7 Hz), 3.05 (3H, s), 4.43 (2H, q, J=7 Hz), 8.33 (1H, s).

(d) To a mixture of ethyl 2-[2-[3-(methyl)thioureido]-1,3-thiazol-4-yl]glyoxylate, which can be represented as ethyl 2-[2-[3-(methyl)thioureido]-2,3-dihydro-1,3-thiazol-4-yl]glyoxylate, (21 g.), ethanol (200 ml.) and water (100 ml.) was added 1N sodium hydroxide aqueous solution (154 ml.) under ice-cooling and stirring. The mixture was further stirred for 10 minutes and then neutralized with 1N hydrochloric acid (154 ml.). The precipitates were collected by filtration, washed with water and then dried to give 2-[2-[3-(methyl)thioureido]-1,3-thiazol-4-yl]-glyoxylic acid, which can be represented as 2-[2-[3-(methyl)-thioureido]-2,3-dihydro-1,3-thiazol-4-yl]glyoxylic acid, (17.8 g.), mp.>250° C.

N.M.R. Spectrum (d$_6$-dimethylsulfoxide, δ): 3.01 (3H, s), 8.25 (1H, s).

(10) Preparation of 2-hydroxy-2-(2-formylamino-1,3-thiazol-4-yl)acetic acid which can be represented as 2-hydroxy-2-(2-formylimino-2,3-dihydro-1,3-thiazol-4-yl)acetic acid To a suspension of 2-(2-formylamino-1,3-thiazol-4-yl)glyoxylic acid, which can be represented as 2-(2-formylimino-2,3-dihydro-1,3-thiazol-4-yl)glyoxylic acid, (20 g.) in water (400 ml.) was added sodium bicarbonate (8.4 g.) under ice-cooling and stirring, and the mixture was stirred for 10 minutes at the same temperature, and then diethyl ether (10 ml.) was added thereto. To the mixture was added sodium borohydride (1.52 g.) over 10 minutes with stirring at the same temperature, and the mixture was stirred for 1 hour and 50 minutes at the same temperature. After the reaction, the reaction mixture was filtered. The filtrate was adjusted to pH 4.0 with 10% hydrochloric acid and then concentrated under reduced pressure till the volume became 100 ml. The concentrated filtrate was adjusted to pH 1 with 10% hydrochloric acid, and crystallization was induced by scratching. The concentrated filtrate was stirred for 1 hour at room temperature and then allowed to stand overnight in a refrigerator. The precipitates were collected by filtration, washed with ice-water twice and then dried under suction to give 2-hydroxy-2-(2-formylamino-1,3-thiazol-4-yl)acetic acid, which can be represented as 2-hydroxy-2-(2-formylimino-2,3-dihydro-1,3-thiazol-4-yl)acetic acid, (14.8 g.), mp. 188° to 189° C. (dec.).

I.R. Spectrum (Nujol): 1730, 1635 cm$^{-1}$,

N.M.R. Spectrum (N$_a$DCO$_3$, δ): 5.07 (1H, s), 7.15 (1H, s), 8.5 (1H, s).

(11) Preparation of 2-hydroxy-2-(2-amino-1,3-thiazol-5-yl)acetic acid which can be represented as 2-hydroxy-2-(2-imino-2,3-dihydro-1,3-thiazol-5-yl)acetic acid A mixture of 2-amino-1,3-thiazole, which can be represented as 2-imino-2,3-dihydro-1,3-thiazole, (36.3 g.), glyoxylic acid hydrate (50 g.) and 1N sodium hydroxide (543 ml.) was stirred for 1.5 hours at 90° to 93° C. After the reaction, the reaction mixture was treated with an activated charcoal and then adjusted to pH 3. The mixture was allowed to stand overnight under ice-cooling. The precipitates were collected by filtration, washed with water and then dried to give 2-hydroxy-2-(2-amino-1,3-thiazol-5-yl)acetic acid hydrate, which can be represented as 2-hydroxy-2-(2-imino-2,3-dihydro-1,3-thiazol-5-yl)acetic acid hydrate (48.1 g.), mp. 140° to 200° C. (dec.).

I.R. Spectrum (Nujol): 1622–1642 cm$^{-1}$,

N.M.R. Spectrum (DCl, δ): 5.65 (1H, d, J=1.2 Hz), 7.35 (1H, s).

(12) Preparation of 2-(2-amino-1,3-thiazol-5-yl)-glyoxylic acid which can be represented as 2-(2-imino-2,3-dihydro-1,3-thiazol-5-yl)glyoxylic acid A mixture of 2-hydroxy-2-(2-amino-1,3-thiazol-5-yl)acetic acid, which can be represented as 2-hydroxy-2-(2-imino-2,3-dihydro-1,3-thiazol-5-yl)acetic acid, (0.92 g.) and water (10 ml.) was adjusted to pH 7 to 7.5 with a 10% sodium hydroxide aqueous solution, and to the mixture was added manganese dioxide (1.74 g.) and then the mixture was stirred for 5 hours at 50° to 60° C. After the reaction, manganese dioxide was filtered off and then washed with a small amount of water. The filtrate and washing were combined together, adjusted to pH 1 with concentrated hydrochloric acid and then stirred for 15 minutes under ice-cooling. The precipitates were collected by filtration, washed with water and then dried to give 2-(2-amino-1,3-thiazol-5-yl)glyoxylic acid, which can be represented as 2-(2-imino-2,3-dihydro-1,3-thiazol-5-yl)glyoxylic acid, (0.53 g.), mp. 185° to 250° C. (dec.).

I.R. Spectrum (Nujol): 1690, 1650 cm$^{-1}$,

N.M.R. Spectrum (d$_6$-dimethylsulfoxide, δ): 8.25 (1H, s).

(13) Preparation of 2-(2-formylamino-1,3-thiazol-5-yl)glyoxylic acid which can be represented as 2-(2-formylimino-2,3-dihydro-1,3-thiazol-5-yl)glyoxylic acid 2-(2-Amino-1,3-thiazol-5-yl)glyoxylic acid, which can be represented as 2-(2-imino-2,3-dihydro-1,3-thiazol-5-yl)-glyoxylic acid, (3 g.) was treated in a similar manner to that of the above preparation (8)(a) to give 2-(2-formylamino-1,3-thiazol-5-yl)glyoxylic acid, which can be represented as 2-(2-formylimino-2,3-dihydro-1,3-thiazol-5-yl)glyoxylic acid, (3.15 g.), mp. 180° to 210° C.

I.R. Spectrum (Nujol): 1712, 1689, 1665 cm$^{-1}$,

N.M.R. Spectrum (d$_6$-dimethylsulfoxide, δ): 8.22 (1H, s), 8.67 (1H, s).

(14) Preparation of 2-formyloxy-2-(2-formylamino-1,3-thiazol-5-yl)acetic acid which can be represented as 2-formyloxy-2-(2-formylimino-2,3-dihydro-1,3-thiazol-5-yl)acetic acid A mixture of formic acid (10 m mol) and acetic anhydride (10 m mol) was stirred for 2 hours at 50° to 60° C. and then cooled to −7° to −5° C. To the mixture was added 2-hydroxy-2-(2-amino-1,3-thiazol-5-yl)acetic acid hydrate, which can be represented as 2-hydroxy-2-(2-imino-2,3-dihydro-1,3-thiazol-5-yl)acetic acid hydrate, (0.48 g.) at the same temperature, and the mixture was stirred for 3 hours at the same temperature. To the mixture was further added a mixture of formic acid (2.5 m mol) and acetic anhydride (2.5 m mol) at the same temperature and then the mixture was further stirred for 1 hour at the same temperature. After the reaction, the solvent was distilled off. To the residue were added water and methyl isobutyl ketone and then the insoluble material was filtered off. The filtrate was treated with an activated charcoal, and the methyl isobutyl ketone layer was separated. The remaining aqueous layer was further extracted with methyl isobutyl ketone. The methyl isobutyl ketone layers were combined together, dried over magnesium sulfate, treated with an activated charcoal, and then the solvent was distilled off. The residue was pulverized in diethyl ether to give powder of 2-formyloxy-2-(2-formylamino-1,3-thiazol-5-yl)acetic acid, which can be represented as 2-formyloxy-2-(2-formylimino-2,3-dihydro-1,3-thiazol-5-yl)acetic acid, (0.31 g.).

I.R. Spectrum (Nujol): 1723, 1685 cm$^{-1}$,

N.M.R. Spectrum ($d_6$-dimethylsulfoxide, $\delta$): 6.24 (1H, s), 7.54 (1H, s), 8.24 (1H, s), 8.45 (1H, s).

(15) Preparation of 2-(2-formylamino-1,3-thiazol-4-yl)-glyoxylic acid which can be represented as 2-(2-formylimino-2,3-dihydro-1,3-thiazol-4-yl)glyoxylic acid (a) Methyl 2-(2-amino-1,3-thiazol-4-yl)acetate, which can be represented as methyl 2-(2-imino-2,3-dihydro-1,3-thiazol-4-yl)acetate, (100 g.) was treated in a similar manner to that of the above preparation (8)(a) to give methyl 2-(2-formylamino-1,3-thiazol-4-yl)acetate, which can be represented as methyl 2-(2-formylimino-2,3-dihydro-1,3-thiazol-4-yl)acetate, (109.9 g.), mp. 154° to 155° C.

I.R. Spectrum (Nujol): 1733, 1680 cm$^{-1}$,

N.M.R. Spectrum ($d_6$-dimethylsulfoxide, $\delta$): 3.72 (3H, s), 3.89 (2H, s), 7.01 (1H, s), 8.45 (1H, s).

(b) Methyl 2-(2-formylamino-1,3-thiazol-4-yl)acetate, which can be represented as methyl 2-(2-formylimino-2,3-dihydro-1,3-thiazol-4-yl)acetate, (60 g.) was treated in a similar manner to that of the above preparation (8)(b)-(ii) to give methyl 2-(2-formylamino-1,3-thiazol-4-yl)glyoxylate, which can be represented as methyl 2-(2-formylimino-2,3-dihydro-1,3-thiazol-4-yl)glyoxylate, (27.1 g.), mp. 223° to 225° C. (dec.).

N.M.R. Spectrum ($d_6$-dimethylsulfoxide, $\delta$): 3.95 (3H, s), 8.2 (1H, s), 8.3 (1H, s).

(c) Methyl 2-(2-formylamino-1,3-thiazol-4-yl)glyoxylate, which can be represented as methyl 2-(2-formylimino-2,3-dihydro-1,3-thiazol-4-yl)glyoxylate, was treated in a similar manner to that of the above preparation (8)(c) to give 2-(2-formylamino-1,3-thiazol-4-yl)glyoxylic acid, which can be represented as 2-(2-formylimino-2,3-dihydro-1,3-thiazol-4-yl)glyoxylic acid, mp. 133° to 136° C. (dec.).

EXAMPLE 1

To dimethylformamide (2.25 g.) was dropwise added phosphorus oxychloride (2.36 g.) under stirring and ice-cooling, and the mixture was stirred for 30 minutes at 40° C. To the mixture was added ethyl acetate (50 ml.), and the mixture was cooled to −20° C. To the mixture was gradually added 2-(2-tert-pentyloxycarbonylamino-1,3-thiazol-4-yl)glyoxylic acid, which can be represented as 2-(2-tert-pentyloxycarbonylimino-2,3-dihydro-1,3-thiazol-4-yl)glyoxylic acid, (4.00 g.) over about 5 minutes at −20° to −10° C. with stirring, and the mixture was further stirred for 40 minutes at the same temperature. Thus obtained mixture was dropwise added to the solution, which was prepared by stirring the mixture of 3-(5-methyl-1,3,4-thiadiazol-2-yl)thiomethyl-7-amino-3-cephem-4-carboxylic acid (5.30 g.) and bis(trimethylsilyl)acetamide (15.4 ml.) in ethyl acetate (100 ml.) for 30 minutes at room temperature and then by cooling to −40° C. The mixture was stirred for 40 minutes at the same temperature and further stirred for 30 minutes at −5° to 0° C. The reaction mixture was poured into 5% sodium bicarbonate aqueous solution, and the aqueous layer was separated. The remaining ethyl acetate layer was extracted twice with 5% sodium bicarbonate aqueous solution (40 ml.). Thus obtained aqueous layers were combined together and washed with ethyl acetate (50 ml.). To the aqueous solution was added ethyl acetate (100 ml.), and pH value of the aqueous portion of the mixture was adjusted to 2 with 10% hydrochloric acid under ice-cooling and stirring. After filtration of the mixture, the ethyl acetate layer was separated. The remaining aqueous layer was extracted twice with ethyl acetate (60 ml.). Thus obtained ethyl acetate layers were combined together, washed with a saturated aqueous solution of sodium chloride and water in turn and then dried over magnesium sulfate. After distillation of the solvent, the remaining residue was pulverized in diethyl ether, collected by filtration, washed with diethyl ether and then dried to give 3-(5-methyl-1,3,4-thiadiazol-2-yl)-thiomethyl-7-[2-(2-tert-pentyloxycarbonylamino-1,3-thiazol-4-yl)-glyoxylamido]-3-cephem-4-carboxylic acid, which can be represented as 3-(5-methyl-1,3,4-thiadiazol-2-yl)thiomethyl-7-[2-(2-tert-pentyloxycarbonylimino-2,3-dihydro-1,3-thiazol-4-yl)glyoxylamido]-3-cephem-4-carboxylic acid, (3.79 g.).

I.R. Spectrum (Nujol): 1782 ($\beta$-lactam) cm$^{-1}$

N.M.R. Spectrum ($d_6$-dimethylsulfoxide, $\delta$): 2.7 (3H, s), 3.57–3.85 (2H, broad s), 4.2 and 4.57 (2H, AB$_q$, J=14 Hz), 5.2 (1H, d, J=5 Hz), 5.77 (1H, d, J=5 Hz), 8.4 (1H, s).

EXAMPLE 2

To dimethylformamide (2.24 g.) was dropwise added phosphorus oxychloride (2.36 g.) over 10 minutes under stirring and ice-cooling, and the mixture was stirred for 30 minutes at 40° C. To the mixture was added ethyl acetate (40 ml.), and the mixture was cooled at −20° to −15° C. with stirring. To the mixture was added 2-(2-tert-pentyloxycarbonylamino-1,3-thiazol-4-yl)glyoxylic acid, which can be represented as 2-(2-tert-pentyloxycarbonylimino-2,3-dihydro-1,3-thiazol-4-yl)-glyoxylic acid, (4.0 g.) and the mixture was stirred for 30 minutes at the same temperature. Thus obtained mixture was added to the solution, which was prepared by stirring the mixture of bis(trimethylsilyl)acetamide (15 ml.) and 3-(1,3,4-thiadiazol-2-yl)thiomethyl-7-amino-3-cephem-4-carboxylic acid (6.35 g.) in ethyl acetate (50 ml.) at room temperature for 10 minutes, by adding dimethylformamide (6 ml.) thereto and then cooling to −40° C. The solution was stirred for 30 minutes at −40° C. and for 30 minutes at −20° C., and then the reaction mixture was poured into 5% sodium bicarbonate aqueous solution. The aqueous layer was separated from the mixture, washed with ethyl acetate, and the precipitates were filterred. The precipitates were washed with a mixture of acetone and water, and the washings were extracted with ethyl acetate, and then the extract was washed with sodium chloride aqueous solution and water in turn. On the other hand, to the aqueous filtrate was added ethyl acetate, and the mixture was adjusted to pH 1 to 2. The ethyl acetate layer was separated from the mixture and combined with the above obtained ethyl acetate extract together. The combined ethyl acetate layer was washed with water, dried over magnesium sulfate and then treated with activated charcoal. After distillation of the solvent from the ethyl acetate layer, the remaining residue was pulverized in diethyl ether, collected by filtration and then dried to give yellowish brown powder of 3-(1,3,4-thiadiazol-2-yl)thiomethyl-7-[2-(2-tert-pentyloxycarbonylamino-1,3-thiazol-4-yl)glyoxylamido]-3-cephem-4-carboxylic acid which can be represented as 3-(1,3,4-thiadiazol-2-yl)thiomethyl-7-[2-(2-tert-pentyloxycarbonylimino-2,3-dihydro-1,3-thiazol-4-yl)-glyoxylamido]-3-cephem-4-carboxylic acid, (3.2 g.).

N.M.R. Spectrum (d$_6$-dimethylsulfoxide, $\delta$): 3.57 and 3.87 (2H, AB$_q$, J=15 Hz), 3.67 and 4.27 (2H, AB$_q$, J=16 Hz), 5.17 (1H, d, J=5 Hz), 5.77 (1H, d, J=5 Hz), 8.33 (1H, s), 9.53 (1H, s).

EXAMPLE 3

To dimethylformamide (9.0 g.) was dropwise added phosphorus oxychloride (10.3 g.) over 20 minutes under stirring and ice-cooling, and the mixture was stirred for 30 minutes at 40° C. To the mixture was added ethyl acetate (140 ml.), and the mixture was cooled to −20° C. with stirring. To the mixture was added 2-(2-tert-pentyloxycarbonylamino-1,3-thiazol-4-yl)glyoxylic acid, which can be represented as 2-(2-tert-pentyloxycarbonyl-imino-2,3-dihydro-1,3-thiazol-4-yl)glyoxylic acid, (16.0 g.), and the mixture was stirred for 30 minutes at −20° to −15° C. Thus obtained mixture was added all at once to a solution, which was prepared by stirring a mixture of 7-aminocephalosporanic acid (18.2 g.) and bis(trimethylsilyl)acetamide (56 ml.) in ethyl acetate (220 ml.) for 30 minutes at room temperature and then by cooling it at −40° C. The mixture was stirred for 1 hour at −50° to −40° C. and further for 1 hour at −25° to −20° C. After the reaction, the reaction mixture was poured into 5% sodium bicarbonate aqueous solution (800 ml.). The aqueous layer was separated from the mixture, adjusted to pH 2 with 10% hydrochloric acid and then extracted with ethyl acetate. The extract was washed with water, dried over magnesium sulfate and then treated with an activated charcoal. After distillation of ethyl acetate from the extract, the residue was pulverized in a mixture of diethyl ether (100 ml.) and diisopropyl ether (200 ml.), collected by filtration and dried to give powder of 7-[2-(2-tert-pentyloxycarbonylamino-1,3-thiazol-4-yl)glyoxylamido]cephalosporanic acid, which can be represented as 7-[2-(2-tert-pentyloxycarbonylimino-2,3-dihydro-1,3-thiazol-4-yl)glyoxylamido]cephalosporanic acid, (23.1 g.)

I.R. Spectrum (Nujol): 1783 ($\beta$-lactam) cm$^{-1}$

N.M.R. Spectrum (d$_6$-dimethylsulfoxide, $\delta$): 2.17 (3H, s), 3.4–3.9 (2H, m), 4.8 and 5.17 (2H, AB$_q$, J=13 Hz), 5.25 (1H, d, J=5 Hz), 5.9 (1H, d, J=5 Hz), 8.45 (1H, s).

EXAMPLE 4

To dimethylformamide (1.1 g.) was dropwise added phophorus oxychloride (1.5 g.) under stirring and ice-cooling, and the mixture was stirred for 30 minutes at 40° C. To the mixture was added ethyl acetate (10 ml.), and the mixture was cooled to −20° to −10° C. with stirring. To the mixture was added a solution of 2-hydroxy-2-(2-tert-pentyloxycarbonylamino-1,3-thiazol-4-yl)acetic acid, which can be represented as 2-hydroxy-2-(2-tert-pentyloxycarbonylimino-2,3-dihydro-1,3-thiazol-4-yl)acetic acid, (1.1 g.) in ethyl acetate (15 ml.) below −20° C. under stirring, and then the mixture was stirred for 30 minutes at the same temperature. Thus obtained mixture was added all at once to the cooled solution prepared in the similar manner as in Example 1 from 3-(1-methyl-1H-tetrazol-5-yl)thiomethyl-7-amino-3-cephem-4-carboxylic acid (1.9 g.), bis(trimethylsilyl)acetamide (6 ml.) and ethyl acetate (20 ml.). The mixture was stirred for 30 minutes at −40° C. and further for 1.5 hours at −20° to −10° C. After the reaction, the reaction mixture was poured into 5% sodium bicarbonate aqueous solution, and the aqueous layer was separated. The remaining ethyl acetate layer was further extracted with 5% sodium bicarbonate aqueous solution. Thus obtained aqueous layer and the solution were combined together and washed with diethyl ether. To the aqueous layer was added ethyl acetate, and the mixture was adjusted to pH 1 to 2 with 10% hydrochloric acid and then the ethyl acetate layer was separated. The ethyl acetate layer was washed with a saturated aqueous solution of sodium chloride and then dried over magnesium sulfate. After distillation of the solvent, the residue was pulverized in diethyl ether and then collected by filtration to give pale brown powder of 3-(1-methyl-1H-tetrazol-5-yl)thiomethyl-7-[2-formyloxy-2-(2-tert-pentyloxycarbonylamino-1,3-thiazol-4-yl)-acetamido]-3-cephem-4-carboxylic acid, which can be represented as 3-(1-methyl-1H-tetrazol-5-yl)thiomethyl-7-[2-formyloxy-2-(2-tert-pentyloxycarbonylimino-2,3-dihydro-1,3-thiazol-4-yl)-acetamido]-3-cephem-4-carboxylic acid, (0.86 g.).

I.R. Spectrum (Nujol): 1783 ($\beta$-lactam), 1680–1740 (CO) cm$^{-1}$,

N.M.R. Spectrum (d$_6$-dimethylsulfoxide, $\delta$): 3.7 (2H, broad s), 3.94 (3H, s), 4.3 (2H, broad s), 5.0–5.15 (1H, m), 5.55–5.8 (1H, m), 6.17 (1H, s), 7.22 (1H, s), 8.36 (1H, s).

EXAMPLE 5

To dimethylformamide (3.74 g.) was dropwise added phosphorus oxychloride (6.46 g.) over 5 minutes under stirring and ice-cooling, and the mixture was stirred for 30 minutes at 40° C. To the mixture was added ethyl acetate (120 ml.) with stirring, and the mixture was cooled to −20° C. with stirring. To the mixture was added all at once 2-(2-oxo-2,3-dihydro-1,3-thiazol-4-yl)glyoxylic acid, which can be represented as 2-(2-hydroxy-1,3-thiazol-4-yl)glyoxylic acid, (6.05 g.) and to the mixture was added dimethylformamide (55 ml.) over 10 minutes at −20° C., and then the mixture was stirred for 40 minutes at the same temperature. Thus obtained mixture was added to the solution prepared in the similar manner as in Example 1 from 3-(1-methyl-1H-tetrazol-5-yl)thiomethyl-7-amino-3-cephem-4-carboxylic acid (10.50 g.), bis(trimethylsilyl)acetamide (35 ml.) and ethyl acetate (150 ml.), at −50° to −40° C. with stirring. The mixture was stirred for 30 minutes at −40° C. and further stirred for 30 minutes at −20° C. After the reaction, the reaction mixture was poured into 5% sodium bicarbonate aqueous solution (250 ml.), and the aqueous layer was separated. The aqueous layer was washed with ethyl acetate and adjusted to pH 1 with 10% hydrochloric acid, and then extracted with ethyl acetate. The extract was washed with water, dried over magnesium sulfate and then treated with activated charcoal. After distillation of ethyl acetate from the extract, the residue was pulverized in diethyl ether, collected by filtration and dried to give pale yellow powder of 3-(1-methyl-1H-tetrazol-5-yl)thiomethyl-7-[2-(2-oxo-2,3-dihydro-1,3-thiazol-4-yl)glyoxylamido]-3-cephem-4-carboxylic acid, which can be represented as 3-(1-methyl-1H-tetrazol-5-yl)thiomethyl-7-[2-(2-hydroxy-1,3-thiazol-4-yl)glyoxylamido]-3-cephem-4-carboxylic acid, (9.2 g.).

I.R. Spectrum (Nujol): 1762 ($\beta$-lactam) cm$^{-1}$,

N.M.R. Spectrum (d$_6$-dimethylsulfoxide, $\delta$): 3.74 (2H, broad s), 3.93 (3H, s), 4.25 and 4.5 (2H, AB$_q$, J=14 Hz), 5.18 (1H, d, J=5 Hz), 5.73 (1H, dd, J=5 and 6 Hz), 7.97 (1H, s).

EXAMPLE 6

To dimethylformamide (1.59 g.) was dropwise added phosphorus oxychloride (4.16 g.) under stirring and ice-cooling, and the mixture was stirred for 30 minutes at 40° C. To the mixture was added ethyl acetate (20 ml.) with stirring, and the mixture was cooled to −20° to −10° C. with stirring. To the mixture was dropwise added a mixture of 2-(2-propanesulfonylamino-1,3-thiazol-4-yl)glyoxylic acid, which can be represented as 2-(2-propanesulfonylimino-2,3-dihydro-1,3-thiazol-4-yl)-glyoxylic acid, (6.0 g.), ethyl acetate (60 ml.) and dimethylformamide (4 ml.) over 10 minutes at −20° to −10° C. with stirring, and then the mixture was stirred for 40 minutes at the same temperature. Thus obtained mixture was dropwise added to the solution prepared in the similar manner as in Example 1 from 3-(1-methyl-1H-tetrazol-5-yl)thiomethyl-7-amino-3-cephem-4-carboxylic acid (7.8 g.), bis(trimethylsilyl)acetamide (22.9 ml.) and ethyl acetate (156 ml.), at −40° C. over 5 minutes with stirring. The mixture was stirred for 30 minutes at the same temperature and further stirred for 1 hour at −5° to 0° C. After the reaction, the reaction mixture was poured into 5% sodium bicarbonate aqueous solution (150 ml.), and the aqueous layer was separated. The remaining ethyl acetate layer was further extracted with 5% sodium bicarbonate aqueous solution, and the extract was combined with the separated aqueous layer. The aqueous solution was washed with ethyl acetate, and ethyl acetate was added thereto. The mixture was adjusted to pH 2 with 10% hydrochloric acid and filtered, and then the ethyl acetate layer was separated from the filtrate. The remaining aqueous layer was further extracted with ethyl acetate, and the extract was combined with the separated ethyl acetate layer. The ethyl acetate layer was washed with water, dried and then the solvent was distilled off. The residue was pulverized in diethyl ether, collected by filtration and dried to give 3-(1-methyl-1H-tetrazol-5-yl)thiomethyl-7-[2-(2-propanesulfonylamino-1,3-thiazol-4-yl)glyoxylamido]-3-cephem-4-carboxylic acid, which can be represented as 3-(1-methyl-1H-tetrazol-5-yl)-thiomethyl-7-[2-(2-propanesulfonylimino-2,3-dihydro-1,3-thiazol-4-yl)glyoxylamido]-3-cephem-4-carboxylic acid, (11.0 g.), m.p. 150° C. (dec.).

I.R. Spectrum (Nujol): 1780 ($\beta$-lactam) cm$^{-1}$,

N.M.R. Spectrum (d$_6$-dimethylsulfoxide, $\delta$): 3.73 (2H, broad s), 3.95 (3H, s), 4.2 and 4.45 (2H, AB$_q$, J=13 Hz), 5.15 (1H, d, J=5 Hz), 5.7 (1H, dd, J=4 and 5 Hz), 8.25 (1H, s).

EXAMPLE 7

(i) To dimethylformamide (0.12 g.) was dropwise added phosphorus oxychloride (0.29 g.) under stirring and ice-cooling, and the mixture was stirred for 30 minutes at 40° C. and then cooled to −20° C. To the mixture was added all at once a solution of 2-(2-tetrahydropyranyl)oxy-2-(2-mesylamino-1,3-thiazol-4-yl)acetic acid, which can be represented as 2-(2-tetrahydropyranyl)oxy-2-(2-mesylimino-2,3-dihydro-1,3-thiazol-4-yl)acetic acid, (0.52 g.) in ethyl acetate (7 ml.) at −20° C. with stirring, and then the mixture was stirred for 30 minutes at −20° to −10° C. Thus obtained mixture was added all at once to the solution prepared in the similar manner as in Example 1 from 3-(1-methyl-1H-tetrazol-5-yl)thiomethyl-7-amino-3-cephem-4-carboxylic acid (0.51 g.), bis(trimethylsilyl)acetamide (1.5 ml.) and ethyl acetate (10 ml.), at −40° C. The mixture was stirred for 30 minutes at the same temperature and further stirred for 1.5 hours at −20° to −10° C. After the reaction, the reaction mixture was poured into 5% sodium bicarbonate aqueous solution (20 ml.). The mixture was washed with ethyl acetate, and the aqueous layer was separated therefrom. Thus obtained aqueous layer was post-treated in a similar manner as that of example 5 to give 3-(1-methyl-1H-tetrazol-5-yl)thiomethyl-7-[2-(2-tetrahydropyranyl)oxy-2-(2-mesylamino-1,3-thiazol-4-yl)acetamido]-3-cephem-4-carboxylic acid, which can be represented as 3-(1-methyl-1H-tetrazol-5-yl)thiomethyl-7-[2-(2-tetrahydropyranyl)oxy-2-(2-mesylimino-2,3-dihydro-1,3-thiazol-4-yl)acetamido]-3-cephem-4-carboxylic acid, (0.41 g.)

(ii) To a mixture of 2-(2-tetrahydropranyl)oxy-2-(2-mesylamino-1,3-thiazol-4-yl)acetic acid, which can be represented as 2-(2-tetrahydropyranyl)oxy-2-(2-mesylimino-2,3-dihydro-1,3-thiazol-4-yl)acetic acid, (350 mg.), triethylamine (96 mg.), N,N-dimethylbenzylamine (half drop) and tetrahydrofuran (7 ml.) was dropwise added a mixture of butyl chloroformate (130 mg.) and tetrahydrofuran (1 ml.) over 1 minute at −15° C., and then the mixture was stirred for 30 minutes at −15° to −10° C. To the mixture was added all at once a mixture of 3-(1-methyl-1H-tetrazol-5-yl)thiomethyl-7-amino-3-cephem-4-carboxylic acid (224 mg.), triethylamine (80 mg.) and 50% tetrahydrofuran aqueous solution (10 ml.) which was cooled at 0° C., and the mixture was stirred for 30 minutes under ice-cooling and further stirred for 2 hours at room temperature. After the reaction, the reaction mixture was concentrated. The residue was adjusted to pH 8 with 5% sodium bicarbonate aqueous solution and washed with ethyl acetate. Thus obtained aqueous layer was adjusted to pH 1 with 10% hydrochloric acid and extracted with ethyl acetate. After distillation of the solvent from the extract, the residue was pulverized in diethyl ether, collected by filtration and dried to give pale brown powder of 3-(1-methyl-1H-tetrazol-5-yl)thiomethyl-7-[2-(2-tetrahydropyranyl)oxy-2-(2-mesylamino-1,3-thiazol-4-yl)acetamido]-3-cephem-4-carboxylic acid, which can be represented as 3-(1-methyl-1H-tetrazol-5-yl)thiomethyl-7-[2-(2-tetrahydropyranyl)oxy-2-(2-mesylimino-2,3-dihydro-1,3-thiazol-4-yl)acetamido]-3-cephem-4-carboxylic acid, (270 mg.).

N.M.R. Spectrum (d$_6$-dimethylsulfoxide, $\delta$): 2.95 (3H, s), 3.75 (2H, broad s), 3.95 (3H, s), 4.36 (2H, braod s), 4.6–4.8 (1H, broad s), 5.05–5.2 (1H, m), 5.5–5.8 (1H, m), 6.25–6.85 (1H, m).

EXAMPLE 8

To dimethylformamide (5 ml.) was dropwise added phosphorus oxychloride (0.794 g.) under stirring and ice-cooling, and the mixture was stirred for 30 minutes at 40° C., and then cooled to −20° C. To the mixture was gradually added 2-hydroxy-2-(2-formylamino-1,3-thiazol-4-yl)acetic acid, which can be represented as 2-hydroxy-2-(2-formylimino-2,3-dihydro-1,3-thiazol-4-yl)acetic acid, (0.505 g.) at −20° C., and the mixture was stirred for 45 minutes at −12° to −10° C. Thus obtained mixture was added to a solution, which was prepared by stirring a mixture of 3-(1-methyl-1H-tetrazol-5-yl)thiomethyl-7-amino-3-cephem-4-carboxylic acid (0.804 g.), bis(trimethylsilyl)acetamide (2.62 ml.) in methylene chloride (15 ml.) for an hour at room temperature and for 2 hours at 35° to 40° C. and then by cooling it to −30° C., at a time. The mixture was stirred for an hour at −20° to −15° C., and then methylene chloride was distilled off. The resulting residue was purified by a conventional manner to give 3-(1-methyl-1H-tetrazol-5-yl)thiomethyl-7-[2-hydroxy-2-(2-formylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-formylimino-2,3-dihydro-1,3-thiazol-4-yl)acetamido]-3-cephem-4-carboxylic acid, (0.51 g.).

I.R. Spectrum (Nujol): 1765 ($\beta$-lactam) cm$^{-1}$.

EXAMPLE 9

A suspension of 3-(1-methyl-1H-tetrazol-5-yl)thiomethyl-7-amino-3-cephem-4-carboxylic acid (1.46 g.), triethylamine (0.9292 g.) and dimethylaniline (0.713 g.) in methylene chloride (30 ml.) was stirred for 20 minutes at room temperature. To the mixture was added a solution of trimethylsilyl chloride (1.043 g.) in methylene chloride (10 ml.) over 5 minutes under ice-cooling, and the mixture was stirred for 2 hours at room temperature and then cooled to −25° C. On the other hand, a suspension of 2-(2-formylamino-1,3-thiazol-4-yl)glyoxylic acid, which can be represented as 2-(2-formylimino-2,3-dihydro-1,3-thiazol-4-yl)glyoxylic acid, (0.96 g.), thionyl chloride (0.697 g.) and dimethylformamide (0.214 g.) in methylene chloride (12 ml.) was stirred for 4 hours, and the mixture was added to the above obtained cooled mixture over 12 minutes at −25° to −20° C. The mixture was further stirred for 30 minutes at the same temperature and for 30 minutes at −20° to −10° C. After the reaction, the reaction mixture was added to water (100 ml.), and stirred for 30 minutes at room temperature. The white precipitates were collected by filtration and then dried to give dark brown powder of 3-(1-methyl-1H-tetrazol-5-yl)thiomethyl-7-[2-(2-formylamino-1,3-thiazol-4-yl)glyoxylamido]-3-cephem-4-carboxylic acid, which can be represented as 3-(1-methyl-1H-tetrazol-5-yl)thiomethyl-7-[2-(2-formylimino-2,3-dihydro-1,3-thiazol-4-yl)glyoxylamido]-3-cephem-4-carboxylic acid.

I.R. Spectrum (Nujol): 1782 ($\beta$-lactam) cm$^{-1}$,
N.M.R. Spectrum (d$_6$-dimethylsulfoxide, $\delta$): 3.78 (2H, broad s), 4.0 (3H, s), 4.4 (2H, broad s), 5.22 (1H, d, J=5 Hz), 5.8 (1H, d, J=5 Hz), 8.52 (1H, s), 8.62 (1H, s).

Similarly, the following compounds were obtained.

(1) 3-(1,3,4-Thiadiazol-2-yl)thiomethyl-7-[2-hydroxy-2-(2-formylamino-1,3-thiazol-4-yl)acetamido]-3-cephem-4-carboxylic acid, which can be represented as 3-(1,3,4-thiadiazol-2-yl)-thiomethyl-7-[2-hydroxy-2-(2-formylimino-2,3-dihydro-1,3-thiazol-4-yl)acetamido]-3-cephem-4-carboxylic acid.

I.R. Spectrum (Nujol): 1778 ($\beta$-lactam) cm$^{-1}$,
N.M.R. Spectrum (d$_6$-dimethylsulfoxide, $\delta$) 3.56 and 3.7 (2H, AB$_q$, J=16 Hz), 4.24 and 4.56 (aH, AB$_q$, J=14 Hz), 5.05–5.16 (2H, m), 5.62–5.78 (1H, m), 7.13 (1H, s), 8.43 (1H, s), 9.47 (1H, s).

(2) 3-(1-Methyl-1H-tetrazol-5-yl)thiomethyl-7-[2-formyloxy-2-(2-formylamino-1,3-thiazol-5-yl)acetamido]-3-cephem-4-carboxylic acid, which can be represented as 3-(1-methyl-1H-tetrazol-5-yl)-thiomethyl-7-[2-formyloxy-2-(2-formylimino-2,3-dihydro-1,3-thiazol-5-yl)acetamido]-3-cephem-4-carboxylic acid.

I.R. Spectrum (Nujol): 1780 ($\beta$-lactam) cm$^{-1}$,
N.M.R. Spectrum (d$_6$-dimethylsulfoxide, $\delta$), 3.53 and 3.77 (2H, AB$_q$, J=19 Hz), 3.92 (3H, s), 4.45 (2H, broad s), 4.95–5.15 (1H, m), 5.55–5.7 (1H, m), 6.4 (1H, s), 7.6 (1H, s), 8.27 (1H, s), 8.5 (1H, s).

(3) 3-(1-Methyl-1H-tetrazol-5-yl)thiomethyl-7-[2-(2-formylamino-1,3-thiazol-5-yl)glyoxylamido]-3-cephem-4-carboxylic acid, which can be represented as 3-(1-methyl-1H-tetrazol-5-yl)-thiomethyl-7-[2-(2-formylimino-2,3-dihydro-1,3-thiazol-5-yl)-glyoxylamido]-3-cephem-4-carboxylic acid.

I.R. Spectrum (Nujol): 1778 ($\beta$-lactam) cm$^{-1}$,
N.M.R. Spectrum (d$_6$-dimethylsulfoxide, $\delta$): 3.7 (2H, broad s), 3.95 (3H, s), 4.2 and 4.42 (2H, AB$_q$, J=18 Hz), 5.15 (1H, d, J=5 Hz), 5.52–5.8 (1H, m), 8.53 (1H, s), 8.65 (1H, s), (4) 7-[2-(2-Formylamino-1,3-thiazol-4-yl)glyoxylamido]-cephalosporanic acid, which can be represented as 7-[2-(2-formylimino-2,3-dihydro-1,3-thiazol-4-yl)glyoxylamido]cephalosporanic acid, mp. 145° C.

I.R. Spectrum (Nujol): 1780 ($\beta$-lactam) cm$^{-1}$,
N.M.R. Spectrum (d$_6$-dimethylsulfoxide, $\delta$): 2.06 (3H, s), 3.6 (2H, broad s), 4.7 and 5.08 (2H, AB$_q$, J=14 Hz), 5.22 (1H, d, J=5 Hz), 5.83 (1H, d, J=5 Hz), 8.47 (1H, s), 8.6 (1H, s).

(5) 3-Carbamoyloxymethyl-7-[2-(2-formylamino-1,3-thiazol-4-yl)glyoxylamido]-3-cephem-4-carboxylic acid, which can be represented as 3-carbamoyloxymethyl-7-[2-(2-formylimino-2,3-dihydro-1,3-thiazol-4-yl)glyoxylamido]-3-cephem-4-carboxylic acid.

I.R. Spectrum (Nujol): 1770 ($\beta$-lactam) cm$^{-1}$,
N.M.R. Spectrum (d$_6$-dimethylsulfoxide, $\delta$): 3.57 (2H, broad s), 4.65 and 4.87 (2H, AB$_q$, J=14 Hz), 5.2 (1H, d, J=5 Hz), 5.8 (1H, d, J=5 Hz), 8.43 (1H, s), 8.58 (1H, s).

(6) 3-(1-Methyl-1H-tetrazol-5-yl)thiomethyl-7-[2-[2-(methyl)thiocarbamoylamino-1,3-thiazol-4-yl]glyoxylamido]-3-cephem-4-carboxylic acid, which can be represented as 3-(1-methyl-1H-tetrazol-5-yl)thiomethyl-7-[2-[2-(methyl)thiocarbamoylimino-2,3-dihydro-1,3-thiazol-4-yl]-glyoxylamido]-3-cephem-4-carboxylic acid, 148° C. (sinter), 160° C. (expand), 200° C. (dec.).

I.R. Spectrum (Nujol): 1780 ($\beta$-lactam) cm$^{-1}$,
N.M.R. Spectrum (d$_6$-dimethylsulfoxide, $\delta$): 3.02 (3H, s), 3.75 (2H, broad s), 4.35 (2H, broad s), 5.17 (1H, d, J=5 Hz), 5.4–5.95 (1H, m), 8.25 (1H, s).

(7) 3-(5-Methyl-1,3,4-thiadiazol-2-yl)thiomethyl-7-[2-(2-formylamino-1,3-thiazol-4-yl)glyoxylamido]-3-cephem-4-carboxylic acid, which can be represented as 3-(5-methyl-1,3,4-thiadiazol-2-yl)thiomethyl-7-[2-(2-formylimino-2,3-dihydro-1,3-thiazol-4-yl)glyoxylamido]-3-cephem-4-carboxylic acid.

I.R. Spectrum (Nujol): 1780 ($\beta$-lactam) cm$^{-1}$,
N.M.R. Spectrum (d$_6$-dimethylsulfoxide, $\delta$): 2.7 (3H, s), 3.75 (2H, broad s), 4.25 and 4.62 (2H, AB$_q$, J=14

Hz), 5.12 (1H, d, J=5 Hz), 5.85 (1H, d, J=5 Hz), 8.5 (1H, s), 8.65 (1H, s).

(8) 3-(1,3,4-Thiadiazol-2-yl)thiomethyl-7-[2-(2-formylamino-1,3-thiazol-4-yl)glyoxylamido]-3-cephem-4-carboxylic acid, which can be represented as 3-(1,3,4-thiadiazol-2-yl)-thiomethyl-7-[2-(2-formylimino-2,3-dihydro-1,3-thiazol-4-yl)-glyoxylamido]-3-cephem-4-carboxylic acid, powder.

I.R. Spectrum (Nujol): 1775 ($\beta$-lactam) cm$^{-1}$,
N.M.R. Spectrum (d$_6$-dimethylsulfoxide, $\delta$): 3.64 and 3.86 (2H, AB$_q$, J=16 Hz), 4.32 and 4.66 (2H, AB$_q$, J=14 Hz), 5.22 (1H, d, J=5 Hz), 5.78 (1H, d, J=5 Hz), 8.45 (1H, s), 8.57 (1H, s), 9.57 (1H, s).

(9) 3-(1-Methyl-1H-tetrazol-5-yl)thiomethyl-7-[2-[2-(N-methyl-N-tert-pentyloxycarbonylamino)-1,3-thiazol-4-yl]glyoxylamido]-3-cephem-4-carboxylic acid, powder.

I.R. Spectrum (Nujol): 1790 ($\beta$-lactam) cm$^{-1}$,
N.M.R. Spectrum (CDCl$_3$, $\delta$): 3.6 (3H, s), 3.73 (2H, broad s), 3.9 (3H, s), 4.36 (3H, broad s), 5.13 (1H, d, J=5 Hz), 5.83 (1H, d, J=5 Hz), 8.7 (1H, s).

(10) 3-(1-Methyl-1H-tetrazol-5-yl)thiomethyl-7-[2-(2-formylamino-5-chloro-1,3-thiazol-4-yl)glyoxylamido]-3-cephem-4-carboxylic acid, which can be represented as 3-(1-methyl-1H-tetrazol-5-yl)thiomethyl-7-[2-(2-formylimino-5-chloro-2,3-dihydro-1,3-thiazol-4-yl)glyoxylamido]-3-cephem-4-carboxylic acid, power, mp. 148° to 155° C. (dec.).

I.R. Spectrum (Nujol): 3200, 1780, 1680 (broad), 1550, 1290, 1180, 1110 cm$^{-1}$,
N.M.R. Spectrum (d$_6$-acetone, $\delta$): 3.85 (2H, broad s), 4.00 (3H, s), 4.45 (2H, broad s), 5.28 (1H, d, J=5 Hz), 6.00 (1H, d, J=5 Hz), 8.71 (1H, s),

(11) 3-Methyl-7-[2-(2-formylamino-1,3-thiazol-4-yl)-glyoxylamido]-3-cephem-4-carboxylic acid, which can be represented as 3-methyl-7-[2-(2-formylimino-2,3-dihydro-1,3-thiazol-4-yl)-glyoxylamido]-3-cephem-4-carboxylic acid, mp. 180° C. and carbonized at 210° C.

(12) 3-(5-Methyl-1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-imino-2,3-dihydro-1,3-thiazol-4-yl)acetamido]-3-cephem-4-carboxylic acid, pale yellow powder.

(13) 3-(1,3,4-Thiadiazol-2-yl)thiomethyl-7-[2-hydroxy-2-(2-amino-1,3-thiazol-4-yl)acetamido]-3-cephem-4-carboxylic acid, which can be represented as 3-(1,3,4-thiadiazol-2-yl)-thiomethyl-7-[2-hydroxy-2-(2-imino-2,3-dihydro-1,3-thiazol-4-yl)-acetamido]-3-cephem-4-carboxylic acid, pale brown powder, mp. 151° to 180° C. (dec.).

(14) 3-(5-Methyl-1,3,4-oxadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-oxadiazol-2-yl)thiomethyl-7-[2-hydroxy-2-(2-imino-2-2,3-dihydro-1,3-thiazol-4-yl)acetamido]-3-cephem-4-carboxylic acid.

I.R. Spectrum (Nujol): 1780 ($\beta$-lactam) cm$^{-1}$,
(15) 3-(4-Methyl-4-H-1,2,4-triazol-3-yl)thiomethyl-7-[2-hydroxy-2-(2-amino-1,3-thiazol-4-yl)acetamido]-3-cephem-4-carboxylic acid, which can be represented as 3-(4-methyl-4H-1,2,4-triazol-3-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1760 ($\beta$-lactam) cm$^{-1}$,
(16) 3-Carbamoyloxymethyl-7-[2-hydroxy-2-(2-amino-1,3-thiazol-4-yl)acetamido]-3-cephem-4-carboxylic acid, which can be represented as 3-carbamoyloxymethyl-7-[2-hydroxy-2-(2-imino-2,3-dihydro-1,3-thiazol-4-yl)acetamido]-3-cephem-4-carboxylic acid, mp.>270° C.

(17) 3-Methyl-7-[2-hydroxy-2-(2-amino-1,3-thiazol-4-yl)-acetamido]-3-cephem-4-carboxylic acid, which can be represented as 3-methyl-7-[2-hydroxy-2-(2-imino-2,3-dihydro-1,3-thiazol-4-yl)acetamido]-3-cephem-4-carboxylic acid. mp.>250° C.

(18) 3-(1-Methyl-1H-tetrazol-5-yl)thiomethyl-7-[2-hydroxy-2-(2-amino-1,3-thiazol-5-yl)acetamido]-3-cephem-4-carboxylic acid, which can be represented as 3-(1-methyl-1H-tetrazol-5-yl)thiomethyl-7-[2-hydroxy-2-(2-imino-2,3-dihydro-1,3-thiazol-5-yl)acetamido]-3-cephem-4-carboxylic acid, mp. 130° to 200° C. (dec.).

(19) 3-(1-Methyl-1H-tetrazol-5-yl)thiomethyl-7-[2-hydroxy-2-(2-amino-5-chloro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-imino-5-chloro-2,3-dihydro-1,3-thiazol-4-yl)acetamido]-3-cephem-4-carboxylic acid, mp. 148° to 154° C. (dec.).

(20) 3-(1-Methyl-1H-tetrazol-5-yl)thiomethyl-7-[DL-2-hydroxy-2-(2-formylamino-5-chloro-1,3-thiazol-4-yl)acetamido]-3-cephem-4-carboxylic acid, which can be represented as 3-(1-methyl-1H-tetrazol-5-yl)thiomethyl-7-[DL-2-hydroxy-2-(2-formylimino-5-chloro-2,3-dihydro-1,3-thiazol-4-yl)acetamido]-3-cephem-4-carboxylic acid, mp. 160° to 165° C. (dec.).

(21) 3-(1-Methyl-1H-tetrazol-5-yl)thiomethyl-7-[2-hydroxy-2-(2-mesylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-mesylimino-2,3-dihydro-1,3-thiazol-4-yl)acetamido]-3-cephem-4-carboxylic acid, pale brown powder, mp. 120° to 146° C. (dec.).

(22) 3-(1-Methyl-1H-tetrazol-5-yl)thiomethyl-7-[2-hydroxy-2-(2-propanesulfonylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-propanesulfonylimino-2,3-dihydro-1,3-thiazol-4-yl)acetamido]-3-cephem-4-carboxylic acid, mp. 160° to 170° C. (dec.).

(23) 3-(1-Methyl-1H-tetrazol-5-yl)thiomethyl-7-[2-hydroxy-2-[2-(methyl)thiocarbamoylamino-1,3-thiazol-4-yl]acetamido]-3-cephem-4-carboxylic acid, which can be represented as 3-(1-methyl-1H-tetrazol-5-yl)thiomethyl-7-[2-hydroxy-2-[2-(methyl)-thiocarbamoylimino-2,3-dihydro-1,3-thiazol-4-yl]acetamido]-3-cephem-4-carboxylic acid, 155° C. (sinter), 160° C. (dec.). (24) 3-(1-Methyl-1H-tetrazol-5-yl)thiomethyl-7-[2-hydroxy-2-(2-methylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-methylimino-2,3-dihydro-1,3-thiazol-4-yl)acetamido]-3-cephem-4-carboxylic acid, mp. 144° to 156° C. (dec.).

(25) 3-(1-Methyl-1H-tetrazol-5-yl)thiomethyl-7-[DL-2-hydroxy-2-[2-(N-methyl-N-tert-pentyloxycarbonylamino)-1,3-thiazol-4-yl]acetamido]-3-cephem-4-carboxylic acid.

I.R. Spectrum (Nujol): 1770-1790 (broad) cm$^{-1}$,
(26) 3-(1-Methyl-1H-tetrazol-5-yl)thiomethyl-7-[2-hydroxy-2-(2-oxo-2,3-dihydro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-hydroxy-1,3-thiazol-4- yl)acetamido]-3-cephem-4-carboxylic acid, mp. 110° to 121° C. (dec.).

(27) 3-(1-Methyl-1H-tetrazol-5-yl)thiomethyl-7-[2-(2-amino-1,3-thiazol-4-yl)glyoxylamido]-3-cephem-4-carboxylic acid, which can be represented as 3-(1-methyl-1H-tetrazol-5-yl)thiomethyl-7-[2-(2-imino-2,3-dihydro-1,3-thiazol-4-yl)glyoxylaamido]-3-cephem-4-carboxylic acid, mp. 147° to 160° C. (dec.).

(28) 3-(5-Methyl-1,3,4-thiadiazol-2-yl)thiomethyl-7-[2-(2-amino-1,3-thiazol-4-yl)glyoxylamido]-3-cephem-4-carboxylic acid, which can be represented as 3-(5-methyl-1,3,4-thiadiazol-2-yl)-thiomethyl-7-[2-(2-imino-2,3-dihydro-1,3-thiazol-4-yl)glyoxyl-amido]-3-cephem-4-carboxylic acid, mp. 156° to 160° C. (dec.).

(29) 3-(5-Methyl-1,3,4-oxadiazol-2-yl)thiomethyl-7-[2-(2-amino-1,3-thiazol-4-yl)glyoxylamido]-3-cephem-4-carboxylic acid, which can be represented as 3-(5-methyl-1,3,4-oxadiazol-2-yl)thiomethyl-7-[2-(2-imino-2,3-dihydro-1,3-thiazol-4-yl)-glyoxylamido]-3-cephem-4-carboxylic acid.

I.R. Spectrum (Nujol): 1775 ($\beta$-lactam) cm$^{-1}$.

(30) 3-(4-Methyl-4H-1,2,4-triazol-3-yl)thiomethyl-7-[2-(2-amino-1,3-thiazol-4-yl)glyoxylamido]-3-cephem-4-carboxylic acid, which can be represented as 3-(4-methyl-4H-1,2,4-triazol-3-yl)thiomethyl-7-[2-(2-imino-2,3-dihydro-1,3-thiazol-4-yl)-glyoxylamido]-3-cephem-4-carboxylic acid.

I.R. Spectrum (Nujol): 1775 ($\beta$-lactam) cm$^{-1}$.

(31) 3-(1,3,4-Thiadiazol-2-yl)thiomethyl-7-[2-(2-amino-1,3-thiazol-4-yl)glyoxylamido]-3-cephem-4-carboxylic acid hydrochloride, which can be represented as 3-(1,3,4-thiadiazol-2-yl)-thiomethyl-7-[2-(2-imino-2,3-dihydro-1,3-thiazol-4-yl)glyoxylamido]-3-cephem-4-carboxylic acid hydrochloride, powder.

I.R. Spectrum (Nujol): 1778 ($\beta$-lactam) cm$^{-1}$.

(32) 3-Carbamoyloxymethyl-7-[2-(2-amino-1,3-thiazol-4-yl)glyoxylamido]-3-cephem-4-carboxylic acid hydrochloride, which can be represented as 3-carbamoyloxymethyl-7-[2-(2-imino-2,3-dihydro-1,3-thiazol-4-yl)glyoxylamido]-3-cephem-4-carboxylic acid hydrochloride, powder.

(33) 3-Methyl-7-[2-(2-amino-1,3-thiazol-4-yl)glyoxylamido]-3-cephem-4-carboxylic acid hydrochloride, which can be represented as 3-methyl-7-[2-(2-imino-2,3-dihydro-1,3-thiazol-4-yl)glyoxylamido]-3-cephem-4-carboxylic acid hydrochloride, dp.>250° C.

(34) 6-[2-(2-Amino-1,3-thiazol-4-yl)glyoxylamido]-5a,6-dihydro-3H,7H,azeto[2,1-b]furo[3,4d][1,3]thiazine-1,7-(4H)-dione hydrochloride, which can be represented as 6-[2-(2-imino-2,3-dihydro-1,3-thiazol-4-yl)glyoxylamido]-5a,6-dihydro-3H,7H-azeto[2,1-b]furo[3,4-d][1,3]thiazine-1,7-(4H)-dione hydrochloride.

I.R. Spectrum (Nujol): 1786 ($\beta$-lactam) cm$^{-1}$.

(35) 3-(1-Methyl-1H-tetrazol-5-yl)thiomethyl-7-[2-(2-amino-1,3-thiazol-5-yl)glyoxylamido]-3-cephem-4-carboxylic acid hydrochloride, which can be represented as 3-(1-methyl-1H-tetrazol-5-yl)thiomethyl-7-[2-(2-imino-2,3-dihydro-1,3-thiazol-5-yl)-glyoxylamido]-3-cephem-4-carboxylic acid hydrochloride, mp. 140° to 160° C. (dec.).

(36) 3-(1-Methyl-1H-tetrazol-5-yl)thiomethyl-7-[2-(2-methylamino-1,3-thiazol-4-yl)glyoxylamido]-3-cephem-4-carboxylic acid, which can be represented as 3-(1-methyl-1H-tetrazol-5-yl)-thiomethyl-7-[2-(2-methylimino-2,3-dihydro-1,3-thiazol-4-yl)-glyoxylamido]-3-cephem-4-carboxylic acid, mp. 146° to 155° C. (dec.).

EXAMPLE 10

To a solution of 3-(5-methyl-1,3,4-thiadiazol-2-yl)-thiomethyl-7-[2-(2-tert-pentyloxycarbonylamino-1,3-thiazol-4-yl)-glyoxylamido]-3-cephem-4-carboxylic acid, which can be represented as 3-(5-methyl-1,3,4-thiadiazol-2-yl)thiomethyl-7-[2-(2-tert-pentyloxycarbonylimino-2,3-dihydro-1,3-thiazol-4-yl)glyoxylamido]-3-cephem-4-carboxylic acid, (3.36 g.) in methanol (35 ml.) was added 1N sodium hydroxide aqueous solution (5.5 ml.) under ice-cooling, and to the mixture was dropwise added an aqueous solution of sodium borohydride (91 mg.) in water (2.5 ml.) over 2 minutes at 10° to 15° C. The mixture was stirred for 10 minutes at the same temperature, and the methanol was distilled off from the mixture below 40° C. under reduced pressure. The remaining aqueous solution was washed with a small amount of ethyl acetate, adjusted to pH 5 to 6, with 10% hydrochloric acid, further washed with a small amount of ethyl acetate. The solution was adjusted to pH 2 with 10% hydrochloric acid, and then extracted with ethyl acetate. The extract was washed with water and a saturated aqueous solution of sodium chloride in turn, dried over magnesium sulfate and then treated with an activated charcoal. The solvent was distilled off from the extract till the volume of the extract became a smaller amount. The precipitates were collected by filtration, washed with a small amount of ethyl acetate, and then dried to give 3-(5-methyl-1,3,4-thiadiazol-2-yl)thiomethyl-7-[2-hydroxy-2-(2-tert-pentyloxycarbonylamino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-tert-pentyloxycarbonylimino-2,3-dihydro-1,3-thiazol-4-yl)acetamido]-3-cephem-4-carboxylic acid, (1.69 g.). On the other hand, the mother liquor and the ethyl acetate washing were combined together and concentrated under reduced pressure, and then the precipitates were similarly treated as aforementioned to give the same object compound (0.80 g.).

I.R. Spectrum (Nujol): 1785 ($\beta$-lactam) cm$^{-1}$,
N.M.R. Spectrum (d$_6$-dimethylsulfoxide, $\delta$): 2.67 (3H, s), 3.55–3.83 (2H, broad s), 4.25 and 4.53 (2H, AB$_q$, J=14 Hz), 5.1 (1H, s), 5.13 (1H, d), 5.7 (1H, d), 7.05 (1H, s).

EXAMPLE 11

To a solution of 3-(1,3,4-thiadiazol-2-yl)thiomethyl-7-[2-(2-tert-pentyloxycarbonylamino-1,3-thiazol-4-yl)glyoxylamido]-3-cephem-4-carboxylic acid, which can be represented as 3-(1,3,4-thiadiazol-2-yl)thiomethyl-7-[2-(2-tert-pentyloxycarbonylimino-2,3-dihydro-1,3-thiazol-4-yl)glyoxylamido]-3-cephem-4-carboxylic acid, (3.1 g.) in methanol (30 ml.) was added 1N sodium hydroxide aqueous solution (5.2 ml.) under ice-cooling and stirring. To the mixture was dropwise added a solution of sodium borohydride (0.074 g.) in water (2 ml.) over 10 minutes, and the mixture was stirred for 30 minutes at the same temperature. After the reaction, the reaction mixture was concentrated under reduced pressure. To the residue were added water and ethyl acetate, and the aqueous layer was separated. The aqueous layer was adjusted to pH 5 to 6 with 10% hydrochloric acid and then washed with ethyl acetate. To the aqueous layer was added ethyl acetate, and the mixture was adjusted to pH 1 to 2 with 10% hydrochloric acid. The ethyl acetate layer was separated, washed with water, dried over magnesium sulfate and then treated with activated charcoal. After distillation of the solvent from the ethyl acetate layer, the remaining residue was pulverized in diethyl ether, collected by filtration and then dried to give pale yellow powder of 3-(1,3,4-thiadiazol-2-yl)thiomethyl-7-[2-hydroxy-2-(2-tert-pentyloxycarbonylamino-1,3-thiazol-4-yl)-acetamido]-3-cephem-4-carboxylic acid, which can be represented as 3-(1,3,4-thiadiazol-2-yl)thiomethyl-7-[2-hydroxy-2-(2-tert-pentyloxycarbonylimino-2,3-dihydro-1,3-thiazol-4-yl)acetamido]-3-cephem-4-carboxylic acid, (2.2 g.).

N.M.R. Spectrum ($d_6$-dimethylsulfoxide, $\delta$): 3.53 and 3.8 (2H, $AB_q$, J=17 Hz), 4.33 and 4.7 (2H, $AB_q$, J=13 Hz), 5.0 (1H, s), 5.15 (1H, d, J=4 Hz), 5.6 (1H, d, J=4 Hz), 7.0 (1H, s), 9.43 (1H, s).

EXAMPLE 12

To a solution of 7-[2-(2-tert-pentyloxycarbonylamino-1,3-thiazol-4-yl)glyoxylamido]cephalosporanic acid, which can be represented as 7-[2-(2-tert-pentyloxycarbonylimino-2,3-dihydro-1,3-thiazol-4-yl)glyoxylamido]cephalosporanic acid, (5.4 g.) in methanol (54 ml.) was added 1N sodium hydroxide aqueous solution (10 ml.) under cooling at 10° to 15° C. To the mixture was dropwise added a solution of sodium borohydride (142.2 mg.) in water (3.5 ml.) over 30 minutes at the same temperature, and then the mixture was stirred for 15 minutes at the same temperature. After the reaction, the reaction mixture was concentrated at 30° to 35° C. under reduced pressure. The residue was post-treated in a similar manner as that of example 11 to give powder of 7-[2-hydroxy-2-(2-tert-pentyloxycarbonylamino-1,3-thiazol-4-yl)acetamido]cephalosporanic acid, which can be represented as 7-[2-hydroxy-2-(2-tert-pentyloxycarbonylimino-2,3-dihydro-1,3-thiazol-4-yl)acetamido]cephalosporanic acid, (4.2 g.).

I.R. Spectrum (Nujol): 1783 ($\beta$-lactam) cm$^{-1}$,
N.M.R. Spectrum ($d_6$-dimethylsulfoxide, $\delta$): 2.07 (3H, s), 4.7 and 5.07 (2H, $AB_q$, J=14 Hz), 5.08 (1H, s), 5.13 (1H, d, J=5 Hz), 5.53–5.95 (1H, m), 7.03 (1H, s).

EXAMPLE 13

To a mixture of 3-(1-methyl-1H-tetrazol-5-yl)thiomethyl-7-[2-(2-propanesulfonylamino-1,3-thiazol-4-yl)glyoxylamido]-3-cephem-4-carboxylic acid, which can be represented as 3-(1-methyl-1H-tetrazol-5-yl)thiomethyl-7-[2-(2-propanesulfonylimino-2,3-dihydro-1,3-thiazol-4-yl)glyoxylamido]-3-cephem-4-carboxylic acid, (8.0 g.), methanol (160 ml.) and 1N sodium hydroxide aqueous solution (13.6 ml.) was dropwise added a mixture of sodium borohydride (0.26 g.) and ethanol (15 ml.) over 20 minutes under stirring and ice-cooling. The mixture was further stirred for 1 hour, and then methanol was distilled off. The residue was dissolved in water, and the solution was washed with ethyl acetate. To the aqueous solution was added ethyl acetate, and the mixture was adjusted to pH 2 with 10% hydrochloric acid, and then the ethyl acetate layer was separated from the mixture. The remaining aqueous layer was saturated with sodium chloride and then extracted with ethyl acetate. The ethyl acetate extract was combined with the separated ethyl acetate layer, washed with a saturated aqueous solution of sodium chloride and then dried. The solvent was distilled off, and the residue was washed with diethyl ether and then dried to give 3-(1-methyl-1H-tetrazol-5-yl)thiomethyl-7-[2-hydroxy-2-(2-propanesulfonylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-propanesulfonylimino-2,3-dihydro-1,3-thiazol-4-yl)acetamido]-3-cephem-4-carboxylic acid, (5.5 g.), mp. 160° to 170° C. (dec.).

N.M.R. Spectrum ($d_6$-dimethylsulfoxide, $\delta$): 3.73 (2H, broad s), 3.97 (3H, s), 4.35 (2H, broad s), 5.03 (1H, broad s), 5.13 (1H, d, J=5 Hz), 5.5–5.9 (1H, m), 6.67 (1H, s).

EXAMPLE 14

To a mixture of 3-(1-methyl-1H-tetrazol-5-yl)thiomethyl-7-[2-(2-oxo-2,3-dihydro-1,3-thiazol-4-yl)glyoxylamido]-3-cephem-4-carboxylic acid, which can be represented as 3-(1-methyl-1H-tetrazol-5-yl)thiomethyl-7-[2-(2-hydroxy-1,3-thiazol-4-yl)glyoxylamido]-3-cephem-4-carboxylic acid, (5.2 g.), methanol (200 ml.) and 1N sodium hydroxide aqueous solution (10.8 ml.) was dropwise added a mixture of sodium borohydride (0.205 g.) and ethanol (8 ml.) over 10 minutes at 5° to 10° C. with stirring. The mixture was further stirred for 20 minutes at the same temperature, and then a mixture of sodium borohydride (0.01 g.) and ethanol (0.5 ml.) was further added thereto at the same temperature. The mixture was further stirred for 30 minutes at the same temperature, and then the reaction mixture was concentrated under reduced pressure. To the residue was added water (200 ml.), and the solution was washed with ethyl acetate. The aqueous solution was adjusted to pH 5 with 10% hydrochloric acid and washed with ethyl acetate. The solution was adjusted to pH 1 with 10% hydrochloric acid and extracted with ethyl acetate. The remaining aqueous layer was subjected to salting-out and then further extracted with ethyl acetate. The ethyl acetate extracts were combined together, washed with a saturated aqueous solution of sodium chloride, dried over magnesium sulfate and then treated with activated charcoal. The solvent was distilled off, and the residue was pulverized in diethyl ether, collected by filtration and then dried to give pale yellow powder of 3-(1-methyl-1H-tetrazol-5-yl)thiomethyl-7-[2-hydroxy-2-(2-oxo-2,3-dihydro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-hydroxy-1,3-thiazol-4-yl)acetamido]-3-cephem-4-carboxylic acid, (3.6 g.), mp. 110° to 121° C. (dec.).

I.R. Spectrum (Nujol): 1780 ($\beta$-lactam) cm$^{-1}$,
N.M.R. Spectrum (NaDCO$_3$, $\delta$): 3.45 and 3.83 (2H, $AB_q$, J=18 Hz), 4.08 (3H, s), 4.04 and 4.42 (2H, $AB_q$, J=14 Hz), 4.85 (1H, s), 5.15 (1H, d, J=4 Hz), 5.6 (1H, d, J=4 Hz), 6.5 (1H, s).

EXAMPLE 15

To a solution of 3-(1-methyl-1H-tetrazol-5-yl)thiomethyl-7-[2-[2-(N-methyl-N-tert-pentyloxycarbonylamino)-1,3-thiazol-4-yl]glyoxylamido]-3-cephem-4-carboxylic acid (2.2 g.) in methanol (22 ml.) was added a 1N sodium hydroxide aqueous solution (3.6 ml.) under cooling at 10° C., and to the mixture was dropwise added an aqueous solution of sodium borohydride (41 mg.) in water (1 ml.) over 20 minutes under cooling at 10° to 15° C. The mixture was stirred for 30 minutes at the same temperature, and then methanol was distilled off from the mixture under reduced pressure. To the residue were added water (20 ml.) and ethyl acetate (40 ml.), and the aqueous layer was separated. To the aqueous layer was added ethyl acetate, and the mixture was adjusted to pH 1 to 2 with hydrochloric acid, and then the ethyl acetate layer was separated. The ethyl acetate layer was washed with a saturated aqueous solution of sodium chloride, dried over magnesium sulfate and then treated with an activated charcoal. The solvent was distilled off from the ethyl acetate layer, and the remaining oily substance was pulverized in diethyl ether. The powder was collected by filtration and then dried to give 3-(1-methyl-1H-tetrazol-5-yl)thiomethyl-7-[DL-2-hydroxy-2-[2-(N-methyl-N-tert-pentyloxycarbonylamino)-1,3-thiazol-4-yl]acetamido]-3-cephem-4-carboxylic acid (1.7 g.).

I.R. Spectrum (Nujol): 1770–1790 (broad) cm$^{-1}$,

N.M.R. Spectrum (CDCl$_3$, δ): 3.5 (3H, s), 3.65 (2H, broad s), 3.9 (3H, s), 4.35 (2H, broad s), 5.05 (1H, d, J=5 Hz), 5.25 (1H, s), 5.8 (1H, d, J=5 Hz), 6.95 (1H, s).

Similarly the following compounds were obtained.

(1) 3(5-Methyl-1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-imino-2,3-dihydro-1,3-thiazol-4-yl)acetamido]-3-cephem-4-carboxylic acid, pale yellow powder.

(2) 3-(1,3,4-Thiadiazol-2-yl)thiomethyl-7-[2-hydroxy-2-(2-amino-1,3-thiazol-4-yl)acetamido]-3-cephem-4-carboxylic acid, which can be represented as 3-(1,3,4-thiadiazol-2-yl)-thiomethyl-7-[2-hydroxy-2-(2-imino-2,3-dihydro-1,3-thiazol-4-yl)-acetamido]-3-cephem-4-carboxylic acid, pale brown powder, mp. 151° to 180° C. (dec.).

(3) 3-(1-Methyl-1H-tetrazol-5-yl)thiomethyl-7-[2-hydroxy-2-(2-mesylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-mesylimino-2,3-dihydro-1,3-thiazol-4-yl)acetamido]-3-cephem-4-carboxylic acid, pale brown powder, mp. 120° to 146° C. (dec.).

(4) 3-(1-Methyl-1H-tetrazol-5-yl)thiomethyl-7-[2-hydroxy-2-(2-tert-pentyloxycarbonylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-tert-pentyloxycarbonylimino-2,3-dihydro-1,3-thiazol-4-yl)acetamido]-3-cephem-4-carboxylic acid, pale brown powder.

(5) 3-(5-Methyl-1,3,4-oxadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-oxadiazol-2-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1780 (β-lactam) cm$^{-1}$.

(6) 3-(4-Methyl-4H-1,2,4-triazol-3-yl)thiomethyl-7-[2-hydroxy-2-(2-amino-1,3-thiazol-4-yl)acetamido]-3-cephem-4-carboxylic acid, which can be represented as 3-(4-methyl-4H-1,2,4-triazol-3-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1760 (β-lactam) cm$^{-1}$.

(7) 3-(1-Methyl-1H-tetrazol-5-yl)thiomethyl-7-[2-hydroxy-2-(2-formylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-formylimino-2,3-dihydro-1,3-thiazol-4-yl)acetamido]-3-cephem-4-carboxylic acid, brownish white powder.

N.M.R. Spectrum (d$_6$-dimethylsulfoxide, δ): 3.67 (2H, broad s), 3.9 (3H, s), 4.25 (2H, broad s), 5.05 (1H, d, J=5 Hz), 5.1 (1H, s), 5.53–5.8 (1H, m), 7.07 (1H, s), 8.45 (1H, s).

(8) 3-(1-Methyl-1H-tetrazol-5-yl)thiomethyl-7-[DL-2-hydroxy-2-(2-formylamino-5-chloro-1,3-thiazol-4-yl)acetamido]-3-cephem-4-carboxylic acid, which can be represented as 3-(1-methyl-1H-tetrazol-5-yl)thiomethyl-7-[DL-2-hydroxy-2-(2-formylimino-5-chloro-2,3-dihydro-1,3-thiazol-4-yl)acetamido]-3-cephem-4-carboxylic acid, mp. 160° to 165° C. (dec.).

I.R. Spectrum (Nujol): 3100–3600, 1780, 1680 (broad), 1530, 1280, 1175, 1100, 1055 cm$^{-1}$, N.M.R. Spectrum (d$_6$-dimethylsulfoxide, δ): 3.83 (2H, broad s), 4.03 (3H, s), 4.43 (2H, broad s), 5.23 (1H, d, J=5 Hz), 5.42 (1H, s), 5.87 (1H, d, J=5 Hz), 8.78 (1H, s).

(9) 3-(1-Methyl-1H-tetrazol-5-yl)thiomethyl-7-[2-hydroxy-2-[2-(methyl)thiocarbamoylamino-1,3-thiazol-4-yl]acetamido]-3-cephem-4-carboxylic acid, which can be represented as 3-(1-methyl-1H-tetrazol-5-yl)thiomethyl-7-[2-hydroxy-2-[2-(methyl)-thiocarbamoylimino-2,3-dihydro-1,3-thiazol-4-yl]-acetamido]-3-cephem-4-carboxylic acid, 155° C. (sinter), 160° C. (dec.).

I.R. Spectrum (Nujol): 1780 (β-lactam) cm$^{-1}$,

N.M.R. Spectrum (d$_6$-dimethylsulfoxide, δ): 3.06 (3H, s), 3.75 (2H, broad s), 4.33 (2H, broad s), 5.15 (2H, m), 5.64 and 5.78 (1H, m), 7.05 (1H, s).

(10) 3-(1,3,4-Thiadiazol-2-yl)thiomethyl-7-[2-hydroxy-2-(2-formylamino-1,3-thiazol-4-yl)acetamido]-3-cephem-4-carboxylic acid, which can be represented as 3-(1,3,4-thiadiazol-2-yl)-thiomethyl-7-[2-hydroxy-2-(2-formylimino-2,3-dihydro-1,3-thiazol-4-yl)acetamido]-3-cephem-4-carboxylic acid, pale yellow powder, mp. 105° to 130° C. (dec.).

I.R. Spectrum (Nujol): 1760–1780 (β-lactam) cm$^{-1}$,

N.M.R. Spectrum (d$_6$-dimethylsulfoxide, δ): 3.37 (2H, broad s), 4.25 and 4.62 (2H, AB$_q$, J=14 Hz), 5.1 (1H, d, J=5 Hz), 5.15 (1H, s), 5.53–5.9 (1H, m), 7.15 (1H, s), 8.45 (1H, s), 9.62 (1H, s).

(11) 3-Carbamoyloxymethyl-7-[2-hydroxy-2-(2-amino-1,3-thiazol-4-yl)acetamido]-3-cephem-4-carboxylic acid, which can be represented as 3-carbamoyloxymethyl-7-[2-hydroxy-2-(2-imino-2,3-dihydro-1,3-thiazol-4-yl)acetamido]-3-cephem-4-carboxylic acid, mp.>270° C.

I.R. Spectrum (Nujol): 1780 (β-lactam) cm$^{-1}$,

N.M.R. Spectrum (d$_6$-dimethylsulfoxide, δ): 3.43 and 3.65 (2H, AB$_q$, J=14 Hz), 4.6 and 4.85 (2H, AB$_q$, J=15 Hz), 4.86 (1H, s), 5.1 (1H, d, J=5 Hz), 2.6–2.75 (1H, m), 6.43 (1H, s).

(12) 3-Methyl-7-[2-hydroxy-2-(2-amino-1,3-thiazol-4-yl)-acetamido]-3-cephem-4-carboxylic acid, which can be represented as 3-methyl-7-[2-hydroxy-2-(2-imino-2,3-dihydro-1,3-thiazol-4-yl)acetamido]-3-cephem-4-carboxylic acid, mp.>250° C.

I.R. Spectrum (Nujol): 1760–1780 (β-lactam) cm$^{-1}$

N.M.R. Spectrum (d$_6$-dimethylsulfoxide, δ): 2.07 (3H, s), 3.33 and 3.68 (2H, AB$_q$, J=18 Hz), 4.93 (1H, s), 5.1 (1H, d), 5.57–5.7 (1H, m), 6.5 (1H, s).

(13) 3-(1-Methyl-1H-tetrazol-5-yl)thiomethyl-7-[2-hydroxy-2-(2-amino-1,3-thiazol-5-yl)acetamido]-3-cephem-4-carboxylic acid, which can be represented as 3-(1-methyl-1H-tetrazol-5-yl)thiomethyl-7-[2-hydroxy-2(2-imino-2,3-dihydro-1,3-thiazol-5-yl)acetamido]-3-cephem-4-carboxylic acid, mp. 130° to 200° C. (dec.).

(14) 3-(1-Methyl-1H-tetrazol-5-yl)thiomethyl-7-[2-hydroxy-2-(2-amino-5-chloro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-imino-5-chloro-2,3-dihydro- 1,3-thiazol-4-yl)acetamido]-3-cephem-4-carboxylic acid, mp. 148° to 154° C. (dec.).

(15) 3-(1-Methyl-1H-tetrazol-5-yl)thiomethyl-7-8 2-hydroxy-2-(2-methylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-methylimino-2,3-dihydro-1,3-thiazol-4-yl)acetamido]-3-cephem-4-carboxylic acid, mp. 144° to 156° C. (dec.).

EXAMPLE 16

A solution of 3-(5-methyl-1,3,4-thiadiazol-2-yl)-thiomethyl-7-[2-hydroxy-2-(2-tert-pentyloxycarbonylamino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-tert-pentyloxycarbonylimino-2,3-dihydro-1,3-thiazol-4-yl)acetamido]-3-cephem-4-carboxylic acid (2.30 g.) in 98% formic acid (25 ml.) was stirred for 2.5 hours at room temperature. After the reaction, formic acid was distilled off under reduced pressure. The residue was pulverized in acetonitrile (25 ml.), collected by filtration, washed with a small amount of acetonitrile and then dissolved in 5% sodium bicarbonate aqueous solution (14 ml.). The solution was adjusted to pH 6 with acetic acid and subjected to alumina column chromatography by using pH 5.0 acetate buffer as an eluent. The eluate containing the object compound (300 ml.) was adjusted to pH 3 with 10% hydrochloric acid and then washed twice with ethyl acetate (50 ml.). The aqueous layer was subjected to column chromatography (Amberlite XAD-4 prepared by Rohm & Haas Co.), and the column was washed with water and then eluted with 20% methanol aqueous solution (100 ml.), 50% methanol aqueous solution (100 ml.) and 70% methanol aqueous solution (400 ml.) in turn. The eluates containing the object compound (500 ml.) were collected and then methanol was distilled off at 30° to 35° C. under reduced pressure. The remaining aqueous solution was lyophilized to give pale yellow powder of 3-(5-methyl-1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-imino-2,3-dihydro-1,3-thiazol-4-yl)acetamido]-3-cephem-4-carboxylic acid, (0.60 g.).

I.R. Spectrum (Nujol): 1770 ($\beta$-lactam) cm$^{-1}$,

N.M.R. Spectrum (NaDCO$_3$, $\delta$): 2.75 (3H, s), 3.4 and 3.75 (2H, AB$_q$, J=14 Hz), 4.0 and 4.52 (2H, AB$_q$, J=14 Hz), 5.15 (1H, d, J=5 Hz), 5.2 (1H, s), 5.7 (1H, m); 6.76 ($\frac{1}{2}$H, s), 6.9 ($\frac{1}{2}$H, s).

EXAMPLE 17

A mixture of 3-(1,3,4-thiadiazol-2-yl)thiomethyl-7-[2-hydroxy-2-(2-tert-pentyloxycarbonylamino-1,3-thiazol-4-yl)-acetamido]-3-cephem-4-carboxylic acid, which can be represented as 3-(1,3,4-thiadiazol-2-yl)thiomethyl-7-[2-hydroxy-2-(2-tert-pentyloxycarbonylimino-2,3-dihydro-1,3-thiazol-4-yl)acetamido]-3-cephem-4-carboxylic acid, (2.1 g.) and 98 to 100% formic acid (40 ml.) was stirred for 2.5 hours at room temperature. After the reaction, the reaction mixture was concentrated under reduced pressure. The residue was pulverized in acetonitrile, collected by filtration and then washed with ether to produce brown powder (1.3 g.). The powder was dissolved in 5% sodium bicarbonate aqueous solution (20 ml.) and then adjusted to pH 6 with acetic acid. The mixture was subject to neutral almina column chromatography by using pH 5.0 acetate buffer as an eluent. The eluates containing object compound (230 ml.) were collected, adjusted to pH 2.8 to 3.0 with 10% hydrochloric acid, washed with ethyl acetate, and then remaining ethyl acetate was distilled off from the eluates under reduced pressure. The resulting aqueous layer was subjected to column chromatography (Amberlite XAD-4 prepared by Rohm & Haas Co.), and the column was washed with water and then eluted with 20% methanol (80 ml.), 50% methanol (80 ml.) and 70% methanol (300 ml.) in turn. The eluates containing the object compound were collected and then methanol was distilled off under reduced pressure. The remaining aqueous solution was lyophillized to give pale brown powder of 3-(1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(1,3,4-thiadiazol-2-yl)thiomethyl-7-[2-hydroxy-2-(2-imino-2,3-dihydro-1,3-thiazol-4-yl)acetamido]-3-cephem-4-carboxylic acid, (0.40 g.), mp. 151° to 180° C. (dec.).

I.R. Spectrum (Nujol): 1770, 1680, 1620, 1520 cm$^{-1}$,

N.M.R. Spectrum (d$_6$-dimethylsulfoxide, $\delta$): 3.68 (2H, m), 4.43 (2H, dd, J=12.8 and 22.6 Hz), 4.87 (1H, broad s), 5.11 (1H, d, J=5.0 Hz), 5.2–6.1 (3H, m), 6.43 (1H, s), 9.57 (1H, s).

EXAMPLE 18

A mixture of 3-(1-methyl-1H-tetrazol-5-yl)thiomethyl-7-[2-(2-tert-pentyloxycarbonylamino-1,3-thiazol-4-yl)glyoxylamido]-3-cephem-4-carboxylic acid, which can be represented as 3-(1-methyl-1H-tetrazol-5-yl)thiomethyl-7-[2-(2-tert-pentyloxycarbonylimino-2,3-dihydro-1,3-thiazol-4-yl)glyoxylamido]-3-cephem-4-carboxylic acid, (1.8 g.) and 98 to 100% formic acid (40 ml.) was allowed to stand for 5 hours. After the reaction, the reaction mixture was post-treated in the similar manners as in Examples 16 to 17 to give 3-(1-methyl-1H-tetrazol-5-yl)thiomethyl-7-[2-(2-amino-1,3-thiazol-4-yl)glyoxylamido]-3-cephem-4-carboxylic acid, which can be represented as 3-(1-methyl-1H-tetrazol-5-yl)thiomethyl-7-[2-(2-imino-2,3-dihydro-1,3-thiazol-4-yl)glyoxylamido]-3-cephem-4-carboxylic acid, (0.32 g.), mp. 147° to 160° C. (dec.).

I.R. Spectrum (Nujol): 1770 ($\beta$-lactam) cm$^{-1}$,

N.M.R. Spectrum (d$_6$-dimethylsulfoxide, $\delta$): 3.73 (2H, broad s), 3.95 (3H, s), 4.2 and 4.5 (2H, AB$_q$, J=15 Hz), 5.15 (1H, d, J=5 Hz), 5.75 (1H, d, J=5 Hz), 7.8 (1H, s).

EXAMPLE 19

A solution of 3-(5-methyl-1,3,4-thiadiazol-2-yl)-thiomethyl-7-[2-(2-tert-pentyloxycarbonylamino-1,3-thiazol-4-yl)glyoxylamido]-3-cephem-4-carboxylic acid, which can be represented as 3-(5-methyl-1,3,4-thiadiazol-2-yl)thiomethyl-7-[2-(2-tert-pentyloxycarbonylimino-2,3-dihydro-1,3-thiazol-4-yl)-glyoxylamido]-3-cephem-4-carboxylic acid, (8.56 g.) in formic acid (180 ml.) was stirred for 5.5 hours at room temperature. After the reaction, the reaction mixture was post-treated in the similar manners as in Examples 16 to 17 to give 3-(5-methyl-1,3,4-thiadiazol-2-yl)thiomethyl-7-[2-(2-amino-1,3-thiazol-4-yl)glyoxylamido]-3-cephem-4-carboxylic acid, which can be represented as 3-(5-methyl-1,3,4-thiadiazol-2-yl)thiomethyl-7-[2-(2-imino-2,3-dihydro-1,3-thiazol-4-yl)glyoxylamido]-3-cephem-4-carboxylic acid, (2.6 g.), mp. 156° to 160° C. (dec.).

EXAMPLE 20

To a mixture of 3-(1-methyl-1H-tetrazol-5-yl)thiomethyl-7-[2-formyloxy-2-(2-formylamino-1,3-thiazol-5-yl)acetamido]-3-cephem-4-carboxylic acid, which can be represented as 3-(1-methyl-1H-tetrazol-5-yl)thiomethyl-7-[2-formyloxy-2-(2-formylimino-2,3-dihydro-1,3-thiazol-5-yl)acetamido]-3-cephem-4-carboxylic acid, (1.5 g.) in methanol (30 ml.) was added phosphorus oxychloride (1.06 g.) under ice-cooling and stirring, and the mixture was stirred for 1 hour at the same temperature and then further stirred for 4 hours at room temperature. To the reaction mixture was added diethyl ether (150 ml.), and the precipitates were collected by filtration and then dried. Thus obtained pale yellow powder (1.30 g.) was added to water (30 ml.), and the mixture was adjusted to pH 1 to 2 with 10% hydrochloric acid. The resulting solution was treated with an activated charcoal, washed with ethyl acetate and then adjusted to pH 7 with a 5% sodium bicarbonate aqueous solution. The solution was washed with ethyl acetate, adjusted to pH 3 with 10% hydrochloric acid and then filtered. The aqueous solution was adsorbed on a HP-20 (neutral resin) column, which was washed with water and then eluted with an aqueous methanol solution. The eluates containing the object compound were collected and then methanol was distilled off under reduced pressure. The remaining aqueous solution was lyophilized to give 3-(1-methyl-1H-tetrazol-5-yl)thiomethyl-7-[2-hydroxy-2-(2-amino-1,3-thiazol-5-yl)acetamido]-3-cephem-4-carboxylic acid, which can be represented as 3-(1-methyl-1H-tetrazol-5-yl)thiomethyl-7-(2-hydroxy-2-(2-imino-2,3-dihydro-1,3-thiazol-5-yl)acetamido]-3-cephem-4-carboxylic acid, (0.63 g.), mp. 130° to 200° C. (dec.).

I.R. Spectrum (Nujol): 1768 ($\beta$-lactam) cm$^{-1}$,
N.M.R. Spectrum (d$_6$-dimethylsulfoxide, $\delta$): 3.72 (2H, broad s), 3.92 (3H, s), 4.3 (2H, broad s), 5.05–5.25 (2H, m), 5.66 (1H, d, J=5 Hz), 7.0 (1H, s).

EXAMPLE 21

To a mixture of 7-[2-(2-formylamino-1,3-thiazol-4-yl)-glyoxylamido]cephalosporanic acid, which can be represented as 7-[2-(2-formylimino-2,3-dihydro-1,3-thiazol-4-yl)glyoxylamido]-cephalosporanic acid, (30 g.) in methanol (500 ml.) was dropwise added phosphorus oxychloride (22.2 g.) over 30 minutes under ice-cooling and stirring, and the mixture was stirred for 2.25 hours at the same temperature. The mixture was poured into diethyl ether (2500 ml.), and the mixture was stirred for 1 hour at room temperature. The precipitates were collected by filtration and then dried to give 6-[2-(2-amino-1,3-thiazol-4-yl)glyoxylamido]-5a,6-dihydro-3H,7H-azeto[2,1-b]furo[3,4-d][1,3]-thiazine-1,7-(4H)-dione hydrochloride, which can be represented as 6-[2-(2-imino-2,3-dihydro-1,3-thiazol-4-yl)glyoxylamido]-5a,6-dihydro-3H,7H-azeto[2,1-b]furo[3,4-d][1,3]-thiazine-1,7-(4H)-dione hydrochloride, (24.2 g.).

I.R. Spectrum (Nujol): 1786 ($\beta$-lactam) cm$^{-1}$,
N.M.R. Spectrum (d$_6$-dimethylsulfoxide, $\delta$): 3.84 (2H, broad s), 5.07 (2H, s), 5.25 (1H, d, J=5 Hz), 5.83 (1H, d, J=5 Hz), 8.32 (1H, s).

EXAMPLE 22

To a mixture of 3-(1-methyl-1H-tetrazol-5-yl)-thiomethyl-7-[2-(2-formylamino-1,3-thiazol-4-yl)glyoxylamido]-3-cephem-4-carboxylic acid, which can be represented as 3-(1-methyl-1H-tetrazol-5-yl)thiomethyl-7-[2-(2-formylimino-2,3-dihydro-1,3-thiazol-4-yl)glyoxylamido]-3-cephem-4-carboxylic acid, (24.8 g.) in methanol (500 ml.) was dropwise added phosphorus oxychloride (16.4 g.) over 15 minutes under cooling at 5° to 10° C. with stirring, and the mixture was stirred for 2.5 hours at the same temperature. The ¾ amount of methanol was distilled off from the reaction mixture under reduced pressure, and the residue was pulverized in diethyl ether. The powder was collected by filtration and then dried to give 3-(1-methyl-1H-tetrazol-5-yl)thiomethyl-7-[2-(2-amino-1,3-thiazol-4-yl)-glyoxylamido]-3-cephem-4-carboxylic acid hydrochloride, which can be represented as 3-(1-methyl-1H-tetrazol-5-yl)thiomethyl-7-[2-(2-imino-2,3-dihydro-1,3-thiazol-4-yl)glyoxylamido]-3-cephem-4-carboxylic acid hydrochloride.

I.R. Spectrum (Nujol): 1778 ($\beta$-lactam) cm$^{-1}$,
N.M.R. Spectrum (d$_6$-dimethylsulfoxide, $\delta$): 3.7 (2H, broad s), 4.0 (3H, s), 4.37 (2H, broad s), 5.23 (1H, d, J=5 Hz), 5.75 (1H, d, J=5 Hz), 8.27 (1H, s), 8.35 (1H, s).

Similarly, the following compounds were obtained.

(1) 3-(5-Methyl-1,3,4-oxadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-oxadiazol-2-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1780 ($\beta$-lactam) cm$^{-1}$.

(2) 3-(5-Methyl-1,3,4-oxadiazol-2-yl)thiomethyl-7-[2-(2-amino-1,3-thiazol-4-yl)glyoxylamido]-3-cephem-4-carboxylic acid, which can be represented as 3-(5-methyl-1,3,4-oxadiazol-2-yl)thiomethyl-7-[2-(2-imino-2,3-dihydro-1,3-thiazol-4-yl)-glyoxylamido]-3-cephem-4-carboxylic acid.

I.R. Spectrum (Nujol): 1775 ($\beta$-lactam) cm$^{-1}$.

(3) 3-(4Methyl-4H-1,2,4-triazol-3-yl)thiomethyl-7-[2-hydroxy-2-(2-amino-1,3-thiazol-4-yl)acetamido]-3-cephem-4-carboxylic acid, which can be represented as 3-(4-methyl-4H-1,2,4-triazol-3-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1760 ($\beta$-lactam) cm$^{-1}$.

(4) 3-(4-Methyl-4H-1,2,4-triazol-3-yl)thiomethyl-7-[2-(2-amino-1,3-thiazol-4-yl)glyoxylamido]-3-cephem-4-carboxylic acid, which can be represented as 3-(4-methyl-4H-1,2,4-triazol-3-yl)thiomethyl-7-[2-(2-imino-2,3-dihydro-1,3-thiazol-4-yl)-glyoxylamido]-3-cephem-4-carboxylic acid.

I.R. Spectrum (Nujol): 1775 ($\beta$-lactam) cm$^{-1}$.

(5) 3-Carbamoyloxymethyl-7-[2-hydroxy-2-(2-amino-1,3-thiazol-4-yl)acetamido]-3-cephem-4-carboxylic acid, which can be represented as 3-carbamoyloxymethyl-7-[2-hydroxy-2-(2-imino-2,3-dihydro-1,3-thiazol-4-yl)acetamido]-3-cephem-4-carboxylic acid, mp.>270° C.

I.R. Spectrum (Nujol): 1780 ($\beta$-lactam) cm$^{-1}$,
N.M.R. Spectrum (d$_6$-dimethylsulfoxide, $\delta$): 3.43 and 3.65 (2H, AB$_q$, J=14 Hz), 4.6 and 4.85 (2H, AB$_q$, J=15 Hz), 4.86 (1H, s), 5.1 (1H, d, J=5 Hz), 2.6–2.75 (1H, m), 6.43 (1H, s).

(6) 3-(1-Methyl-1H-tetrazol-5-yl)thiomethyl-7-[2-hydroxy-2-(2-methylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-methylimino-2,3-dihydro-1,3-thiazol-4-yl)acetamido]-3-cephem-4-carboxylic acid, mp. 144° to 156° C. (dec.).

I.R. Spectrum (Nujol): 1764–1780 (broad, β-lactam) cm⁻¹,

N.M.R. Spectrum (d₆-dimethylsulfoxide, δ): 2.8 (3H, s), 3.57 and 3.78 (2H, AB$_q$, J=17 Hz), 3.9 (3H, s), 4.21 and 4.42 (2H, AB$_q$, J=15 Hz), 4.95 (1H, s), 5.12 (1H, d, J=5 Hz), 5.65–5.75 (1H, m), 6.57 (1H, s).

(7) 3-(1-Methyl-1H-tetrazol-5-yl)thiomethyl-7-[2-hydroxy-2-(2-amino-5-chloro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-imino-5-chloro-2,3-dihydro-1,3-thiazol-4-yl)acetamido]-3-cephem-4-carboxylic acid, mp. 148° to 154° C. (dec.)

I.R. Spectrum (Nujol): 3300 (broad), 1780, 1680, 1620 cm⁻¹,

N.M.R. Spectrum (d₆-acetone, δ): 3.87 (2H, broad s), 4.07 (3H, s), 4.37 (2H, broad s), 5.17 (1H, d, J=4 Hz), 5.20 (1H, s), 5.88 (1H, d, J=4 Hz).

(8) 3-Methyl-7-[2-(2-amino-1,3-thiazol-4-yl)glyoxylamido]-3-cephem-4-carboxylic acid hydrochloride, which can be represented as 3-methyl-7-[2-(2-imino-2,3-dihydro-1,3-thiazol-4-yl)glyoxylamido]-3-cephem-4-carboxylic acid hydrochloride, dp.>250° C.

I.R. Spectrum (Nujol): 1780 (β-lactam) cm⁻¹,

N.M.R. Spectrum (d₆-dimethylsulfoxide, δ): 2.12 (3H, s), 3.52 (2H, broad s), 5.17 (1H, d, J=5 Hz), 5.68 (1H, d, J=5 Hz), 8.3 (1H, s).

(9) 3-Carbamoyloxymethyl-7-[2-(2-amino-1,3-thiazol-4-yl)glyoxylamido]-3-cephem-4-carboxylic acid hydrochloride, which can be represented as 3-carbamoyloxymethyl-7-[2-(2-imino-2,3-dihydro-1,3-thiazol-4-yl)glyoxylamido]-3-cephem-4-carboxylic acid hydrochloride, powder.

(10) 3-(5-Methyl-1,3,4-thiadiazol-2-yl)thiomethyl-7-[2-(2-amino-1,3-thiazol-4-yl)glyoxylamido]-3-cephem-4-carboxylic acid hydrochloride, which can be represented as 3-(5-methyl-1,3,4-thiadiazol-2-yl)thiomethyl-7-[2-(2-imino-2,3-dihydro-1,3-thiazol-4-yl)glyoxylamido]-3-cephem-4-carboxylic acid hydrochloride, powder.

I.R. Spectrum (Nujol) cm⁻¹: 1760–1780 (broad, β-lactam) cm⁻¹,

N.M.R. Spectrum (d₆-dimethylsulfoxide, δ): 2.72 (3H, s), 3.75 (2H, broad s), 4.25 and 4.62 (2H, AB$_q$, J=14 Hz), 5.23 (1H, d, J=5 Hz), 5.75 (1H, d, J=5 Hz), 8.33 (1H, s).

(11) 3-(1,3,4-Thiadiazol-2-yl)thiomethyl-7-[2-(2-amino-1,3-thiazol-4-yl)glyoxylamido]-3-cephem-4-carboxylic acid hydrochloride, which can be represented as 3-(1,3,4-thiadiazol-2-yl)-thiomethyl-7-[2-(2-imino-2,3-dihydro-1,3-thiazol-4-yl)glyoxylamido]-3-cephem-4-carboxylic acid hydrochloride, powder.

I.R. Spectrum (Nujol): 1778 (β-lactam) cm⁻¹,

N.M.R. Spectrum (d₆-dimethylsulfoxide, δ): 3.7 (2H, broad s), 4.22 and 4.62 (2H, AB$_q$, J=16 Hz), 5.17 (1H, d, J=5 Hz), 5.7 (1H, d, J=5 Hz), 8.3 (1H, s), 9.67 (1H, s).

(12) 3-(1-Methyl-1H-tetrazol-5-yl)thiomethyl-7-[2-(2-amino-1,3-thiazol-5-yl)glyoxylamido]-3-cephem-4-carboxylic acid hydrochloride, which can be represented as 3-(1-methyl-1H-tetrazol-5-yl)thiomethyl-7-[2-(2-imino-2,3-dihydro-1,3-thiazol-5-yl)glyoxylamido]-3-cephem-4-carboxylic acid hydrochloride, mp. 140° to 160° C. (dec.).

I.R. Spectrum (Nujol): 1778 (β-lactam) cm⁻¹,

N.M.R. Spectrum (d₆-dimethylsulfoxide, δ): 3.7 (2H, broad s), 3.95 (3H, s), 4.3 (2H, broad s), 5.12 (1H, d, J=6 Hz), 5.65 (1H, d, J=6 Hz), 8.3 (1H, s).

(13) 3-(1-Methyl-1H-tetrazol-5-yl)thiomethyl-7-[2-(2-methylamino-1,3-thiazol-4-yl)glyoxylamido]-3-cephem-4-carboxylic acid, which can be represented as 3-(1-methyl-1H-tetrazol-5-yl)-thiomethyl-7-[2-(2-methylimino-2,3-dihydro-1,3-thiazol-4-yl)-glyoxylamido]-3-cephem-4-carboxylic acid, mp. 146° to 155° C. (dec.).

I.R. Spectrum (Nujol): 1798 (β-lactam) cm⁻¹,

N.M.R. Spectrum (d₆-dimethylsulfoxide, δ): 2.85 (3H, s), 3.58 and 3.79 (2H, AB$_q$, J=17 Hz), 3.92 (3H, s), 4.22 and 4.4 (2H, AB$_q$, J=14 Hz), 5.12 (1H, d, J=5 Hz), 5.75 (1H, d, J=5 Hz), 7.95 (1H, s).

(14) 3-Methyl-7-[2-hydroxy-2-(2-amino-1,3-thiazol-4-yl)-acetamido]-3-cephem-4-carboxylic acid, which can be represented as 3-methyl-7-[2-hydroxy-2-(2-imino-2,3-dihydro-1,3-thiazol-4-yl)acetamido]-3-cephem-4-carboxylic acid, mp.>250° C.

EXAMPLE 23

A mixture of 3-(1-methyl-1H-tetrazol-5-yl)thiomethyl-7-[2-(2-tetrahydropyranyl)oxy-2-(2-mesylamino-1,3-thiazol-4-yl)-acetamido]-3-cephem-4-carboxylic acid, which can be represented as 3-(1-methyl-1H-tetrazol-5-yl)thiomethyl-7-[2-(2-tetrahydropyranyl)oxy-2-(2-mesylimino-2,3-dihydro-1,3-thiazol-4-yl)acetamido]-3-cephem-4-carboxylic acid, (0.85 g.), ethanol (15 ml.), water (5 ml.) and 2N hydrochloric acid (5 ml.) was stirred for 2.5 hours at room temperature. After the reaction, the reaction mixture was diluted with water (20 ml.), adjusted to pH 8 with 5% sodium bicarbonate aqueous solution and then washed with diethyl ether. Thus obtained aqueous layer was adjusted to pH 4 to 5 with 10% hydrochloric acid and washed with ethyl acetate. The aqueous layer was adjusted to pH 1 to 2 with 10% hydrochloric acid and then extracted with ethyl acetate. The extract was washed with a saturated aqueous solution of sodium chloride and dried over magnesium sulfate. The solvent was distilled off from the extract, and the residue was washed in diethyl ether, collected by filtration and then dried to give pale brown powder of 3-(1-methyl-1H-tetrazol-5-yl)-thiomethyl-7-[2-hydroxy-2-(2-mesylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-mesylimino-2,3-dihydro-1,3-thiazol-4-yl)acetamido]-3-cephem-4-carboxylic acid, (0.2 g.), mp. 120° to 146° C. (dec.).

I.R. Spectrum (Nujol): 1780 (β-lactam) cm⁻¹,

N.M.R. Spectrum (d₆-dimethylsulfoxide, δ): 2.9 (3H, s), 3.57 and 3.8 (2H, AB$_q$, J=18 Hz), 3.9 (3H, s), 4.2 and 4.4 (2H, AB$_q$, J=13 Hz), 4.9–5.15 (2H, m), 5.5–5.75 (1H, m), 6.65 (1H, s).

EXAMPLE 24

A mixture of 3-(1-methyl-1H-tetrazol-5-yl)thiomethyl-7-[2-formyloxy-2-(2-tert-pentyloxycarbonylamino-1,3-thiazol-4-yl)acetamido]-3-cephem-4-carboxylic acid, which can be represented as 3-(1-methyl-1H-tetrazol-5-yl)thiomethyl-7-[2-formyloxy-2-(2-tert-pentyloxycarbonylimino-2,3-dihydro-1,3-thiazol-4-yl)-acetamido]-3-cephem-4-carboxylic acid, (1.49 g.) and 5% sodium bicarbonate aqueous solution (100 ml.) was allowed to stand for 6 hours. After the reaction, the reaction mixture was washed with ethyl acetate. To the reaction mixture was added ethyl acetate, and the mixture was adjusted to pH 7 with dilute hydrochloric acid and then the aqueous layer was separated. To the aqueous layer was added ethyl acetate, and the mixture was adjusted to pH 1 to 2 with dilute hydrochloric acid, and the ethyl acetate layer was separated. The remaining aqueous layer was subjected to salting-out and then extracted with ethyl acetate. The ethyl acetate layer and the ethyl acetate extract were combined together, washed with water, dried over magnesium sulfate, and then the solvent was distilled off. To the residue (2.0 g.) was added diethyl ether, and the mixture was stirred for overnight, collected by filtration and then dried to give pale brown powder of 3-(1-methyl-1H-tetrazol-5-yl)thiomethyl-7-[2-hydroxy-2-(2-tert-pentyloxycarbonylamino-1,3-thiazol-4-yl)-acetamido]-3-cephem-4-carboxylic acid, which can be represented as 3-(1-methyl-1H-tetrazol-5-yl)thiomethyl-7-[2-hydroxy-2-(2-tert-pentyloxycarbonylimino-2,3-dihydro-1,3-thiazol-4-yl)-acetamido]-3-cephem-4-carboxylic acid, (0.90 g.).

I.R. Spectrum (Nujol):
1785 ($\beta$-lactam), 1680–1730 (CO) cm$^{-1}$,

N.M.R. Spectrum (d$_6$-dimethylsulfoxide, $\delta$): 3.58 and 3.82 (2H, AB$_q$, J=18 Hz), 3.93 (3H, s), 4.22 and 4.33 (2H, AB$_q$, J=12 Hz), 5.0–5.12 (2H, m), 5.55–5.8 (1H, m), 7.03 (1H, s).

Similarly, the following compounds were obtained.

(1) 3-(5-Methyl-1,3,4-thiadiazol-2-yl)thiomethyl-7-[2-hydroxy-2-(2-tert-pentyloxycarbonylamino-1,3-thiazol-4-yl)-acetamido]-3-cephem-4-carboxylic acid, which can be represented as 3-(5-methyl-1,3,4-thiadiazol-2-yl)thiomethyl-7-[2-hydroxy-2-(2-tert-pentyloxycarbonylimino-2,3-dihydro-1,3-thiazol-4-yl)-acetamido]-3-cephem-4-carboxylic acid.

I.R. Spectrum (Nujol): 1785 ($\beta$-lactam) cm$^{-1}$, (2) 3-(1,3,4-Thiadiazol-2-yl)thiomethyl-7-[2-hydroxy-2-(2-tert-pentyloxycarbonylamino-1,3-thiazol-4-yl)acetamido]-3-cephem-4-carboxylic acid, which can be represented as 3-(1,3,4-thiadiazol-2-yl)thiomethyl-7-[2-hydroxy-2-(2-tert-pentyloxycarbonylimino-2,3-dihydro-1,3-thiazol-4-yl)acetamido]-3-cephem-4-carboxylic acid, pale yellow powder.

(3) 7-[2-Hydroxy-2-(2-tert-pentyloxycarbonylamino-1,3-thiazol-4-yl)acetamido]cephalosporanic acid, which can be represented as 7-[2-hydroxy-2-(2-tert-pentyloxycarbonylimino-2,3-dihydro-1,3-thiazol-4-yl)acetamido]cephalosporanic acid.

I.R. Spectrum (Nujol): 1783 ($\beta$-lactam) cm$^{-1}$.

(4) 3-(1-Methyl-1H-tetrazol-5-yl)thiomethyl-7-[2-hydroxy-2-(2-propanesulfonylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-propanesulfonyl-imino-2,3-dihydro-1,3-thiazol-4-yl)acetamido]-3-cephem-4-carboxylic acid, mp. 160° to 170° C. (dec.).

(5) 3-(1-Methyl-1H-tetrazol-5-yl)thiomethyl-7-[2-hydroxy-2-(2-oxo-2,3-dihydro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-hydroxy-1,3-thiazol-4-yl)acetamido]-3-cephem-4-carboxylic acid, mp. 110° to 121° C. (dec.).

(6) 3-(5-Methyl-1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-imino-2,3-dihydro-1,3-thiazol-4-yl)acetamido]-3-cephem-4-carboxylic acid, pale yellow powder.

(7) 3-(1,3,4-Thiadiazol-2-yl)thiomethyl-7-[2-hydroxy-2-(2-amino-1,3-thiazol-4-yl)acetamido]-3-cephem-4-carboxylic acid, which can be represented as 3-(1,3,4-thiadiazol-2-yl)thiomethyl-7-[2-hydroxy-2-(2-imino-2,3-dihydro-1,3-thiazol-4-yl)acetamido]-3-cephem-4-carboxylic acid, mp. 151° to 180° C. dec.).

(8) 3-(5-Methyl-1,3,4-oxadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-oxadiazol-2-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1780 (62 -lactam) cm$^{-1}$.

(9) 3-(4-Methyl-4H-1,2,4-triazol-3-yl)thiomethyl-7-[2-hydroxy-2-(2-amino-1,3-thiazol-4-yl)acetamido]-3-cephem-4-carboxylic acid, which can be represented as 3-(4-methyl-4H-1,2,4-triazol-3-yl)thiomethyl-7-[2-hydroxy-2-(2-imino-2,3-dihydro-1,3-thiazol-4-yl)acetamido]-3-cephem-4-carboxylic acid.

I.R. Spectrum (Nujol): 1760 ($\beta$-lactam) cm$^{-1}$.

(10) 3-Carbamoyloxymethyl-7-[2-hydroxy-2-(2-amino-1,3-thiazol-4-yl)acetamido]-3-cephem-4-carboxylic acid, which can be represented as 3-carbamoyloxymethyl-7-[2-hydroxy-2-(2-imino-2,3-dihydro-1,3-thiazol-4-yl)acetamido]-3-cephem-4-carboxylic acid, mp.>270° C.

(11) 3-Methyl-7-[2-hydroxy-2-(2-amino-1,3-thiazol-4-yl)-acetamido]-3-cephem-4-carboxylic acid, which can be represented as 3-methyl-7-[2-hydroxy-2-(2-imino-2,3-dihydro-1,3-thiazol-4-yl)acetamido]-3-cephem-4-carboxylic acid, mp.>250° C.

(12) 3-(1-Methyl-1H-tetrazol-5-yl)thiomethyl-7-[2-hydroxy-2-(2-amino-1,3-thiazol-5-yl)acetamido]-3-cephem-4-carboxylic acid, which can be represented as 3-(1-methyl-1H-tetrazol-5-yl)thiomethyl-7-[2-hydroxy-2-(2-imino-2,3-dihydro-1,3-thiazol-5-yl)acetamido]-3-cephem-4-carboxylic acid, mp. 130° to 200° C. (dec.).

(13) 3-(1-Methyl-1H-tetrazol-5-yl)thiomethyl-7-[2-hydroxy-2-(2-amino-5-chloro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-imino-5-chloro-2,3-dihydro-1,3-thiazol-4-yl)acetamido]-3-cephem-4-carboxylic acid, mp. 148° to 154° C. (dec.).

(14) 3-(1-Methyl-1H-tetrazol-5-yl)thiomethyl-7-[2-hydroxy-2-(2-formylamino-1,3-thiazol-4-yl)acetamido]-3-cephem-4-carboxylic acid, which can be represented as 3-(1-methyl-1H-tetrazol-5-yl)-thiomethyl-7-[2-hydroxy-2-(2-formylimino-2,3-dihydro-1,3-thiazol-4-yl)acetamido]-3-cephem-4-carboxylic acid, brownish white powder.

(15) 3-(1,3,4-Thiadiazol-2-yl)thiomethyl-7-[2-hydroxy-2-(2-formylamino-1,3-thiazol-4-yl)acetamido]-3-cephem-4-carboxylic acid, which can be represented as 3-(1,3,4-thiadiazol-2-yl)-thiomethyl-7-[2-hydroxy-2-(2-formylimino-2,3-dihydro-1,3-thiazol-4-yl)acetamido]-3-cephem-4-carboxylic acid, mp. 105° to 130° C. (dec.).

(16) 3-(1-Methyl-1H-tetrazol-5-yl)thiomethyl-7-[DL-2-hydroxy-2-(2-formylamino-5-chloro-1,3-thiazol-4-yl)acetamido]-3-cephem-4-carboxylic acid, which can be represented as 3-(1-methyl-1H-tetrazol-5-yl)thiomethyl-7-[DL-2-hydroxy-2-(2-formylimino-5-chloro-2,3-dihydro-1,3-thiazol-4-yl)acetamido]-3-cephem-4-carboxylic acid, mp. 160° to 165° C. (dec.).

(17) 3-(1-Methyl-1H-tetrazol-5-yl)thiomethyl-7-[2-hydroxy-2-[2-(methyl)thiocarbamoylamino-1,3-thiazol-4-yl]acetamido]-3-cephem-4-carboxylic acid, which can be represented as 3-(1-methyl-1H-tetrazol-5-yl)thiomethyl-7-[2-hydroxy-2-[2-(methyl)thiocarbamoylimino-2,3-dihydro-1,3-thiazol-4-yl]acetamido]-

3-cephem-4-carboxylic acid, 155° C. (sinter), 160° C. (dec.).

(18) 3-(1-Methyl-1H-tetrazol-5-yl)thiomethyl-7-[2-hydroxy-2-(2-methylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-methylimino-2,3-dihydro-1,3-thiazol-4-yl)acetamido]-3-cephem-4-carboxylic acid, mp. 144° to 156° C. (dec.).

(19) 3-(1-Methyl-1H-tetrazol-5-yl)thiomethyl-7-[DL-2-hydroxy-2-[2-(N-methyl-N-tert-pentyloxycarbonylamino)-1,3-thiazol-4-yl]acetamido]-3-cephem-4-carboxylic acid.

I.R. Spectrum (Nujol): 1770–1790 (broad) cm$^{-1}$.

(20) 3-(1-Methyl-1H-tetrazol-5-yl)thiomethyl-7-[2-hydroxy-2-(2-oxo-2,3-dihydro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-hydroxy-1,3-thiazol-4-yl)acetamido]-3-cephem-4-carboxylic acid, mp. 110° to 121° C. (dec.).

EXAMPLE 25

A solution of 7-[2-hydroxy-2-(2-tert-pentyloxycarbonylamino-1,3-thiazol-4-yl)acetamido]cephalosporanic acid, which can be represented as 7-[2-hydroxy-2-(2-tert-pentyloxycarbonylamino-2,3-dihydro-1,3-thiazol-4-yl)acetamido]cephalosporanic acid, (389 mg.), 5-methyl-1,3,4-oxadiazole-2-thiol (116.13 mg.), sodium bicarbonate (119.4 mg.) in pH 5.2 phosphate buffer (15 ml.) was adjusted to pH 5.2 with 10% hydrochloric acid and was stirred for 7 hours at 60° at 63° C. After the reaction, to the reaction mixture was added ethyl acetate, and the mixture was adjusted to pH 2 with 2N hydrochloric acid. The precipitates were collected by filtration and dried to give 3-(5-methyl-1,3,4-oxadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-oxadiazol-2-yl)thiomethyl-7-[2-hydroxy-2-(2-imino-2,3-dihydro-1,3-thiazol-4-yl)acetamido]-3-cephem-4-carboxylic acid, (60 mg.). On the other hand, from the remaining filtrate was separated the aqueous layer. The aqueous layer was washed with ethyl acetate, and the remaining ethyl acetate in the aqueous layer was distilled off under reduced pressure. The aqueous layer was subjected to column chromatography (non-ionic adsorption resin, Diaion HP 20 prepared by Mitsubishi Chemical Industries), washed with water and the eluted with 10% isopropyl alcohol. The eluates containing the object compound were collected and then isopropyl alcohol was distilled off under reduced pressure. The remaining aqueous solution was lyophilized to give the same object compound (75 mg.)

I.R. Spectrum (Nujol): 1780 (μ-lactam) cm$^{-1}$.

N.M.R. Spectrum (d$_6$-dimethylsulfoxide, δ): 3.65 (2H, broad s), 4.1 and 4.45 (2H, AB$_q$, J=15 Hz), 4.95 (1H, s), 5.1 (1H, d, J=5 Hz), 5.55–5.8 (1H, m), 6.7 (1H, s).

EXAMPLE 26

A solution of 7-[2-(2-tert-pentyloxycarbonylamino-1,3-thiazol-4-yl)glyoxylamido]cephalosporanic acid, which can be represented as 7-[2-(2-tert-pentyloxycarbonylimino-2,3-dihydro-1,3-thiazol-4-yl)glyoxylamido]cephalosporanic acid, (389 mg.), 5-methyl-1,3,4-oxadiazole-2-thiol (116.3 mg.), sodium bicarbonate (119.4 mg.) in pH 5.2 phosphate buffer (15 ml.) was adjusted to pH 5.2 with 10% hydrochloric acid and was stirred for 7 hours at 60° to 63° C. After the reaction, to the reaction mixture was added ethyl acetate, and the mixture was adjusted to pH 4.5 with 2N hydrochloric acid, and then the aqueous layer was separated. To the aqueous layer was added ethyl acetate, and the mixture was adjusted to pH 1.5 with 2N hydrochloric acid, and then the aqueous layer was separated. The aqueous layer was adjusted to pH 3 with 1N sodium hydroxide aqueous solution and then allowed to stand for overnight at cooling place. The precipitates were collected by filtration and then dried to give 3-(5-methyl-1,3,4-oxadiazol-2-yl)thiomethyl-7-[2-(2-amino-1,3-thiazol-4-yl)glyoxylamido]-3-cephem-4-carboxylic acid, which can be represented as 3-(5-methyl-1,3,4-oxadiazol-2-yl)thiomethyl-7-[2-(2-imino-2,3-dihydro-1,3-thiazol-4-yl)-glyoxylamido]-3-cephem-4-carboxylic acid, (30 mg.). On the other hand, the filtrate was subjected to column chromatography in similar manner as that of example 25 to give further the same object compound (65 mg.)

I.R. Spectrum (Nujol): 1775 (β-lactam) cm$^{-1}$,

N.M.R. Spectrum (d$_6$-dimethylsulfoxide, δ): 3.7 (2H, broad s), 4.2 and 4.45 (2H, AB$_q$, J=14 Hz), 5.2 (1H, d, J=5 Hz), 5.75 (1H, d, J=5 Hz), 8.1 (1H, s).

EXAMPLE 27

A mixture of 7-[2-hydroxy-2-(2-tert-pentyloxycarbonylamino-1,3-thiazol-4-yl)acetamido]cephalosporanic acid, which can be represented as 7-[2-hydroxy-2-(2-tert-pentyloxycarbonylimino-2,3-dihydro-1,3-thiazol-4-yl)acetamido]cephalosporanic acid, (389 mg.), 4-methyl-4H-1,2,4-triazole-3-thiol (115.2 mg.), sodium bicarbonate (119.4 mg.) and pH 5.2 phosphate buffer was stirred for 3 hours at 60° to 65° C. After the reaction, to the reaction mixture was added ethyl acetate, and the aqueous layer was separated. To the aqueous layer was added ethyl acetate, and the mixture was adjusted to pH 1 with 2N hydrochloric acid. The aqueous layer was separated, and the remaining ethyl acetate in the aqueous layer was removed under reduced pressure. The remaining aqueous solution was subjected to column chromatography (Amberlite XAD-4 prepared by Rohm & Haas Co.), and the column was washed with water and then eluted with 20 to 50% methanol aqueous solution. The eluates containing the object compounds were collected and the methanol was distilled off therefrom. The remaining aqueous solution was lyophilized to give 3-(4-methyl-4-H-1,2,4-triazol-3-yl)thiomethyl-7-[2-hydroxy-2-(2-amino-1,3-thiazol-4-yl)acetamido]-3-cephem-4-carboxylic acid, which can be represented as 3-(4-methyl-4H-1,2,4-triazol-3-yl)thiomethyl-7-[2-hydroxy-2-(2-imino-2,3-dihydro-1,3-thiazol-4-yl)acetamido]-3-cephem-4-carboxylic acid, (149 mg.).

I.R. Spectrum (Nujol): 1760 (β-lactam) cm$^{-1}$,

N.M.R. Spectrum (d$_6$-dimethylsulfoxide, δ): 3.57 (3H, s), 3.69 (2H, broad s), 4.0–4.3 (2H, m), 4.9 (1H, s), 5.1 (1H, d, J=5 Hz), 5.6–5.8 (1H, m), 6.6 (1H, s).

EXAMPLE 28

A mixture of 7-[2-(2-tert-pentyloxycarbonylamino-1,3-thiazol-4-yl)glyoxylamido]cephalosporanic acid, which can be represented as 7-[2-(2-tert-pentyloxycarbonylimino-2,3-dihydro-1,3-thiazol-4-yl)glyoxylamido]cephalosporanic acid, (378 mg.), 4-methyl-4H-1,2,4-triazole-3-thiol (115.2 mg.), sodium bicarbonate (119.4 mg.) and pH 5.2 phosphate buffer (15 ml. was stirred for 6 hours at 60° to 63° C. After the reaction, the reaction mixture was post-treated by conventional manners to give 3-(4-methyl-4H-1,2,4-triazol-3-yl)thiomethyl-7-[2-(2-amino-1,3-thiazol-4-yl)glyoxylamido]-3-cephem-4-carboxylic acid, which can be represented as 3-(4-methyl-4H-1,2,4-triazol-3-yl)thiomethyl-7-[2-(2-imino-2,3-dihydro-1,3-thiazol-4-yl)glyoxylamido]-3-cephem-4-carboxylic acid, (160 mg.).

I.R. Spectrum (Nujol): 1775 ($\beta$-lactam) cm$^{-1}$.

Similarly, the following compounds were obtained.

(1) 3-(1-Methyl-1H-tetrazol-5-yl)thiomethyl-7-[2-(2-oxo-2,3-dihydro-1,3-thiazol-4-yl)glyoxylamido]-3-cephem-4-carboxylic acid, which can be represented as 3-(1-methyl-1H-tetrazol-5-yl)thiomethyl-7-[2-(2-hydroxy-1,3-thiazol-4-yl)glyoxylamido]-3-cephem-4-carboxylic acid, pale yellow powder.

(2) 3-(1-Methyl-1H-tetrazol-5-yl)thiomethyl-7-[2-(2-propanesulfonylamino-1,3-thiazol-4-yl)glyoxylamido]-3-cephem-4-carboxylic acid, which can be represented as 3-(1-methyl-1H-tetrazol-5-yl) thiomethyl-7-[2-(2-propanesulfonylimino-2,3-dihydro-1,3-thiazol-4-yl)glyoxylamido]-3-cephem-4-carboxylic acid, mp. 150° C. (dec.).

(3) 3-(1-Methyl-1H-tetrazol-5-yl)thiomethyl-7-[2-hydroxy-2-(2-propanesulfonylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-propanesulfonylimino-2,3-dihydro-1,3-thiazol-4-yl)acetamido]-3-cephem-4-carboxylic acid, mp. 160° to 170° C. (dec.).

(4) 3-(1-Methyl-1H-tetrazol-5-yl)thiomethyl-7-[2-hydroxy-2-(2-oxo-2,3-dihydro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-hydroxy-1,3-thiazol-4-yl)acetamido]-3-cephem-4-carboxylic acid, mp. 110° to 121° C. (dec.).

(5) 3-(5-Methyl-1,3,4-thiadiazol-2-yl)thiomethyl-7-[2-hydroxy-2-(2-amino-1,3-thiazol-4-yl)acetamido]-3-cephem-4-carboxylic acid, which can be represented as 3-(5-methyl-1,3,4-thiadiazol-2-yl)thiomethyl-7-[2-hydroxy-2-(2-imino-2,3-dihydro-1,3-thiazol-4-yl)acetamido]-3-cephem-4-carboxylic acid, pale yellow powder.

(6) 3-(1,3,4-Thiadiazol-2-yl)thiomethyl-7-[2-hydroxy-2-(2-amino-1,3-thiazol-4-yl)acetamido]-3-cephem-4-carboxylic acid, which can be represented as 3-(1,3,4-thiadiazol-2-yl)thiomethyl-7-[2-hydroxy-2-(2-imino-2,3-dihydro-1,3-thiazol-4-yl)acetamido]-3-cephem-4-carboxylic acid, mp. 151° to 180° C. (dec.).

(7) 3-(1-Methyl-1H-tetrazol-5-yl)thiomethyl-7-[2-(2-amino-1,3-thiazol-4-yl)glyoxylamido]-3-cephem-4-carboxylic acid, which can be represented as 3-(1-methyl-1H-tetrazol-5-yl)thiomethyl-7-[2-(2-imino-2,3-dihydro-1,3-thiazol-4-yl)glyoxylamido]-3-cephem-4-carboxylic acid, mp. 147° to 160° C. (dec.).

(8) 3-(5-Methyl-1,3,4-thiadiazol-2-yl)thiomethyl-7-[2-(2-amino-1,3-thiazol-4-yl)glyoxylamido]-3-cephem-4-carboxylic acid, which can be represented as 3-(5-methyl-1,3,4-thiadiazol-2-yl)thiomethyl-7-[2-(2-imino-2,3-dihydro-1,3-thiazol-4-yl)glyoxylamido]-3-cephem-4-carboxylic acid, mp. 156° to 160° C. (dec.).

(9) 3-(1-Methyl-1H-tetrazol-5-yl)thiomethyl-7-[2-hydroxy-2-(2-mesylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-mesylimino-2,3-dihydro-1,3-thiazol-4-yl)acetamido]-3-cephem-4-carboxylic acid, mp. 120° to 146° C. (dec.).

(10) 3-(1-Methyl-1H-tetrazol-5-yl)thiomethyl-7-[2-hydroxy-2-(2-amino-1,3-thiazol-5-yl)acetamido]-3-cephem-4-carboxylic acid, which can be represented as 3-(1-methyl-1H-tetrazol-5-yl)thiomethyl-7-[2-hydroxy-2-(2-imino-2,3-dihydro-1,3-thiazol-5-yl)acetamido]-3-cephem-4-carboxylic acid, mp. 130° to 200° C. (dec.).

(11) 3-(1-Methyl-1H-tetrazol-5-yl)thiomethyl-7-[2-hydroxy-2-(2-amino-5-chloro-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-imino-5-chloro-2,3-dihydro-1,3-thiazol-4-yl)acetamido]-3-cephem-4-carboxylic acid, mp. 148° to 154° C. (dec.).

(12) 3-(1-Methyl-1H-tetrazol-5-yl)thiomethyl-7-[2-hydroxy-2-[2-(methyl)thiocarbamoylamino-1,3-thiazol-4-yl]acetamido]-3-cephem-4-carboxylic acid, which can be represented as 3-(1-methyl-1H-tetrazol-5-yl)thiomethyl-7-[2-hydroxy-2-[2-(methyl)-thiocarbamoylimino-2,3-dihydro-1,3-thiazol-4-yl]acetamido]-3-cephem-4-carboxylic acid, 155° C. (sinter), 160° C. (dec.).

(13) 3-(1-Methyl-1H-tetrazol-5-yl)thiomethyl-7-[2-hydroxy-2-(2-methylamino-1,3-thiazol-4-yl)acetamido]-3-cephem-4-carboxylic acid, which can be represented as 3-(1-methyl-1H-tetrazol-5-yl)thiomethyl-7-[2-hydroxy-2-(2-methylimino-2,3-dihydro-1,3-thiazol-4-yl)acetamido]-3-cephem-4-carboxylic acid, mp. 144° to 156° C. (dec.).

(14) 3-(1,3,4-Thiadiazol-2-yl)thiomethyl-7-[2-(2-amino-1,3-thiazol-4-yl)glyoxylamido]-3-cephem-4-carboxylic acid hydrochloride, which can be represented as 3-(1,3,4-thiadiazol-2-yl)-thiomethyl-7-[2-(2-imino-2,3-dihydro-1,3-thiazol-4-yl)glyoxylamido]-3-cephem-4-carboxylic acid hydrochloride, powder.

I.R. Spectrum (Nujol): 1778 ($\beta$-lactam) cm$^{-1}$.

(15) 3-(1-Methyl-1H-tetrazol-5-yl)thiomethyl-7-[2-(2-amino-1,3-thiazol-5-yl)glyoxylamido]-3-cephem-4-carboxylic acid hydrochloride, which can be represented as 3-(1-methyl-1H-tetrazol-5-yl)thiomethyl-7-[2-(2-imino-2,3-dihydro-1,3-thiazol-5-yl)-glyoxylamido]-3-cephem-4-carboxylic acid hydrochloride, mp. 140° to 160° C. (dec.).

(16) 3-(1-Methyl-1H-tetrazol-5-yl)thiomethyl-7-[2-(2-methylamino-1,3-thiazol-4-yl)glyoxylamido]-3-cephem-4-carboxylic acid, which can be represented as 3-(1-methyl-1H-tetrazol-5-yl)thiomethyl-7-[2-(2-methylimino-2,3-dihydro-1,3-thiazol-4-yl)glyoxylamido]-3-cephem-4-carboxylic acid, mp. 146° to 155° C. (dec.).

(17) 3-(1-Methyl-1H-tetrazol-5-yl)thiomethyl-7-[2-[2-(methyl)thiocarbamoylamino-1,3-thiazol-4-yl]glyoxylamino]-3-cephem-4-carboxylic acid, which can be represented as 3-(1-methyl-1H-tetrazol-5-yl)thiomethyl-7-[2-[2-(methyl)thiocarbamoylimino-2,3-dihydro-1,3-thiazol-4-yl]glyoxylamido]-3-cephem-4-carboxylic acid, 148° C. (sinter), 160° C. (expand), 200° C. (dec.).

What is claimed is:

1. A compound of the formula:

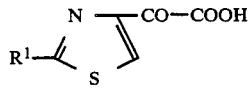

wherein R$^1$ is amino or amino, protected by an eliminatable protective group, or its carboxylic ester with a protective eliminatable esterifying group or a salt thereof.

2. The compound of claim 1, wherein
R¹ is amino, lower alkanoylamino, lower alkoxycarbonylamino, lower alkanesulfonylamino or lower alkyl (thiocarbamoyl)-amino,
or its carboxylic ester with a protective eliminatable esterifying group or a salt thereof.

3. The compound of claim 2, wherein
R¹ is amino or lower alkanoylamino, or its lower alkyl ester or a salt thereof.

4. The compound of claim 3, which is 2-(2-formylamino-1,3-thiazol-4-yl)glyoxylic acid.

5. The compound of claim 3, which is ethyl 2-(2-formylamino-1,3-thiazol-4-yl)glyoxylate.

6. The compound of claim 3, which is methyl 2-(2-formylamino-1,3-thiazol-4-yl)glyoxylate.

7. The compound of claim 3, which is 2-(2-amino-1,3-thiazol-4-yl)glyoxylic acid.

8. The compound of claim 3, which is ethyl 2-(2-amino-1,3-thiazol-4-yl)glyoxylate.

* * * * *